US010300031B2

(12) United States Patent
Singh

(10) Patent No.: US 10,300,031 B2
(45) Date of Patent: May 28, 2019

(54) PHARMACEUTICAL COMPOSITIONS FOR TREATING CHRONIC PAIN AND PAIN ASSOCIATED WITH NEUROPATHY

(75) Inventor: Chandra Ulagaraj Singh, San Antonio, TX (US)

(73) Assignee: Trinity Laboratories Inc., San Antonio, TX (US)

( * ) Notice: Subject to any disclaimer, the term of this patent is extended or adjusted under 35 U.S.C. 154(b) by 0 days.

(21) Appl. No.: 12/452,936

(22) PCT Filed: Aug. 6, 2008

(86) PCT No.: PCT/US2008/072360
§ 371 (c)(1),
(2), (4) Date: Jan. 29, 2010

(87) PCT Pub. No.: WO2009/021058
PCT Pub. Date: Feb. 12, 2009

(65) Prior Publication Data
US 2011/0039875 A1    Feb. 17, 2011

Related U.S. Application Data

(60) Provisional application No. 60/954,251, filed on Aug. 6, 2007.

(51) Int. Cl.
*A61K 31/137*    (2006.01)
*A61K 31/195*    (2006.01)
*A61K 31/485*    (2006.01)
*A61K 31/5377*   (2006.01)

(52) U.S. Cl.
CPC .......... *A61K 31/195* (2013.01); *A61K 31/137* (2013.01); *A61K 31/485* (2013.01); *A61K 31/5377* (2013.01)

(58) Field of Classification Search
CPC .. A61K 31/135; A61K 31/137; A61K 31/195; A61K 31/485
See application file for complete search history.

(56) References Cited

U.S. PATENT DOCUMENTS

| | | | |
|---|---|---|---|
| 4,602,909 A | | 7/1986 | Csillik et al. |
| 4,656,177 A | | 4/1987 | Sunshine et al. |
| 4,769,372 A | | 9/1988 | Kreek |
| 4,777,174 A | | 10/1988 | Sunshine et al. |
| 4,806,543 A | | 2/1989 | Choi |
| 5,248,678 A | | 9/1993 | Costa et al. |
| 5,352,683 A | | 10/1994 | Mayer et al. |
| 5,578,645 A | | 11/1996 | Askanazi et al. |
| 5,919,826 A | * | 7/1999 | Caruso .......................... 514/629 |
| 6,007,841 A | | 12/1999 | Caruso |
| 6,054,451 A | | 4/2000 | Caruso |
| 6,326,374 B1 | | 12/2001 | Magnus et al. |
| 7,064,140 B2 | | 6/2006 | Sunkel et al. |
| 8,017,623 B2 | * | 9/2011 | Singh ............................ 514/286 |
| 8,604,082 B2 | * | 12/2013 | Singh ............................ 514/569 |
| 2002/0115705 A1 | * | 8/2002 | Magnus-Miller et al. ... 514/403 |
| 2006/0240128 A1 | | 10/2006 | Schlagheck |
| 2007/0032500 A1 | | 2/2007 | Sun et al. |
| 2008/0176873 A1 | | 7/2008 | Streeper et al. |
| 2009/0312361 A1 | | 12/2009 | Streeper et al. |

FOREIGN PATENT DOCUMENTS

| | | | |
|---|---|---|---|
| WO | WO 99/37296 A1 | * | 7/1999 |
| WO | 2003/061656 A1 | | 7/2003 |
| WO | 2004/022002 A2 | | 3/2004 |
| WO | 2005/102390 A2 | | 11/2005 |
| WO | 2006/053012 A2 | | 5/2006 |

OTHER PUBLICATIONS

Lussier et al., Adjuvant analgesics in cancer pain management, Oncologist, 9: 571-591 (2004).
Pending Claims for U.S. Appl. No. 13/877,980.

* cited by examiner

*Primary Examiner* — Leslie A. Royds Draper
(74) *Attorney, Agent, or Firm* — Nevrivy Patent Law Group P.L.L.C.

(57) ABSTRACT

The present invention provides methods and compositions for the treatment of neuropathic pain. In certain embodiments, compositions comprising an dextromethorphan (or other N-methyl-D-aspartate receptor antagonist), tramadol, and gabapentin can synergistically act to reduce pain in a human patient. Pharmaceutical compositions may also comprise a capsaicinoid, an esterified capsaicinoid, and/or a tricyclic antidepressant.

8 Claims, 4 Drawing Sheets

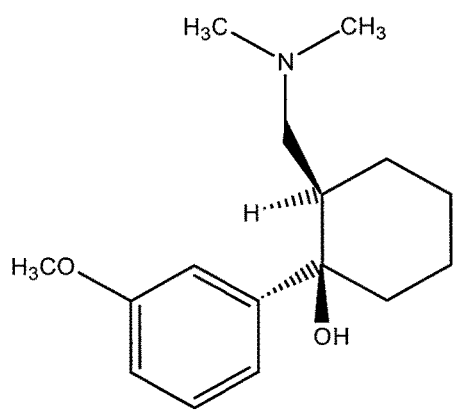
(+) Tramadol
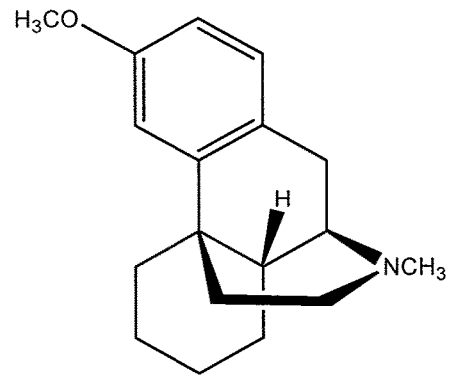
Dextromethorphan
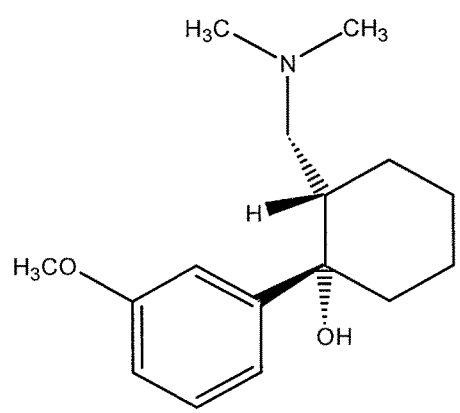
(-) Tramadol
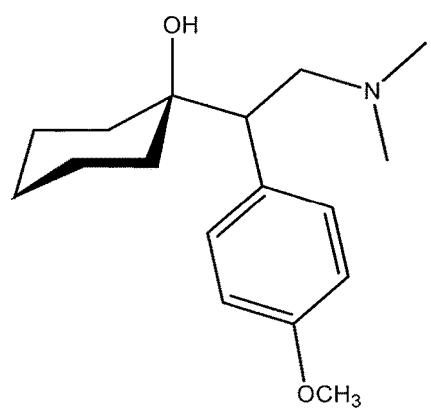
Venlafaxine
FIGURE. 1.

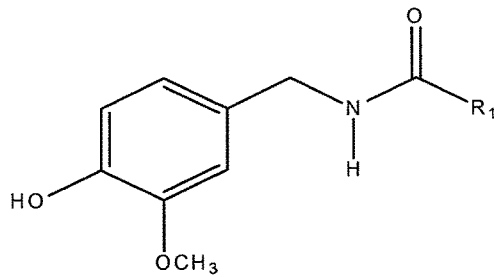

1. Capsaicin         R1 = (CH$_2$)$_4$(CH)$_2$CH(CH$_3$)$_2$

2. Homocapsaicin     R1 = (CH$_2$)$_5$(CH)$_2$CH(CH$_3$)$_2$

3. Nordihydrocapsaicin   R1 = (CH$_2$)$_5$CH(CH$_3$)$_2$
4. Dihydrocapsaicin      R1 = (CH$_2$)$_6$CH(CH$_3$)$_2$
5. Homodihydrocapsaicin  R1 = (CH$_2$)$_7$CH(CH$_3$)$_2$ 6. n-Vanillyloctanamide  R1 = (CH$_2$)$_6$CH$_3$
7. Nonivamide            R1 = (CH$_2$)$_7$CH$_3$
8. n-Vanillyldecanamide  R1 = (CH$_2$)$_8$CH$_3$

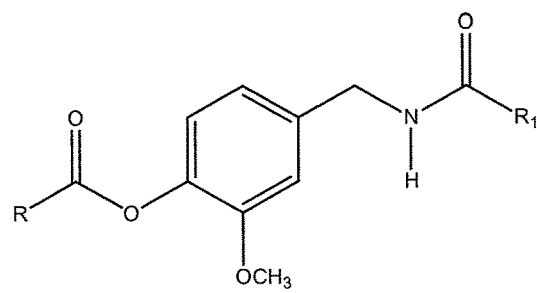

1. Capsaicin Ester       R1 = (CH$_2$)$_4$(CH)$_2$CH(CH$_3$)$_2$

2. Homocapsaicin Ester   R1 = (CH$_2$)$_5$(CH)$_2$CH(CH$_3$)$_2$

3. Nordihydrocapsaicin Ester   R1 = (CH$_2$)$_5$CH(CH$_3$)$_2$
4. Dihydrocapsaicin Ester      R1 = (CH$_2$)$_6$CH(CH$_3$)$_2$
5. Homodihydrocapsaicin Ester  R1 = (CH$_2$)$_7$CH(CH$_3$)$_2$ 6. n-Vanillyloctanamide Ester  R1 = (CH$_2$)$_6$CH$_3$
7. Nonivamide Ester            R1 = (CH$_2$)$_7$CH$_3$
8. n-Vanillyldecanamide Ester  R1 = (CH$_2$)$_8$CH$_3$

FIGURE 3.

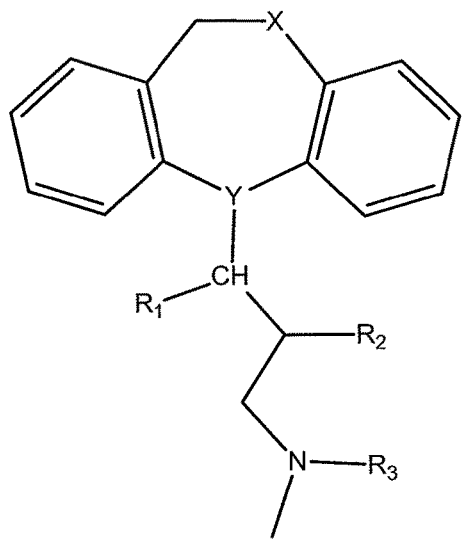
Amitriptyline   X = CH2; Y = C;   R1 = NONE; R2 = H; R3 = CH3
Butriptyline   X = CH2; Y = CH;   R1 = H; R2 = CH3; R3 = CH3
Trimipramine   X = CH2; Y = N;   R1 = H;   R2 = CH3; R3 = CH3
Dothiepin   X = S;   Y = C;   R1 = NONE; R2 = H; R3 = CH3
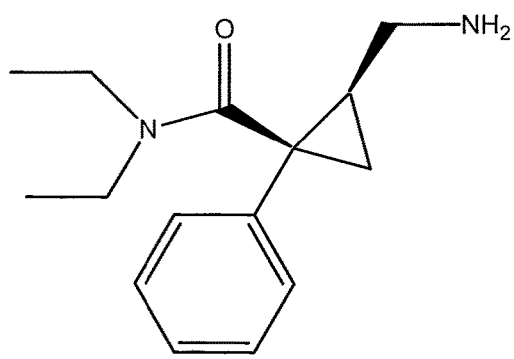
Milnacipran
FIGURE 4.

PHARMACEUTICAL COMPOSITIONS FOR TREATING CHRONIC PAIN AND PAIN ASSOCIATED WITH NEUROPATHY

This application is the United States national stage of International Application No. PCT/US2008/072360, filed Aug. 6, 2008, which was published under PCT Article 21 in English as International Publication No. WO 2009/021058, and which claims benefit of U.S. Provisional Patent Application No. 60/954,251 filed Aug. 6, 2007 and the text of application 60/954,251 is incorporated by reference in its entirety herewith.

BACKGROUND OF THE INVENTION

Chronic pain is a common problem that presents a major challenge to healthcare providers because of its complex natural history, unclear etiology, and poor response to therapy. Chronic pain is a poorly defined condition, and opinions vary regarding which duration qualifies a pain as chronic. Most clinicians consider ongoing pain lasting longer than 6 months as diagnostic, and others have used 3 months as the minimum criterion. In chronic pain, the duration parameter is used arbitrarily; some authors suggest that any pain that persists longer than the reasonable expected healing time for the involved tissues should be considered chronic pain. The pathophysiology of chronic pain is multifactorial and complex and still is poorly understood. Some have even suggested that chronic pain might be a learned behavioral syndrome that begins with a noxious stimulus that causes pain. Patients with several psychological syndromes (e.g., major depression, somatization disorder, hypochondriasis, conversion disorder) are prone to developing chronic pain. Pain is the most common complaint that leads patients to seek medical care, and chronic pain is not uncommon. Approximately 35% of Americans have some element of chronic pain, and approximately 50 million Americans are disabled partially or totally due to chronic pain.

Various neuromuscular, reproductive, gastrointestinal, and urologic disorders may cause or contribute to chronic pain. Sometimes multiple contributing factors may be present in a single patient. The modern concept of pain treatment emphasizes the significance of prophylactic prevention of pain, as pain is more easily prevented than it is relieved. Pain is generally controlled by the administration of short acting analgesic agents, steroids and non-steroidal anti-inflammatory drugs. Analgesic agents include opiates, agonistic-antagonistic agents, and anti-inflammatory agents.

A variety of therapeutics are available for the treatment of pain. As would be appreciated by one of skill, therapeutics vary in pharmacological profile and effectiveness, and a large number of compounds exist which may be used for the treatment of pain. Examples of dosages of individual compounds which have been administered for the treatment of pain are shown below in Table 1. Examples of a NMDA antagonist (dextromethorphan), atypical μ-opioid agonist (tramadol), and the anti-convulsant gabapentin, are shown below.

TABLE 1

Dosages for Partial Pain Relief

| Compound | Dose mg/day | Pain Relief (percent of reduction in pain) | |
|---|---|---|---|
| | | Diabetic Neuropathy | Fibromyalgia |
| Dextromethorphan Hydrobromide | 400-480 | <50 (Sang 2002) | <40 (Staud 2005) |
| Tramadol Hydrochloride | 400 | <35 (Sindrup 1999) | <30 (Biasi 1998; Russell 2000) |
| Gabapentin | 3600 | <50 (Marchettini 2004) | <50 (Lesley 2007) |

As shown above in Table 1, the above dosages were only effective in providing at most approximately a 35-50% reduction in pain. Unfortunately, several adverse side effects are associated with the drugs provided at the above dosages. These side effects include, e.g., dizziness, somnolence, and peripheral edema for gabapentin.

Harmful side effects are associated with most traditional analgesics at dosages effective for treating a neuropathy. As would be appreciated by one of skill, these side effects can include respiratory depression, disturbed sleep patterns, diminished appetite, seizures, and psychological and/or physical dependency. For example, the pharmacological management of acute postoperative pain and chronic pain syndromes has been traditionally based on various regimens of opiates and their congeners or NSAIDs. All opiates have side effects, of which the most dangerous are respiratory and cardiovascular depression associated with excessive sedation. NSAIDs may also induce side effects such as exacerbation of bleeding tendencies and the impairment renal function.

Accordingly, there is a need to provide methods and compositions for the treatment of acute or chronic pain which provide effective control of pain with reduced harmful side effects. Clearly, there is a need for improved compositions and methods for the effective treatment of neuropathic pain.

SUMMARY OF THE INVENTION

The present invention overcomes limitations in the prior art by providing improved methods and compositions for the treatment of pain. As described below, the inventor has discovered that the combination of low dosages of an NMDA antagonist (e.g., dextromethorphan), the atypical opioid tramamdol, and gabepentin demonstrate a clear synergy and can eliminate the majority of pain in patients with neuropathic pain who are refractory to traditional therapies. In certain embodiments, gabapentin may be substituted with a gabapentin analog such as pregabalin, and tramadol may be substituted with a tramadol analog. As shown in the below examples, these pharmaceutical compositions resulted in pain reduction with little or no toxicity and/or harmful side effects. Without wishing to be bound by any theory, it is believed that the low doses of the active agents used was responsible for the observed reduction or elimination of harmful side effects, as compared to traditional pain therapies. These present invention may be used to treat pain associated with, e.g., fibromyalgia syndrome, diabetic neuropathy, multiple sclerosis and/or cancer.

In certain aspects, the present invention relates to pharmaceutical compositions comprising tramadol, an NMDA antagonist, and a tricyclic antidepressant (e.g., amitriptyline). A combination of a non-toxic NMDA receptor antagonist such as dextromethorphan with tramadol or its analog and an anticonvulsant and/or a tricyclic anti-depressant exhibits significant palliative effects on chronic pain. Further it has been found in that such a combination can include a capsaicinoid (e.g., capsaicin) or an ester of capsaicin for added benefit.

It is a further object of the present invention to provide a method and a pharmaceutical formulation (medicament) for effectively treating patients in pain. Accordingly, the present invention provides a method that comprises administering a pharmaceutical composition comprising an analgesic combination that includes a NMDA receptor antagonist or a pharmaceutically acceptable salt thereof, an anticonvulsant and/or a tricyclic anti-depressant or a pharmaceutically acceptable salt thereof, and tramadol or its analog, or a pharmaceutically acceptable salt thereof. The pharmaceutical formulation can further contain capsaicin or an ester of capsaicin. By this method is achieved an analgesic preparation which produces prolonged and effective pain management, while at the same time exhibits reduced side effects and decreases the liability to dependence and tolerance which the patients may experience when subjected to prolonged treatment with an opiate.

In certain embodiments, the NMDA receptor antagonist can be dextromethorphan, dextrorphan, ketamine, amantadine, memantine, eliprodil, ifenprodil, phencyclidine, MK-801, dizocilpine, CCPene, flupirtine, or derivatives or salts thereof. The anticonvulsant can be, for example, gabapentin, pregabalin, 3-methyl gabapentin or derivatives thereof. Tramadol is typically a racemic mixture (1R,2R or 1S,2S)-(dimethylaminomethyl)-1-(3-methoxyphenyl)-cyclohexanol, although in certain embodiments enantiomerically purified or enantiomerically essentially pure active compounds of tramadol may be used. Tramadol analogs include its N-oxide derivative ("tramadol N-oxide"), its O-desmethyl derivative ("O-desmethyl tramadol"), venlafaxine, (R/S)-1-[2-(dimethylamino)-1-(4-methoxyphenyl) ethyl]cyclohexanol and O-desmethylvenlafaxine or mixtures, stereoisomers or recemates thereof. Capsaicinoids which may be used with the present invention include capsaicin, civamide, homocapsaicin, nordihydrocapsaicin, dihydrocapsaicin, homodihydrocapsaicin, n-vanillyloctanamide, nonivamide, n-vanillyldecanamide, cis-capsaicin, or derivatives thereof (e.g., see FIG. 3).

The term "ester derivatives of capsaicin" or "ester of capsaicin" in the present invention refers to the acylated derivatives of capsaicin and is denoted by the formula I below (e.g., see FIG. 3). These derivatives have a higher lipophilicity, lipid solubility and less irritation to the skin than the parent compound, and hence are better able to be incorporated into certain pharmaceutical formulations, including cream and ointment pharmaceutical formulations. Esterified capsaicinoids may be described by the formula:

R—CO—O₁CAP     (I)

wherein CAP refers to a capsaicinoid and O₁CAP refers to an oxygen present in an alcohol group of a corresponding non-esterified capsaicinoid. Various esterified capsaicinoids are described in US 2008/0020996 and U.S. Pat. No. 4,493,848 and U.S. Pat. No. 4,564,633, which are incorporated by reference in its entirety, and may be used with the present invention. Once administered to a subject, the esterified capsaicinoid may be enzymatically converted to the corresponding capsaicinoid once administered to a subject.

In formula I, R is selected from $C_{1-22}$ alkyl, $C_{6-22}$ aryl, $C_{1-22}$ alkylene, $C_{1-22}$ alkenyl, $C_{1-22}$ alkynyl and/or $C_{1-22}$ arylene. In various embodiments, the alkyl, alkylene, alkenyl, alkynyl and/or arylene may be $C_{1-18}$, $C_{1-12}$, or $C_{1-6}$. The aryl may be C≤22, C≤18, C≤12, or C=6. The alkyl, aryl and/or alkylene groups may be substituted or unsubstituted, branched or straight chains. In addition, R may contain heteroatoms and may be straight chained or branched.

The present invention further provides a method and composition for effectively treating patients in pain which avoids the toxicities associated with NSAID or acetaminophen therapy. The method comprises administering a pharmaceutical composition to a patient in need of treatment for pain, wherein the pharmaceutical composition comprises an analgesic combination comprising a NMDA antagonist or a pharmaceutically acceptable salt thereof, an anticonvulsant and/or a tricyclic anti-depressant or a pharmaceutically acceptable salt thereof, and tramadol or its analog, or a pharmaceutically acceptable salt thereof. The composition can further contain capsaicin or an ester of capsaicin.

In accordance with the present invention, the composition can be essentially free of a NSAID or acetaminophen. Particularly relevant NSAIDs include ibuprofen, diclofenac, diflunisal, etodolac, fenoprofen, flurbiprofen, indomethacin, ketoprofen, ketorolac, mefenamic acid, meclofenamate, nabumetone, naproxen, oxaprozin or piroxicam. If the patient is separately administered a NSAID and/or acetaminophen, the amount administered is preferably not enough to induce one or more toxicities associated with the use of the NSAID and/or acetaminophen.

Although tramadol/acetaminophen formulations containing a slew of other pharmaceutically active agents such as decongestants, antitussives, antihistamines or suspected adjuvants have been suggested in a general fashion, to the knowledge of the inventor, the particular combination of NMDA receptor antagonist, tramadol or its analog and anticonvulsant (e.g., gabapentin) and/or a tricyclic anti-depressant has not been previously recognized or appreciated. Similarly, to the knowledge of the inventor, the particular combination of NMDA receptor antagonist, tramadol or its analog, a capsaicinoid or esterified capsaicinoid and anticonvulsant and/or a tricyclic anti-depressant in a composition has not been recognized or appreciated. To the knowledge of the inventor, the particular combination of NMDA receptor antagonist, tramadol or its analog and anticonvulsant, optionally comprising a tricyclic anti-depressant and/or a capsaicinoid or esterified capsaicinoid in a composition essentially free of a NSAID and/or acetaminophen has not been recognized or appreciated.

In accordance with the present invention, the ratio of NMDA antagonist to tramadol or its analog can be from about 15:1 to 1:15, about 10:1 to 1:10, about 5:1 to 1:5, or about 1:2 to 1:2. The ratio of NMDA antagonist to anticonvulsant and/or a tricyclic anti-depressant to tramadol or its analog can be from about 90:1:1 to 1:90:1 to 1:1:90, preferably from about 10:1:1 to 1:10:1 to 1:1:10 and more preferably from 3:1:1 to 1:3:1 to 1:1:3. In a similar fashion, the ratio of NMDA antagonist to anticonvulsant and/or a tricyclic anti-depressant to tramadol or its analog to capsaicin or an ester of capsaicin can be from about 90:1:1:1 to 1:90:1:1 to 1:1:90:1 to 1:1:1:90 and preferably from about 10:1:1:1 to 1:10:1:1 to 1:1:10:1 to 1:1:1:10.

It is yet a further object to provide a method and pharmaceutical formulation (medicament) for the effective treatment of pain in patients by augmenting the analgesic effect of tramadol or its analog.

The invention is directed to the surprising and unexpected synergy obtained via the administration of a NMDA receptor antagonist together with an anticonvulsant (e.g., gabapentin)

and/or a tricyclic anti-depressant and tramadol or its analog. This synergy can be further augmented by the addition of capsaicin or an ester of capsaicin.

In certain embodiments, the invention relates to analgesic pharmaceutical compositions comprising a NMDA receptor antagonist together with an anticonvulsant and/or a tricyclic anti-depressant and tramadol or its analog. In other embodiments, the invention relates to analgesic pharmaceutical compositions comprising a NMDA receptor antagonist together with an anticonvulsant and/or a tricyclic anti-depressant, tramadol or its analog and capsaicin or an ester of capsaicin. The pharmaceutical compositions can be administered intravenously, intrathecally, orally, via a controlled release implant or pump, parenterally, sublingually, rectally, topically, via inhalation, etc. In other embodiments of the invention, tramadol or its analog can be administered separately from the NMDA receptor antagonist, capsaicin or an ester of capsaicin and the anticonvulsant and/or a tricyclic anti-depressant.

The invention allows for the use of lower doses of tramadol (or a tramadol analog) or a NMDA receptor antagonist, (referred to as apparent "one-way synergy" herein), or lower doses of both drugs (referred to as "two-way synergy" herein) than would normally be required when either drug is used alone. By using lower amounts of either or both drugs, the side effects associated with effective pain management in humans and other species are significantly reduced.

In certain preferred embodiments, the invention is directed in part to synergistic combinations of dextromethorphan or other NMDA receptor antagonist in an amount sufficient to render a therapeutic effect together with (1) gabapentin or a gabapentin analog and (2) tramadol or a tramadol analog, such that an analgesic effect is attained which is at least about 5 (and preferably at least about 10) times greater than that obtained with the dose of tramadol or its analog alone. This is exemplified by the apparent fact that patients with diabetic neuropathy and fibromyalgia, who could not get even 30-40% reduction in pain even with the administration of 400 mg of tramadol per day, can have shown 90-100% pain relief with a composition containing 35 mg of tramadol, 45 mg of dextromethorphan and 90 mg of gabapentin over a period of 12-16 hours. As shown in Table 2 below, a single active agent from this composition administered to a patient at the above dosage (i.e., 90 mg gabapentin only, 35 mg of tramadol only, or 45 mg of dextromethorphan) results in a pain reduction of less than 10%. In certain embodiments, the synergistic combination provides an analgesic effect which is up to about 30 to 40 times greater than that obtained with the dose of tramadol or its analog alone.

In certain embodiments, the combination synergizes to provide an analgesic effect which is up to about 10 to 20 times greater than that obtained with the dose of an anticonvulsant and/or a tricyclic anti-depressant if administered as a single agent. In such embodiments, the synergistic combinations display what is referred to herein as an "apparent mutual synergy", meaning that the dose of NMDA antagonist and anticonvulsant and/or a tricyclic anti-depressant synergistically potentiates the effect of tramadol or its analog and the dose of tramadol or its analog appears to potentiate the effect of the NMDA antagonist and the anticonvulsant and/or a tricyclic anti-depressant.

The combination of NMDA antagonist, anticonvulsant and/or a tricyclic anti-depressant and tramadol or its analog can be administered in a single dosage form. Similarly, the combination of NMDA antagonist, anticonvulsant and/or a tricyclic anti-depressant, capsaicin or an ester of capsaicin and tramadol or its analog can be administered in a single dosage form. The combination can be administered separately or concomitantly.

In certain embodiments, the synergism is exhibited between the three types of drugs using dosages of tramadol or its analog would be sub-therapeutic if administered without the dosage of the NMDA antagonist and anticonvulsant. This synergy can be further augmented by the addition of a fourth drug, such as a tricyclic antidepressant, capsaicin, or an ester of capsaicin. Similarly, in certain preferred embodiments wherein the pharmaceutical composition comprises a combination of NMDA antagonist, anticonvulsant and/or a tricyclic anti-depressant and tramadol or its analog and is essentially free of a NSAID or acetaminophen, the dosage of tramadol or its analog would be sub-therapeutic if administered without the dosage of the NMDA antagonist and anticonvulsant and/or a tricyclic anti-depressant. In other preferred embodiments, the present invention relates to a pharmaceutical composition comprising an analgesically effective dose of tramadol or its analog together with a dose of a NMDA antagonist and an anticonvulsant and/or a tricyclic anti-depressant effective to augment the analgesic effect of tramadol or its analog, or a composition essentially free of a NSAID or acetaminophen and comprising an analgesically effective dose of tramadol or its analog together with a dose of a NMDA antagonist effective to augment the analgesic effect of tramadol or its analog Without wishing to be bound by any theory, it is believed that these combinations exhibit two-way synergism, meaning that the NMDA antagonist and the anticonvulsant potentiates the effect of tramadol (or a tramadol analog), and tramadol (or the tramadol analog) potentiates the effect of the NMDA antagonist and the anticonvulsant. This synergy may be further augmented by the addition of a fourth drug, such as a tricyclic antidepressant, a capsaicinoid or an esterified capsaicinoid.

In other aspects, the invention relates to pharmaceutical compositions comprising an NMDA antagonist, an anticonvulsant (e.g., gabapentin or a gabapentin analog), tramadol or a tramadol analog, and/or a tricyclic anti-depressant where the dose of each drug is reduced due to the synergism demonstrated between the drugs, and the analgesia derived from the combination of drugs in reduced doses is significantly or synergistically enhanced. The dose of one or more or all of the NMDA antagonist, an anticonvulsant (e.g., gabapentin or a gabapentin analog), tramadol or a tramadol analog, and/or a tricyclic anti-depressant may be present in the pharmaceutical composition at a sub-therapeutic dose if administered individually. In other embodiments, the dosage of one or more or all of the NMDA antagonist, the gabapentin or gabapentin analog, and tramadol or tramadol analog, if administered individually, result in about 10-30%, or about 10-20% or less than about 10% of the therapeutic effect of the combined agents. The dose of tramadol may be less than 400 mg, from about 30 to about 400 mg, or from about 30 to about 50 mg.

In further aspects, the present invention relates to a method of using a pharmaceutical combination in the treatment of pain, especially for treatment of chronic pain disorders. Such disorders include, but are not limited to, inflammatory pain, postoperative pain, osteoarthritis, pain associated with metastatic cancer, trigeminal neuralgia, acute herpetic and postherpetic neuralgia, diabetic neuropathy, causalgia, brachial plexus avulsion, occipital neuralgia, reflex sympathetic dystrophy, fibromyalgia, gout, phantom limb pain, burn pain, and other forms of neuralgic, neuropathic, and idiopathic pain syndromes.

In certain preferred embodiments, the doses of the NMDA antagonist, anticonvulsant and/or a tricyclic anti-depressant and tramadol or its analog are administered orally. In further preferred embodiments the doses of the NMDA antagonist, anticonvulsant and/or a tricyclic anti-depressant and tramadol or its analog are administered in a single oral dosage form. In certain preferred embodiments, the dose of tramadol or its analog would be sub-therapeutic if administered without the dose of the NMDA antagonist and the anticonvulsant and/or a tricyclic anti-depressant. In other preferred embodiments, the dose of tramadol or tramadol analog is effective to provide analgesia alone, but the dose of tramadol or its analog provides at least a five fold greater analgesic effect than typically obtained with that dose of tramadol or its analog alone.

In yet other aspects, the invention relates to the use of a NMDA antagonist in the manufacture of a pharmaceutical preparation containing a NMDA antagonist, an gabapentin (or a gabapentin analog) and tramadol (or a tramadol analog) for the treatment of pain. The pharmaceutical preparation may further comprise a capsaicinoid or an esterified capsaicinoid and/or a tricyclic antidepressant.

The invention further relates to the use of a tramadol or its analog in the manufacture of a pharmaceutical preparation containing a NMDA antagonist, an anticonvulsant and/or a tricyclic anti-depressant, and tramadol or its analog for the treatment of pain of chronic, intermittent or acute nature. Similarly, the invention further relates to the use of a tramadol or its analog in the manufacture of a pharmaceutical preparation containing a NMDA antagonist, an anticonvulsant and/or a tricyclic anti-depressant, capsaicin or an ester of capsaicin and tramadol or its analog for the treatment of pain of chronic, intermittent or acute nature.

The invention further relates to the use of an anticonvulsant and/or a tricyclic anti-depressant in the manufacture of a pharmaceutical preparation containing a NMDA antagonist, an anticonvulsant and/or a tricyclic anti-depressant and tramadol or its analog for the treatment of pain of chronic, intermittent or acute nature. Similarly, the invention further relates to the use of an anticonvulsant and/or a tricyclic anti-depressant in the manufacture of a pharmaceutical preparation containing a NMDA antagonist, an anticonvulsant and/or a tricyclic anti-depressant, capsaicin or an ester of capsaicin and tramadol or its analog for the treatment of pain of chronic, intermittent or acute nature.

The invention further relates to the use of capsaicin or an ester of capsaicin in the manufacture of a pharmaceutical preparation containing a NMDA antagonist, an anticonvulsant and/or a tricyclic anti-depressant, capsaicin or an ester of capsaicin and tramadol or its analog for the treatment of pain of chronic, intermittent or acute nature.

The invention is also directed to a method for providing effective pain management in humans, comprising administration of either an analgesically effective or sub-therapeutic amount of a tramadol or its analog, administration of an effective amount of an anticonvulsant and/or a tricyclic anti-depressant in an amount effective to augment synergistically the analgesic effect provided by said tramadol or its analog, and administration of an effective amount of a NMDA antagonist such as dextromethorphan in an amount effective to augment synergistically the analgesic effect provided by said tramadol or its analog. The NMDA antagonist and anticonvulsant and/or a tricyclic anti-depressant can be administered prior to, concurrently with, or after administration of tramadol or its analog, as long as the dosing interval of NMDA antagonist overlaps with the dosing interval of tramadol or its analog and/or its analgesic effects.

The invention is also directed to a method for providing effective pain management in humans, comprising administration of either an analgesically effective or sub-therapeutic amount of a tramadol or its analog, administration of an effective amount of an anticonvulsant and/or a tricyclic anti-depressant in an amount effective to augment synergistically the analgesic effect provided by said tramadol or its analog, administration of an effective amount of capsaicin or an ester of capsaicin in an amount effective to augment synergistically the analgesic effect provided by said tramadol or its analog and administration of an effective amount of a NMDA antagonist such as dextromethorphan in an amount effective to augment synergistically the analgesic effect provided by said tramadol or its analog. The NMDA antagonist, capsaicin or an ester of capsaicin and anticonvulsant and/or a tricyclic anti-depressant can be administered prior to, concurrently with, or after administration of tramadol or its analog, as long as the dosing interval of NMDA antagonist, capsaicin or an ester of capsaicin and anticonvulsant and/or a tricyclic anti-depressant overlaps with the dosing interval of tramadol or its analog and/or its analgesic effects.

The anticonvulsant and/or a tricyclic anti-depressant can be administered prior to, concurrently with, or after administration of tramadol or its analog and a NMDA antagonist, as long as the dosing interval of the anticonvulsant and/or a tricyclic anti-depressant and a NMDA antagonist overlaps with the dosing interval of tramadol or its analog and/or its analgesic effects. In certain embodiments, the NMDA antagonist and the anticonvulsant and/or a tricyclic anti-depressant need not be administered in the same dosage form or even by the same route of administration as tramadol or its analog. In certain embodiments, the method may comprise inducing synergistic and/or additive analgesic benefits obtained in humans or other mammals, when an analgesically effective amount of tramadol or a tramadol analog is administered to a human or other mammals, and, prior to or during the dosage interval for tramadol or its analog or while the human or other mammal is experiencing analgesia, an effective amount of NMDA antagonist and anticonvulsant and/or a tricyclic anti-depressant to augment the analgesic effect of tramadol or its analog is administered. If the NMDA antagonist and the anticonvulsant and/or a tricyclic anti-depressant are administered prior to the administration of tramadol or its analog, it is preferred that the dosage intervals for the two drugs overlap, i.e., such that the analgesic effect over at least a portion of the dosage interval of tramadol or its analog is at least partly coincident with the period of useful therapeutic effect of the NMDA antagonist and the anticonvulsant and/or a tricyclic anti-depressant. Similarly, if the NMDA antagonist, capsaicin or an ester of capsaicin and the anticonvulsant and/or a tricyclic anti-depressant are administered prior to the administration of tramadol or its analog, it is preferred that the dosage intervals for the three drugs overlap, i.e., such that the analgesic effect over at least a portion of the dosage interval of tramadol or its analog is at least partly coincident with the period of useful therapeutic effect of the NMDA antagonist, capsaicin or an ester of capsaicin and the anticonvulsant and/or a tricyclic anti-depressant.

In further embodiments, synergistic or at least additive benefits obtained in humans are achieved when analgesically effective levels of a tramadol or its analog have been administered to a human during the time period of the therapeutic effect of a NMDA antagonist and an anticonvulsant and/or a tricyclic anti-depressant. Similarly, the surprising synergistic and/or additive benefits obtained in humans are achieved when analgesically effective levels of a tramadol or its analog have been administered to a human during the time period of the therapeutic effect of a NMDA antagonist, capsaicin or an ester of capsaicin and an anticonvulsant and/or a tricyclic anti-depressant. Alternatively the method may comprise inducing analgesia in a human or other mammal is experiencing analgesia by administering a NMDA antagonist, capsaicin or an ester of capsaicin and an anticonvulsant and/or a tricyclic anti-depressant and an effective amount of a tramadol or its analog to the human or other animal to augment the analgesic effect of tramadol or its analog.

In a further embodiment of the present invention, the invention comprises an oral solid dosage form comprising an analgesically effective amount of tramadol or its analog together with an amount of a NMDA antagonist and an anticonvulsant and/or a tricyclic anti-depressant which augment the effect of tramadol or its analog. Yet in a further embodiment of the present invention, the invention comprises an oral solid dosage form comprising an analgesically effective amount of tramadol or its analog together with an amount of a NMDA antagonist, capsaicin or an ester of capsaicin and an anticonvulsant and/or a tricyclic anti-depressant which augment the effect of tramadol or its analog.

Optionally, the oral solid dosage form includes a sustained release carrier that effectuates the sustained release of tramadol or its analog, or both the tramadol or its analog and the NMDA antagonist when the dosage form contacts gastrointestinal fluid. The sustained release dosage form may comprise a multiplicity of substrates and carriers that include the drugs. The substrates may comprise matrix spheroids or may comprise inert pharmaceutically acceptable beads that are coated with the drugs. The coated beads may then be overcoated with a sustained release coating comprising the sustained release carrier. The matrix spheroid may include the sustained release carrier in the matrix itself, or the matrix may comprise a simple disintegrating or prompt release matrix containing the drugs, the matrix having a coating applied thereon which comprises the sustained release carrier. In yet other embodiments, the oral solid dosage form comprises a tablet core containing the drugs within a normal or prompt release matrix with the tablet core being coated with a sustained release coating comprising the sustained release carrier.

In various embodiments, the tablet or capsule contain the drugs within a sustained release matrix comprising the sustained release carrier. The tablet may contain tramadol or its analog within a sustained release matrix, and the NMDA antagonist and anticonvulsant and/or a tricyclic anti-depressant coated into the tablet as an immediate release layer. The tablet may contain tramadol or its analog within a sustained release matrix, and the NMDA antagonist, capsaicin or an ester of capsaicin and anticonvulsant and/or a tricyclic anti-depressant coated into the tablet as an immediate release layer.

In certain preferred embodiments, the pharmaceutical compositions containing the NMDA antagonist, an anticonvulsant and/or a tricyclic anti-depressant and tramadol or its analog set forth herein are administered orally. Such oral dosage forms may contain one or all of the drugs in immediate or sustained release form. For ease of administration, it is preferred that the oral dosage form contains all the three drugs. The oral dosage forms may be in the form of tablets, troches, lozenges, aqueous, solid or semi-solid solutions or mixtures, or oily suspensions or solutions, dispersible powders or granules, emulsions, multiparticulate formulations, syrups, elixirs, and the like.

In other embodiments, a pharmaceutical composition containing the NMDA antagonist, anticonvulsant and/or a tricyclic anti-depressant and tramadol or its analog can be administered in dosage form as a topical preparation, a solid state and or depot type transdermal delivery device(s), a suppository, a buccal tablet, or an inhalation formulation such as a controlled release particle formulation or spray, mist or other topical vehicle, intended to be inhaled or instilled into the sinuses. Similarly, in other embodiments, a pharmaceutical composition containing the NMDA antagonist, anticonvulsant and/or a tricyclic anti-depressant, capsaicin or an ester of capsaicin and tramadol or its analog can be administered in dosage form as a topical preparation, a solid state and or depot type transdermal delivery device(s), a suppository, a buccal tablet, or an inhalation formulation such as a controlled release particle formulation or spray, mist or other topical vehicle, intended to be inhaled or instilled into the sinuses.

The pharmaceutical compositions containing the NMDA antagonist, anticonvulsant and/or a tricyclic anti-depressant and/or tramadol or its analog set forth herein may alternatively be in the form of microparticles such as microcapsules, microspheres and the like, which may be injected or implanted into a human patient, or other implantable dosage forms known to those skilled in the art of pharmaceutical formulation. Similarly, the pharmaceutical compositions containing the NMDA antagonist, capsaicin or an ester of capsaicin, anticonvulsant and/or a tricyclic anti-depressant and/or tramadol or its analog set forth herein may alternatively be in the form of microparticles such as microcapsules, microspheres and the like, which may be injected or implanted into a human patient, or other implantable dosage forms known to those skilled in the art of pharmaceutical formulation. The dosage forms may contain each active drug for ease of administration.

Similarly, pharmaceutical compositions essentially free of a NSAID or acetaminophen and comprising a combination of a NMDA antagonist, an anticonvulsant and/or a tricyclic anti-depressant and a tramadol or its analog may be prepared in solid oral dosage forms or other dosage forms. Accordingly, the pharmaceutical compositions can be administered orally, by means of an implant, parenterally, sub-dermally, sublingually, rectally, topically, or via inhalation.

Another embodiment of the invention is directed to a method of alleviating pain without the use of a narcotic analgesic. The method comprises administering to a patient a pharmaceutical composition comprising a NMDA antagonist, an anticonvulsant and/or a tricyclic anti-depressant and tramadol or its analog, or comprising a pharmaceutical composition essentially free of a NSAID or acetaminophen and comprising a combination of a NMDA antagonist, an anticonvulsant and/or a tricyclic anti-depressant and tramadol or its analog. The active agents may be administered either together or separately, wherein the patient is not administered a narcotic analgesic.

In addition, the present invention can avoid the liability of gastrointestinal and liver toxicity by omitting acetaminophen, aspirin and other NSAID's. Acetaminophen toxicity is well known and represents a significant drawback of all formulations that contain it. The limiting dose of acetaminophen is on the order of 2 grams per day. It has also been determined that intentional overdose of acetaminophen is the second most common method of committing suicide in Europe. Thus, reducing or eliminating exposure to acetaminophen is of significant importance.

In further aspects, the invention relates to a method of alleviating pain without the use of a narcotic analgesic. The method may comprise administering to a patient a NMDA antagonist, tramadol or a tramadol analog, and an anticonvulsant (e.g., gabapentin or a gabapentin analog), wherein the patient is not administered a narcotic analgesic. A tricyclic anti-depressant, a capsaicinoid or an esterified capsaicinoid may also be administered to the patient. The active agents may be comprised in a pharmaceutical composition, and the pharmaceutical preparation may be free or essentially free of a NSAID or acetaminophen. The active agents may be administered either together or separately.

The terms "inhibiting," "reducing," or "prevention," or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions of the invention can be used to achieve methods of the invention.

Throughout this application, the term "about" is used to indicate that a value includes the inherent variation of error for the device, the method being employed to determine the value, or the variation that exists among the study subjects.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 provides the chemical structures of certain compounds which can be used in practicing the present invention.

FIG. 3 provides chemical structures of certain capsaicin analogs and their esters.

FIG. 4 provides chemical structures of certain cyclic anti-depressant.

DESCRIPTION OF ILLUSTRATIVE EMBODIMENTS

Figure 2:
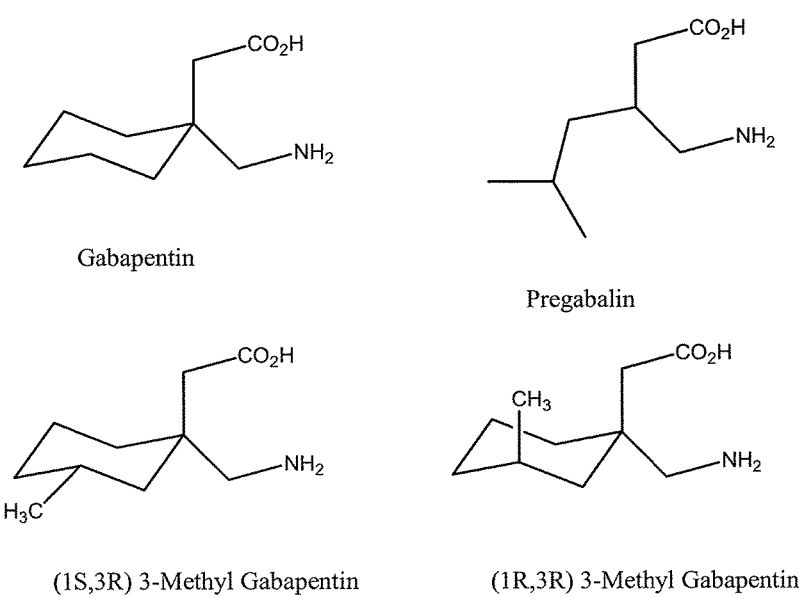
FIG. 2 provides the chemical structures of certain gabapentin analogs.

The present invention overcomes limitations in the prior art by providing improved methods and compositions for the treatment of pain. As described in further detail below, the inventor has discovered that the combination of low dosages of an NMDA antagonist (e.g., dextromethorphan), the atypical μ-opiate agonist tramadol, and gabepentin demonstrate a clear synergy and can result in a clear reduction of the majority of pain in patients with neuropathic pain who are refractory to traditional therapies. As shown in the below examples, these pharmaceutical compositions resulted in little or no toxicity and/or harmful side effects. Without wishing to be bound by any theory, it is believed that the low doses of the active agents was responsible for this reduction in side effects as compared to traditional pain therapies.

For example, the synergistic effect of the combination can further be appreciated in Table 1 below. As shown in Table 1, the administration of TLI-1026 (tramadol 35 mg plus 35 mg dextromethorphan plus 90 mg gabapentin) twice daily, reduces the pain in fibromyalgia and diabetic neuropathy patients by almost 95% while these individual components at these doses have very little effect on the pain (i.e., less than about a 10% reduction). Further, as shown below, administration of much higher dosages of these same drugs administered individually fail to achieve the same level pain relief as compared to the combination of the lower doses of the active agents; specifically, although the dosages of the individually administered agents are approximately an order of magnitude higher, the pain was reduced by only at most 30%-50%. In contrast, while a pain reduction of about 95% was observed for the combination of the lower doses of the agents (TLI-1026).

TABLE 2

The Synergistic Effect of the Combination Therapy

| | | Pain Relief (percent of reduction in pain) | |
|---|---|---|---|
| Compound | Dose mg/day | Diabetic Neuropathy | Fibromyalgia |
| Dextromethorphan Hydrobromide | 400-480 (Sang 2002) | <50 | <40 (Staud 2005) |
| Tramadol Hydrochloride | 400 (Sindrup 1999) | <35 | <30 (Biasi 1998; Russell 2000) |
| Gabapentin | 3600 | <50 (Marchettini 2004) | <50 (Lesley 2007) |
| TLI-1026* | | 95 (N = 5) | 95 (N = 5) |
| Dextromethorphan (present as Hydrochloride) | 70 | <10 | <10 |

TABLE 2-continued

The Synergistic Effect of the Combination Therapy

| Compound | Dose mg/day | Pain Relief (percent of reduction in pain) | |
|---|---|---|---|
| | | Diabetic Neuropathy | Fibromyalgia |
| Tramadol (present as Hydrochloride) | 70 | <10 | <10 |
| Gabapentin | 180 | <10 | <10 |

*TLI-1026 contains (35 mg tramadol, 35 mg dextromethorphan, and 90 mg gabapentin) and was administered twice daily.

A. Definition of Terms

It should be understood that for purposes of the present invention, the following terms have the following meanings:

The term "effective analgesia" is defined for purposes of the present invention as a satisfactory reduction in or elimination of pain, along with the production of a tolerable level of side effects, as determined by the human patient.

The term "effective pain management" is defined for the purposes of the present invention as the objective evaluation or opinion of a human patient's response (pain experienced versus side effects) to analgesic treatment by a physician as well as subjective evaluation of therapeutic treatment by the patient undergoing such treatment. The skilled artisan will understand that effective analgesia will vary widely according to many factors, including individual patient variables.

The term "tramadol or its analog" is defined for purposes of the present invention as the drug in its base form, or a pharmaceutically acceptable salt or complex thereof. Even though it is known that the pure enantiomers of tramadol have a differing pharmaceutical profiles and effects when compared to the racemate as discussed in the background of the invention, it should be understood for the purpose of the invention, both the optical isomers and the recemic mixtures of tramadol will be referred simply as "tramadol or its analog".

The term "dextromethorphan" is defined for purposes of the present invention as the drug in its base form, or a pharmaceutically acceptable salt or complex thereof.

The term "anticonvulsant" as used herein is intended to encompass compounds which possess anti-epileptic activity and some of them bind to the family of proteins called $\alpha_2\delta$. Examples of such compound include, but not limited to, sodium channel blockers such as carbamazepine, phenyloin, oxcarbazepine, lamotrigine and zonisamide, benzodiazepine analogs, valproate, glutamate blockers such as felbamate and topiramate, levetiracetam, gabapentin, derivatives or analogs of gabapentin or any compounded mixture thereof (see FIG. 2). Examples of gabapentin analogs include, but not limited to, pregabalin, 3-methyl-gabapentin, [(1R,5R,6S)-6-(Aminomethyl)bicyclo[-3.2.0]hept-6-yl]acetic acid, 3-(1-Aminomethyl-cyclohexylmethyl)-4H-[1,2,4]-oxadiazol-5-one, C-[1-(1H-Tetrazol-5-ylmethyl)-cycloheptyl]-methylamine, (3S,4S)-(1-Aminomethyl-3,4-dimethyl-cyclopentyl)-acetic acid, (1α,3α,5α)(3-amino-methyl-bicyclo[3.2.0]hept-3-yl)-acetic acid, (3S,5R)-3-Aminomethyl-5-methyl-octanoic acid, (3S,5R)-3-amino-5-methyl-heptanoic acid, (3S,5R)-3-amino-5-methyl-nonanoic acid and (3S,5R)-3-amino-5-methyl-octanoic acid, or a pharmaceutically acceptable salt thereof.

The term "tricyclic anti-depressant" (abbreviation TCA) as used herein is intended to encompass a class of anti-depressant drugs and these drugs are named after their molecular structures, which contain three rings of atoms (See FIG. 4). Prominent among the tricyclic anti-depressants are the linear tricyclics, e.g., imipramine, desipramine, amitriptyline, nortriptyline, protriptyline, doxepin, ketipramine, mianserin, dothiepin, amoxapine, dibenzepin, melitracen, maprotiline, flupentixol, azaphen, tianeptine and related compounds showing similar activity. Angular tricyclics include indriline, clodazone, nomifensin, and related compounds. A variety of other structurally diverse anti-depressants, e.g., iprindole, wellbatrin, nialamide, milnacipran, phenelzine and tranylcypromine have been shown to produce similar activities (Sellinger et al, 1979; Pandey et al, 1979; and Moret et al, 1985). They are functionally equivalent to the tricyclic anti-depressants and are therefore included within the scope of the invention. Thus, the term tricyclic anti-depressant is intended by the present inventor to embrace the broad class of anti-depressants described above together with related compounds sharing the common property that they all possess anti-depressant activity.

The term "an anticonvulsant and/or a tricyclic anti-depressant" as used herein is intended to encompass either a combination of an anticonvulsant and a tricyclic anti-depressant or an anticonvulsant alone or a tricyclic anti-depressant alone.

The term "chronic pain" means pain associated with an idiopathic or undiagnosed or an undiagnosible disease, disorder or condition, or pain associated with any one of: myofascial pain syndrome, trigger points, tender points, thorasic outlet syndrome, complex regional pain syndrome, reflex sympathetic dystrophy (RSD), sympathetically maintained pain (SMP), diabetic neuropathy syndrome (DNS); chronic pain associated with fibromyalgia syndrome (FMS), multiple sclerosis (MS); chronic pain associated with traumatic injury to the peripheral nervous system; chronic pain resulting from herpes zoster (also known as shingles, or post-herpetic neuropathy) or similar infections that attack and damage nerve fibers or endings; post-operative pain, which arises after surgery and then lingers far beyond a normal convalescent period; pain associated with nerve and root damage, such as pain associated with peripheral nerve disorders, including, nerve entrapment and brachial plexus avulsions, amputation, peripheral neuropathies, tic douloureux, atypical facial pain, nerve root damage, and arachnoiditis syndrome, in which an amputee suffers from feelings of pain or discomfort that seems to originate in the missing limb ("phantom limb" pain); pain associated with carcinoma, often referred to as cancer pain; neuropathic pain associated with chemotherapy treatment; central nervous system pain, including pain due to spinal cord or brain stem damage; low back pain; sciatica; headache, including migraine, chronic tension headache, cluster headache, temporomandibular disorder (TMJ) pain and maxillary sinus pain; complex regional pain syndromes, including reflex sympathetic dystrophy and causalgia, or from burn injury; the chronic pain associated with hyperesthesia, allodynia, hyperalgesia, deafferentation pain, sympathetically maintained pain, non-nociceptive chronic pain.

The term "pain relieving" is generally defined herein to include the expressions "pain-suppressing", "pain-reducing", and "pain-inhibiting" as the invention is applicable to the alleviation of existing pain, as well as the suppression or inhibition of pain which would otherwise ensue from the imminent pain-causing event.

The term "sustained or controlled release" is defined for purposes of the present invention as the release of the drug (tramadol or its analog) from the transdermal formulation at such a rate that blood (plasma) concentrations (levels) of the drugs are maintained within the therapeutic range that is above the minimum effective analgesic concentration or "MEAC", but below toxic levels over a period of time of several hours to several days.

The term "steady state" means that the blood plasma time/concentration curve for a given drug level has been substantially stable within a set range from dose to dose.

The term "minimum effective analgesic concentration" or "MEAC" is defined for purposes of this invention as the minimum effective therapeutic blood plasma level of the drug at which at least some pain relief is achieved in a given patient. It will be well understood by those skilled in the medical art that pain measurement is highly subjective and great individual variations may occur among patients.

The term "capsaicinoid" or "capsaicins" as used herein is intended to encompass not only the compound capsaicin, but also homocapsaicin, nordihydrocapsaicin, dihydrocapsaicin, homodihydrocapsaicin or any compounded mixture thereof (see FIG. 3).

It must be noted that, as used in this specification, the singular forms "a," "an" and "the" include plural referents unless the context clearly dictates otherwise. Thus, for example, reference to "a pharmacologically active agent" includes a combination of two or more pharmacologically active agents, and the like.

As used herein in the claim(s), when used in conjunction with the word "comprising", the words "a" or "an" may mean one or more than one. As used herein "another" may mean at least a second or more.

B. NMDA Antagonists

The search for alternative pain control strategies has focused on the N-methyl-D-aspartate (NMDA) receptors and their antagonists which were recently shown to reduce somatic and neuropathic pain sensation in both animal and human models (Plesan et al, 1998, Klepstad et al, 1990, Eisenberg et al, 1998, Kinnman et al, 1997 and Kawamatugs to a et al, 1998). The clinical utility of these agents stems from the high affinity binding of the drugs to NMDA receptors resulting in blockade of the NMDA receptors located at the junction where pain is generated by peripheral nociceptive stimuli and is thence conveyed to central receptors via A* and C sensory fibers (Woolf et al, 1993). From a clinical standpoint, the amounts of conventional pain killers that are needed for effective pain control would be much smaller. One of these compounds is dextromethorphan (DM), a low affinity, non-competitive NMDA receptor antagonist that has a long history of clinical safety as a cough suppressant (Bem et al, 1992).

Considerable evidence has accumulated over the past few years on the role of excitatory amino acids (EAA), such as glutamate and aspartate, in modulating the sensation of pain via the ascending pathways along the spinal cord and central nervous system. The stimulation of NMDA receptors located in the dorsal horn of the spinal cord, the area responsible for relaying, modulating and transmitting pain, by intraspinal deposition of glutamate in experimental rat and monkey models generated an increased response to noxious stimuli and lowered the threshold of pain (Battaglia et al, 1988; Aanonsen et. al. 1987). This response was successfully abolished by administration of NMDA antagonists, such as phencyclidine, suggesting that the pain can be attenuated by blocking the activity of these receptors.

Investigations of chronic pain syndromes revealed that the same mechanisms are involved in the initiation and the perpetuation of secondary pain in mouse and rat models. In terms of neurophysiology, following acute tissue injury, transduction is accomplished by action potentials being generated at the nerve endings and transmitted along the A* and C fibers to the synapses of the dorsal part of the spinal cord where they induce the release of various peptides, including EAA. The EAA activate the NMDA receptors that are located within the synapses, thus stimulating the synaptic neurons to transmit sensations of pain. This state of hyperexcitability, or "wind up" amplifies the magnitude and duration of neurogenic responses to any existing volley of nociceptive activity. Once initiated, this state of hyperexcitability can exist even after the peripheral input has ceased Dickenson 1995). This phenomenon is currently thought to be responsible for various clinical pain syndromes such as allodynia, an intense sensation of pain following a relatively minor stimulus that would not ordinarily induce pain sensation or hyperpathia, a sensation of pain that persists long after the initial nociceptive stimulus has subsided (Davies et al, 1987; Felsby et al, 1995).

The role of NMDA in the "wind up" phenomenon of pain perception was clarified in animals by intraspinal administration of NMDA-receptor antagonists (Dickenson 1990; Dickenson et al, 1990). In one human study, i.v. ketamine reduced the magnitude of both primary (immediate) and secondary hyperalgesia and the pain evoked by prolonged heat stimulation in a dose-dependent manner (Ilkjaer et al, 1996). DM acts in a similar manner: Klepstad et al, published a case report of a patient who had undergone four years of satisfactory ketamine treatment for postherpetic neuralgia. Experimental substitution of the ketamine by DM 125 mg in four divided doses for seven days was found to be as efficient. Here it is important to note that the NMDA receptors are widespread throughout the central nervous system, and as such, are associated with highly diverse neurophysiological functions as far removed from the modulation of pain as learning and memory processing.

It is therefore not surprising that NMDA antagonists can interfere with certain physiological activities, leading to sedation, motor dysfunction or altered behavior. Antagonism of the potentially deleterious effects of an excessive release of EAA, such as that which occurs in patients with focal brain ischemia (an example of the diversity of NMDA activity) can lead to episodes of agitation, hallucinations, somnolence, nausea, vomiting and nystagmus (Grotta et al, 1995, Albers et al, 1995, Muir et al, 1995). This is why so few NMDA receptor antagonists have been tested in humans despite their effectiveness in pain management, and despite the extensive animal data that point to their promising beneficial effect (Roytblat et al, 1993, Mercadante et al, 1996, Kornhuber et al, 1995).

To date DM, ketamine and amantadine are the only drugs with NMDA receptor antagonistic properties that are FDA approved drugs for clinical use. However, due to the high affinity of ketamine to its receptors and its related dysphoric effects, together with the need to administer it intravenously, research in pain control has turned its focus to DM as the preferred NMDA antagonist for clinical use.

1. Dextromethorphan

Dextromethorphan (DM) and levorphanol were originally synthesized as pharmacological alternatives to morphine more than 40 years ago. DM is the D isomer of the codeine analogue, levorphanol but, in contrast to its L isomer, it has no effect on the opiate receptors (Benson et al, 1953). From the beginning, its clinical use was mainly that of an antitussive in syrup preparations, at adult doses of 10 to 30 mg three to six times daily. The specific central sites upon which DM exerts its antitussive effect are still uncertain, but they are distinct from those of opiates, insofar as the effect is not suppressed by naloxone (Karlsson et al, 1988). Also, unlike opiates, DM has an established safety record, i.e., the therapeutic cough suppressant dose (1 mg·kg$^{-1}$·dy$^{-1}$) has no major opiate like respiratory or hemodynamic side effects, neither does it induce histamine release complications. The binding of the antagonists to the NMDA receptors results in modifying the receptor-gated Ca$^{2+}$ current. Changes in the Ca$^{2+}$ current normally lead to NMDA induced neuronal firing which, if it persists, is followed by a heightening of the intensity of the primary nociceptive stimulus, i.e., "wind up" phenomenon, and the triggering of secondary sensory pain (Mendell 1966; Church et al, 1985). In contrast to the other NMDA receptor antagonists, DM has widespread binding sites in the central nervous system that are distinct from those of opiates and other neurotransmitters, so that its activity is not limited to the NMDA receptors alone, as was shown in pigs and rats (Musacchio 1988, Church 1991). Besides the ability of DM to reduce intracellular Ca$^{2+}$ influx through the NMDA receptor-gated channels, DM also regulates voltage-gated Ca$^{2+}$ channels that are normally activated by high concentrations of extracellular K$^+$. One of the physiological consequences of these multi-channel regulation capabilities is the attenuation by DM of NMDA mediated neuronal firing in the brain that is normally transformed into seizures, as was shown experimentally in rats and in neuronal cell cultures as well as in humans (Ferkany 1988, Choi 1987).

The neuropharmacological cascade of events that provokes the reduced intracellular accumulation of Ca$^{2+}$ to cause changes in the activity of NMDA receptors remains to be elucidated. In humans as in animals, DM was also capable of ameliorating discomfort associated with excitotoxicity-related neurological disorders, such as intractable seizures and Parkinson's disease when administered at doses of 30 or 60 mg q.i.d. (Albers 1991), 45 to 180 mg p.o. (Bonuccelli et al, 1991) or 120 mg p.o. (Fisher et al, 1990) for periods of three weeks to three months. No serious untoward neurological effects were detected in these and in another study where eight healthy human volunteers in whom motor cortex excitability, as indicated by motor-evoked potentials, was reduced after a single oral high (150 mg) dose (Ziemann et al, 1998). In addition, motor cortex excitability and levodopa-induced dyskinesis were reduced by DM at a dose of 100 mg in a double-blind placebo-control study in patients with Parkinson's disease, (Verhagen et al, 1998) with only negligible side effects.

Dextromethorphan is rapidly metabolized in the liver (Woodworth et al, 1987) where it is transformed to dextrorphan, its active and more potent derivative as a NMDA antagonist. It was suggested that the side effects documented in clinical studies and attributed to the oral administration of DM might be mediated by this metabolite acting at the phencyclidine receptorial site rather than DM itself (Musacchio et al, 1989).

Satisfactory pain control achieved with the least amount of opiates has always been an important goal in view of both the psychological and somatic dependence these drugs may induce and the often intolerable side effects that may follow their extensive use. The searchers for techniques of pain control that will afford full orientation, coordination and collaboration, and normal respiration as well as stable hemodynamics view these factors as important cornerstones in postoperative planning of pain control. This applies equally to patients who had undergone either general or regional anesthesia and to inpatients as well as outpatients. Moreover, in view of the contention that persistent NMDA receptor activation can evoke central hyperexcitability that can lead to secondary pain, proper pain control should both modulate primary pain sensation and preempt an analgesic state that would prevent acute pain from progressing into chronic pain. This concept of preemptive analgesia (i.e., reducing pain sensation in advance) is feasible via NMDA modulation, as had been demonstrated by the administration of opiates and ketamine to patients before surgery (Kiss et al, 1992, Tverskoy et al, 1994). Importantly, this neuropharmacological receptor conditioning is also beneficial for reducing the need for additional doses of opiates post-operatively. In addition, while the neurovegetative stimulation and adrenergic overproduction that accompany the continuous neurally transmitted acute and, to a greater extent, secondary pain are clearly detrimental to all patients, they may be particularly harmful for cardiac patients. In this regard, the preemptive approach is an especially promising and beneficial one. The use of DM may, therefore, become an established component in protocols of treating pain and of alleviating the accompanying neurovegetative phenomena. Finally, the bioavailability of DM administered orally makes it much more convenient than the other anti-NMDA drugs, all of which are administered by injection, such as ketamine. As a potential morphine sparing agent for pain, the use of DM was shown to be efficient and well tolerated (Henderson et al, 1999).

It is noteworthy that NMDA receptor antagonists, including DM, are not in themselves anti-nociceptive (Ilkjaer 1997) but rather they inhibit central sensitization and, thus, the perception of primary and secondary pain (Price et al, 1994; Chia et al, 1999). The preemptive use of these antagonists, while blunting the development of a central sensitization of a nociceptive stimulus (Yamamoto et al, 1992), still requires the use of an analgesic for complete abolition of pain perception.

2. Other NMDA Antagonists

A non-limiting list of NMDA antagonist drugs which may be utilized in the present invention include dextromethorphan, dextrorphan, ketamine, amantadine, memantine, eliprodil, ifenprodil, phencyclidine, MK-801, dizocilpine, CCPene, flupirtine, or derivatives, salts, metabolites or complexes thereof.

Additional substances that block a major intracellular consequence of NMDA receptor activation and as such are useful in the practice of the invention include inhibitors of calmodulin such as the phenothiazines, in particular, chlorpromazine, chlorpromazine sulfoxide, prochlorperazine dimaleate, perphenazine, trifluoperazine, fluphenazine, fluphenazine enanthate, fluphenazine decanoate, thioridazine, mesoridazine besylate, piperacetazine, acetophenazine dimaleate, carphenazine dimaleate, butaperazine dimaleate and phenothiazine sulfoxide; naphthalenesulfonamides such as N-(6-aminohexyl)-5-chloro-1-naphthalenesulfonamide, N-(6-aminohexyl)-5-chloro-2-naphthalenesulfonamide and N-(6-aminohexyl)-5-bromo-2-naphthalenesulfonamide; 4-substituted-4H,6H-pyrrolo[1,2-a][4,1]benzoxazepines such as 1,3-dihydro-1-{1-[(4-methyl-4H,6H-pyrrolo[1,2-a][4,1]benzoxazepin-4-yl)methyl]-4-piperidinyl}-2H-benzimidazol-2-one; benzhydryls such as N-[2](diphenylmethylthioethyl]-2-(trifluoromethyl)-benzeneethanamine, N-[2-(bis(4-fluorophenyl)methylthio)-)ethyl]-2-(trifluoromethyl) benzene ethanamine and N-(bis(4-fluorophenyl)methylthio) ethyl]-3-(trifluoromethyebenzene ethanamine; tricyclic antidepressant drugs such as imipramine, 2-chloroimipramine and amitriptyline; penfluridol; haloperidol; pimoz-

C. Tramadol (+/−)-Tramadol is a synthetic 4-phenyl-piperidine analogue of codeine. It is a central analgesic with a low affinity for opiate receptors. Its selectivity for μ receptors has recently been demonstrated, and the M1 metabolite of tramadol, produced by liver O-demethylation, shows a higher affinity for opiate receptors than the parent drug. The rate of production of this M1 derivative (O-demethyl tramadol), is influenced by a polymorphic isoenzyme of the debrisoquine-type, cytochrome P450 2D6 (CYP2D6). One mechanism relates to its weak affinity for μ-opiate receptors (6,000-fold less than morphine, 100-fold less than d-propoxyphene, 10-fold less than codeine, and equivalent to dextromethorphan). Moreover, and in contrast to other opiates, the analgesic action of tramadol is only partially inhibited by the opiate antagonist naloxone, which suggests the existence of another mechanism of action. This was demonstrated by the discovery of a monoaminergic activity that inhibits noradrenaline (norepinephrine) and serotonin (5-hydroxytryptamine; 5-HT) reuptake, making a significant contribution to the analgesic action by blocking nociceptive impulses at the spinal level (Dayer et al, 1994 & 1997).

(+/−)-Tramadol is a racemic mixture of 2 enantiomers, each one displaying differing affinities for various receptors, i.e., (1R,2R or 1S,2S)-(dimethylaminomethyl)-1-(3-methoxyphenyl)-cyclohexanol (tramadol). (+/−)-tramadol is a selective agonist of μ receptors and preferentially inhibits serotonin reuptake, whereas (−)-tramadol mainly inhibits noradrenaline reuptake. The action of these 2 enantiomers is both complementary and synergistic and results in the analgesic effect of (+/−)-tramadol. After oral administration, tramadol demonstrates 68% bioavailability, with peak serum concentrations reached within 2 hours. The elimination kinetics can be described as 2-compartmental, with a half-life of 5.1 hours for tramadol and 9 hours for the M1 derivative after a single oral dose of 100 mg. This explains the approximately 2-fold accumulation of the parent drug and its M1 derivative that is observed during multiple dose treatment with tramadol. The recommended daily dose of tramadol is between 50 and 100 mg every 4 to 6 hours, with a maximum dose of 400 mg/day. The duration of the analgesic effect after a single oral dose of tramadol 100 mg is about 6 hours. Adverse effects, and nausea in particular, are dose dependent and therefore considerably more likely to appear if the loading dose is high. The reduction of this dose during the first days of treatment is an important factor in improving tolerability. Other adverse effects are generally similar to those of opiates, although they are usually less severe, and can include respiratory depression, dysphoria and constipation. Tramadol can be administered concomitantly with other analgesics, particularly those with peripheral action, while drugs that depress CNS function may enhance the sedative effect of tramadol. Tramadol has pharmacodynamic and pharmacokinetic properties that are highly unlikely to lead to dependence. This was confirmed by various controlled studies and post-marketing surveillance studies, which reported an extremely small number of patients developing tolerance or instances of tramadol abuse (Raffa et al, 1993; Lee et al, 1993). Although it has proven to be a safe and effective agent for the control of pain, adverse effects can occur with its use. It has been reported the occurrence of seizure activity after the inadvertent administration of 4 mg/kg of tramadol to a child (Tobias 1997).

1. Tramadol Analogs

A tramadol may be substituted for or used in combination with tramadol according to the present invention. A non-limiting list of tramadol analogs which may be utilized in the present invention include the tramadol N-oxide derivative ("tramadol N-oxide"), the tramadol O-desmethyl derivative ("O-desmethyl tramadol"), venlafaxine, (R/S)-1-[2-(dimethylamino)-1-(4-methoxyphenyl)ethyl]cyclohexanol and O-desmethylvenlafaxine or mixtures, stereoisomers, recemates, metabolites, salts or complexes thereof.

Venlafaxine is a novel SSRI chemically unrelated to other SSRIs but chemically similar to the tramadol (FIG. 1; Markowitz 1998). The chemical structures of venlafaxine and tramadol are similar, demonstrating the similarity between these two antidepressant and analgesic substances, respectively. It is designated (R/S)-1-[2-(dimethylamino)-1-(4-methoxyphenyl)ethyl]cyclohexanol or (±)-1-[a-[(dimethylamino)methyl]-p-methoxybenzyl]cyclohexanol and has the empirical formula of $C_{17}H_{27}NO_2$. Venlafaxine hydrochloride is a white to off-white crystalline solid with a solubility of 572 mg/mL in water (adjusted to ionic strength of 0.2 M with sodium chloride. Its octanol:water (0.2M sodium chloride) partition coefficient is 0.43. Venlafaxine hydrochloride (Effexor) is formulated as capsule for oral administration. Capsules contain venlafaxine hydrochloride equivalent to 37.5 mg, 75 mg, or 150 mg venlafaxine. In certain embodiments, it is anticipated that venlafaxine may be included in a pharmaceutical composition or the present invention in combination with or to substitute for tramadol.

The mechanism of the antidepressant action of venlafaxine in humans is believed to be the same as with other SSRIs, associated with its potentiation of neurotransmitter activity in the CNS as with other SSRIs: preclinical studies have shown that venlafaxine and its active metabolite, O-desmethylvenlafaxine (ODV), are potent inhibitors of neuronal serotonin and norepinephrine reuptake and weak inhibitors of dopamine reuptake. That venlafaxine is analgesia is seen in studies in animals that show that venlafaxine is effective in reversing chronic neuropathic pain secondary to thermal hyperalgesia, and additionally is effective in treating the hyperalgesia of neuropathic pain due to chronic sciatic nerve constriction injury in rats (Lang 1998). Venlafaxine-induced antinociception is significantly inhibited by naloxone, nor-BNI and naltrindole but not by β-FNA or naloxonazine, implying involvement of κ1- and δ-opioid mechanisms. When adrenergic and serotoninergic antagonists are used, yohimbine but not phentolamine or metergoline, decreased antinociception elicited by venlafaxine, implying a clear α2- and a minor α1-adrenergic mechanism of antinociception. Therefore, the antinociceptive effect of venlafaxine is mainly influenced by the κ- and δ-opioid receptor subtypes combined with the α2-adrenergic receptor. These results suggest a potential use of venlafaxine in the management of some pain syndromes. However, further research is needed in order to establish both the exact clinical indications and the effective doses of venlafaxine when prescribed for neuropathic pain (Schreiber 1999).

D. Gabapentin

Gabapentin (GBP; Neurontin®) is an anticonvulsant that has found increased utility for the treatment of clinical neuropathic pain. Although originally developed for the treatment of spasticity and epilepsy, recent attention has focused on the utility of GBP for the treatment of neuropathic pain based on its efficacy and minimal side-effect profile in clinical trials (Rice and Maton, 2001). In rodent neuropathic pain models, GBP effectively attenuates thermal and mechanical hypersensitivity following peripheral nerve ligation (Xiao and Bennett, 1996; Hunter et al., 1997; Hwang and Yaksh, 1997). GBP has also been shown to inhibit thermal and mechanical hyperalgesia following carrageenan-induced inflammation (Field et al., 1997b; Lu and Westlund, 1999); however, other studies have reported limited effectiveness of GBP for inflammatory pain (Gould et al., 1997; Patel et al., 2001). Additionally, GBP inhibits spontaneous nociceptive behaviors and mechanical hyperalgesia produced by intraplantar formalin or surgical incision, respectively (Field et al., 1997a, b). The antinociceptive effects of GBP in models of neuropathic, inflammatory, and surgical pain appear to be selective for injury-induced hypersensitivity, since responses to acute noxious stimuli are unaffected (Field et al., 1997b; Hunter et al., 1997).

Despite growing interest in the analgesic properties of GBP, its mechanism of action remains unclear. Although it is a GABA analog, GBP does not bind $GABA_A$ or $GABA_B$ receptors or interact with GABA transporters (for review, see Taylor et al., 1998). GBP has been shown, however, to increase brain extracellular GABA levels in both rat and human studies (Loscher et al., 1991; Petroff et al., 1996). This increased extracellular GABA is likely due to either directly stimulated GABA release (Gotz et al., 1993; Gu and Huang, 2002) or changes in GABA metabolism via effects on glutamic acid decarboxylase and/or GABA-transaminase (Goldlust et al., 1995). The notion that GBP increases extracellular GABA is consistent with its effectiveness for neuropathic pain, since the pathology associated with this condition includes disruption of tonic inhibitory GABAergic transmission (Wiesenfeld-Hallin et al., 1997).

Gabapentin is commercially supplied as Neurontin® Capsules, Neurontin® Tablets, and Neurontin® Oral Solution, as imprinted hard shell capsules containing 100 mg, 300 mg, and 400 mg of gabapentin, elliptical film-coated tablets containing 600 mg and 800 mg of gabapentin or an oral solution containing 250 mg/5 mL of gabapentin. Gabapentin bioavailability is not dose proportional; i.e., as dose is increased, bioavailability decreases. Bioavailability of gabapentin is approximately 60%, 47%, 34%, 33%, and 27% following 900, 1200, 2400, 3600, and 4800 mg/day given in 3 divided doses, respectively. Food has only a slight effect on the rate and extent of absorption of gabapentin (14% increase in AUC and Cmax). Less than 3% of gabapentin circulates bound to plasma protein. The apparent volume of distribution of gabapentin after 150 mg intravenous administration is 58±6 L (Mean±SD). In patients with epilepsy, steady-state predose (Cmin) concentrations of gabapentin in cerebrospinal fluid were approximately 20% of the corresponding plasma concentrations. Gabapentin is eliminated from the systemic circulation by renal excretion as unchanged drug. Gabapentin is not appreciably metabolized in humans. Gabapentin elimination half-life is 5 to 7 hours and is unaltered by dose or following multiple dosing. Gabapentin elimination rate constant, plasma clearance, and renal clearance are directly proportional to creatinine clearance. In elderly patients, and in patients with impaired renal function, gabapentin plasma clearance is reduced. Gabapentin can be removed from plasma by hemodialysis.

Currently gabapentin is indicated as adjunctive therapy in the treatment of partial seizures with and without secondary generalization in patients over 12 years of age with epilepsy. Gabapentin is also indicated as adjunctive therapy in the treatment of partial seizures in pediatric patients age 3% 12 years.

In vitro studies were conducted to investigate the potential of gabapentin to inhibit the major cytochrome P450 enzymes (CYP1A2, CYP2A6, CYP2C9, CYP2C19, CYP2D6, CYP2E1, and CYP3A4) that mediate drug and xenobiotic metabolism using isoform selective marker substrates and human liver microsomal preparations. Only at the highest concentration tested (171 µg/mL; 1 mM) was a slight degree of inhibition (14%-30%) of isoform CYP2A6 observed. No inhibition of any of the other isoforms tested was observed at gabapentin concentrations up to 171 µg/mL (approximately 15 times the Cmaxat 3600 mg/day).

Gabapentin is not appreciably metabolized nor does it interfere with the metabolism of commonly coadministered antiepileptic drugs. Gabapentin is given orally with or without food. In adults with postherpetic neuralgia, gabapentin therapy may be initiated as a single 300-mg dose on Day 1, 600 mg/day on Day 2 (divided BID), and 900 mg/day on Day 3 (divided TID). The dose can subsequently be titrated up as needed for pain relief to a daily dose of 1800 mg (divided TID). In clinical studies, efficacy was demonstrated over a range of doses from 1800 mg/day to 3600 mg/day with comparable effects across the dose range. Additional benefit of using doses greater than 1800 mg/day was not demonstrated. For patients >12 years of age: The effective dose of Neurontin is 900 to 1800 mg/day and given in divided doses (three times a day) using 300 or 400 mg capsules, or 600 or 800 mg tablets. The starting dose is 300 mg three times a day. If necessary, the dose may be increased using 300 or 400 mg capsules, or 600 or 800 mg tablets three times a day up to 1800 mg/day. Dosages up to 2400 mg/day have been well tolerated in long-term clinical studies. Doses of 3600 mg/day have also been administered to a small number of patients for a relatively short duration, and have been well tolerated. The maximum time between doses in the TID schedule should not exceed 12 hours.

The most commonly observed adverse events associated with the use of gabapentin in adults, not seen at an equivalent frequency among placebo-treated patients, were dizziness, somnolence, and peripheral edema. The most commonly observed adverse events associated with the use of gabapentin in combination with other antiepileptic drugs in patients >12 years of age, not seen at an equivalent frequency among placebo-treated patients, were somnolence, dizziness, ataxia, fatigue, and nystagmus. The most commonly observed adverse events reported with the use of gabapentin in combination with other antiepileptic drugs in pediatric patients 3 to 12 years of age, not seen at an equal frequency among placebo-treated patients, were viral infection, fever, nausea and/or vomiting, somnolence, and hostility.

Pregabalin, an analog of gabapentin, is sold commercially as pregabalin capsules and is administered orally and are supplied as imprinted hard-shell capsules containing 25, 50, 75, 100, 150, 200, 225, and 300 mg of pregabalin, along with lactose monohydrate, cornstarch, and talc as inactive ingredients. The capsule shells contain gelatin and titanium dioxide. In addition, the orange capsule shells contain red iron oxide and the white capsule shells contain sodium lauryl sulfate and colloidal silicon dioxide. Colloidal silicon dioxide is a manufacturing aid that may or may not be present in the capsule shells. The imprinting ink contains shellac, black iron oxide, propylene glycol, and potassium hydroxide.

Treatment with pregabalin 100 and 200 mg three times a day statistically significantly improved the endpoint mean pain score and increased the proportion of patients with at least a 50% reduction in pain score from baseline. There was no evidence of a greater effect on pain scores of the 200 mg three times a day dose than the 100 mg three times a day dose, but there was evidence of dose dependent adverse reactions. A 13-week study compared pregabalin 75, 150, and 300 mg twice daily with placebo. Patients with creatinine clearance (CLcr) between 30 to 60 mL/min were randomized to 75 mg, 150 mg, or placebo twice daily. Patients with creatinine clearance greater than 60 mL/min were randomized to 75 mg, 150 mg, 300 mg or placebo twice daily. In patients with creatinine clearance greater than 60 mL/min treatment with all doses of pregabalin statistically significantly improved the endpoint mean pain score and increased the proportion of patients with at least a 50% reduction in pain score from baseline. Despite differences in dosing based on renal function, patients with creatinine clearance between 30 to 60 mL/min tolerated pregabalin less well than patients with creatinine clearance greater than 60 mL/min as evidenced by higher rates of discontinuation due to adverse reactions. Some patients experienced a decrease in pain as early as Week 1, which persisted throughout the study.

A 8-week study compared pregabalin 100 or 200 mg three times a day with placebo, with doses assigned based on creatinine clearance. Patients with creatinine clearance between 30 to 60 mL/min were treated with 100 mg three times a day, and patients with creatinine clearance greater than 60 mL/min were treated with 200 mg three times daily. Treatment with pregabalin statistically significantly improved the endpoint mean pain score and increased the proportion of patients with at least a 50% reduction in pain score from baseline. Some patients experienced a decrease in pain as early as Week 1, which persisted throughout the study.

A 8-week study compared pregabalin 50 or 100 mg three times a day with placebo with doses assigned regardless of creatinine clearance. Treatment with pregabalin 50 and 100 mg three times a day statistically significantly improved the endpoint mean pain score and increased the proportion of patients with at least a 50% reduction in pain score from baseline. Patients with creatinine clearance between 30 to 60 mL/min tolerated pregabalin less well than patients with creatinine clearance greater than 60 mL/min as evidenced by markedly higher rates of discontinuation due to adverse reactions. Some patients experienced a decrease in pain as early as Week 1, which persisted throughout the study.

A 14-week study compared pregabalin total daily doses of 300 mg, 450 mg and 600 mg with placebo. Patients were enrolled with a minimum mean baseline pain score of greater than or equal to 4 on an 11-point numeric pain rating scale and a score of greater than or equal to 40 mm on the 100 mm pain visual analog scale (VAS). The baseline mean pain score in this trial was 6.7. Responders to placebo in an initial one-week run-in phase were not randomized into subsequent phases of the study. A total of 64% of patients randomized to pregabalin completed the study. There was no evidence of a greater effect on pain scores of the 600 mg daily dose than the 450 mg daily dose, but there was evidence of dose-dependent adverse reactions.

The maximum recommended dose of pregabalin for neuropathic pain associated with diabetic peripheral neuropathy is 100 mg three times a day (300 mg/day) in patients with creatinine clearance of at least 60 mL/min. Dosing should begin at 50 mg three times a day (150 mg/day) and may be increased to 300 mg/day within 1 week based on efficacy and tolerability. Because pregabalin is eliminated primarily by renal excretion, the dose should be adjusted for patients with reduced renal function. Although pregabalin was also studied at 600 mg/day, there is no evidence that this dose confers additional significant benefit and this dose was less well tolerated. In view of the dose-dependent adverse reactions, treatment with doses above 300 mg/day is not recommended.

The recommended dose of pregabalin for fibromyalgia is 300 to 450 mg/day. Dosing should begin at 75 mg two times a day (150 mg/day) and may be increased to 150 mg two times a day (300 mg/day) within 1 week based on efficacy and tolerability. Patients who do not experience sufficient benefit with 300 mg/day may be further increased to 225 mg two times a day (450 mg/day). Although pregabalin was also studied at 600 mg/day, there is no evidence that this dose confers additional benefit and this dose was less well tolerated. In view of the dose-dependent adverse reactions, treatment with doses above 450 mg/day is not recommended. Because pregabalin is eliminated primarily by renal excretion, the dose should be adjusted for patients with reduced renal function (creatinine clearance less than 60 mL/min).

In clinical trials in patients with neuropathic pain associated with diabetic peripheral neuropathy, 9% of patients treated with pregabalin and 4% of patients treated with placebo discontinued prematurely due to adverse reactions. In the pregabalin treatment group, the most common reasons for discontinuation due to adverse reactions were dizziness (3%) and somnolence (2%). In comparison, <1% of placebo patients withdrew due to dizziness and somnolence. Other reasons for discontinuation from the trials, occurring with greater frequency in the pregabalin group than in the placebo group, were asthenia, confusion, and peripheral edema. Each of these events led to withdrawal in approximately 1% of patients.

In clinical trials of patients with fibromyalgia, 19% of patients treated with pregabalin (150-600 mg/day) and 10% of patients treated with placebo discontinued prematurely due to adverse reactions. In the pregabalin treatment group, the most common reasons for discontinuation due to adverse reactions were dizziness (6%) and somnolence (3%). In comparison, <1% of placebo-treated patients withdrew due to dizziness and somnolence. Other reasons for discontinuation from the trials, occurring with greater frequency in the pregabalin treatment group than in the placebo treatment group, were fatigue, headache, balance disorder, and weight increased. Each of these adverse reactions led to withdrawal in approximately 1% of patients.

Amitriptyline is a tricyclic agent used for the treatment of major depression (Baldessarini, 1995). Amitriptyline, nortriptyline, and desipramine have been established as analgesics independent of their antidepressant effects (Galer 1995). Although their mechanism of analgesic action has not been clearly defined, tricyclic antidepressants are thought to have an inhibitory effect on nociceptive pathways by blocking the reuptake of serotonin and norepinephrine (Calissi 1995). Originally, the major mechanism of the analgesic effect of tricyclic antidepressants was believed to be related to serotonin reuptake inhibition. However, the selective serotonin reuptake inhibitor antidepressants have not demonstrated substantial effectiveness in neuropathic pain (Galer 1995; Sindrup 1999; Lipman 1996). Animal models of peripheral neuropathic pain have shown that tricyclic antidepressants act as sodium channel blockers, similar to local anesthetic and antiarrhythmic agents (Jacobson 1995).

Amitriptyline drug is effective in the treatment of postherpetic neuralgia, diabetic neuropathy, and other neuropathic pain syndromes (Monks and Merskey, 1984). Oral amitriptyline achieves a good or moderate response in about two-thirds of patients with postherpetic neuralgia and three-quarters of patients with painful diabetic neuropathy; such neurogenic pain syndromes are often unresponsive to narcotic analgesics (Bryson and Wilde, 1996). Whether analgesic effects of amitriptyline are linked to its mood-altering activity and/or are attributable to a discrete pharmacological action is unknown. Above the therapeutic plasma concentration of 0.3 to 0.8 µM, the tricyclic antidepressants have significant effects on the cardiovascular system, including direct depression of the myocardium and evidence of prolonged conduction times (Nattel et al., 1984; Nattel, 1985); with an overdose of >3 µM, these effects may be life-threatening (Amsterdam et al., 1980). The known physiological targets of tricyclic antidepressants in the central nervous system are the 5-HT2 serotonin receptors and the α1-adrenergic receptors (Baldessarini, 1995).

In addition to these primary targets, tricyclic antidepressants are also effective K+ and Na+ channel blockers. For example, tricyclic imipramine inhibits transient K+ channels in hippocampal neurons with an IC50 of ~6 µM (Kuo, 1998). In adrenal chromaffin cells, amitriptyline blocks peak Na+ currents with an IC50 value of 20.2 µM (Pancrazio et al., 1998). In cardiac myocytes, 0.4 µM amitriptyline elicits a profound use-dependent block of Na+ current during repetitive pulses at a frequency of 5 Hz (Barber et al., 1991). Such a use-dependent phenomenon is qualitatively similar to that found when Na+ channels are exposed to local anesthetics (LAs) (Hille, 1992). Because recovery from the use-dependent block of amitriptyline is slow in cardiac Na+ channels, with a time constant of 13.6 s, Barber et al. (1991) suggested that the block of cardiac Na+ channels by amitriptyline is the probable cause of cardiac toxicity.

The location of the amitriptyline binding site in Na+ channels has not been delimited. Although the blocking effects of amitriptyline are similar to those of LAs, no direct evidence demonstrates that amitriptyline and LAs share a common binding site. Mammalian Na+-channel isoforms consist of a large α-subunit and one or two smaller β-subunits (Catterall, 1995; Fozzard and Hanck, 1996). The α-subunit alone can form functional channels when transiently expressed in human embryonic kidney (HEK) cells. The proposed organization of the α-subunit Na+ channel consists of four homologous domains with six transmembrane segments each. The LA receptor has been mapped within the segment D4-S6 of the rat brain type IIA isoform (Ragsdale et al., 1994). The homologous residues of human heart Na+ channels (Gellens et al., 1992) involved in LA binding are hH1-F1760 and hH1-Y1767. It has been shown that, near the therapeutic plasma concentration of 1 µM, amitriptyline is an effective use-dependent blocker of hH1 Na+ channels during repetitive pulses (~55% block at 5 Hz). The tonic block for resting and for inactivated hH1 channels by amitriptyline (0.1-100 µM) yielded $IC_{50}$ values (50% inhibitory concentration) of 24.8±2.0 (n=9) and 0.58±0.03 µM (n=7), respectively (Nau 2000).

1. Gabapentin Analogs

A non-limiting list of analogs of gabapentin which may be used in the present invention include pregabalin, 3-methyl gabapentin, [(1R,5R,6S)-6-(Aminomethyl)bicyclo[-3.2.0] hept-6-yl]acetic acid, 3-(1-Aminomethyl-cyclohexylmethyl)-4H-[1,2,4]-oxadiazol-5-one, C-[1-(1H-Tetrazol-5-yl-methyl)-cycloheptyl]-methylamine, (3S,4S)-(1-Aminomethyl-3,4-dimethyl-cyclopentyl)-acetic acid, (1α, 3α,5α)(3-amino-methyl-bicyclo[3.2.0]hept-3-yl)-acetic acid, (3S,5R)-3-Aminomethyl-5-methyl-octanoic acid, (3S,5R)-3-amino-5-methyl-heptanoic acid, (3S,5R)-3-amino-5-methyl-nonanoic acid and (3S,5R)-3-Amino-5-methyl-octanoic acid, (1-aminomethyl-3-methylcyclohexyl)acetic acid, (1-aminomethyl-3-methylcyclopentyl)acetic acid, (S)-3-(aminomethyl)-5-methylhexanoic acid, 3-aminomethyl-5-methyl-hexanoic acid, (1-aminomethyl-3,4-dimethylcyclopentyl)acetic acid or a pharmaceutically acceptable salt thereof, or an ester or amide derivative thereof.

E. Capsaicinoids

Capsaicin is a natural constituent in pungent red chili peppers. Depending on the concentration used and the mode of application, capsaicin can selectively activate, desensitize, or exert a neurotoxic effect on small diameter sensory afferent nerves while leaving larger diameter afferents unaffected (Holzer, 1991; Winter et al, 1995). Sensory neuron activation occurs due to interaction with a ligand-gated nonselective cation channel termed the vanilloid receptor (VR-1) (Caterina et al, 1997), and receptor occupancy triggers $Na^+$ and $Ca^{2+}$ ion influx, action potential firing, and the consequent burning sensation associated with spicy food or capsaicin-induced pain. VR1 receptors are present on both C and M fibers, and can be activated by capsaicin and its analogs, heat, acidification, and lipid metabolites (Tominaga et al, 1998; Caterina and Julius, 2001). Desensitization occurs with repeated administration of capsaicin, is a receptor-mediated process, and involves $Ca^{2+}$- and calmodulin-dependent processes and phosphorylation of the cation channel (Winter et al, 1995; Wood and Docherty, 1997).

Capsaicin induces release of substance P and calcitonin gene-related peptide from both peripheral and central terminals of sensory neurons, and desensitization inhibits such release (Holzer, 1991); such inhibition may result from inhibition of voltage-gated $Ca^{2+}$-currents (Docherty et al, 1991; Winter et al, 1995). Desensitization leads to analgesia in rodent paradigms, with specific characteristics of analgesia depending on the dose of capsaicin, route of administration, treatment paradigm (i.e., acute or repeated administration), and age of the animal (Holzer, 1991; Winter et al, 1995). The topical skin application of capsaicin to rodents produces analgesia (Kenins, 1982; Lynn et al, 1992), but variability in outcome can occur due to the concentration, the number of applications, and the different vehicles used that can affect the rate and extent of skin penetration (Carter and Francis, 1991; McMahon et al, 1991).

Viral replication, immune regulation, and induction of various inflammatory and growth-regulatory genes require activation of a nuclear transcription factor (NF)-κ-B. Agents that can block NF-κ-B activation have potential to block downstream responses mediated through this transcription factor. Capsaicin (8-methyl-N-vanillyl-6-nonenamide) has been shown to regulate a wide variety of activities that require NF-κ-B activation (Singh 1996). The pretreatment of human myeloid ML-1a cells with capsaicin blocked TNF-mediated activation of NF-κ-B in a dose- and time-dependent manner. Capsaicin treatment of cells also blocked the degradation of 1-κ-B alpha, and thus the nuclear translocation of the p65 subunit of NF-κ-B, which is essential for NF-κ-B activation. TNF-dependent promoter activity of I-κ-B alpha, which contains NF-κ-B binding sites, was also inhibited by capsaicin.

Acute intradermal injection of capsaicin to the skin in humans produces a burning sensation and flare response; the area of application becomes insensitive to mechanical and thermal stimulation, the area of flare exhibits a primary hyperalgesia to mechanical and thermal stimuli, and an area beyond the flare exhibits secondary allodynia (Simone et al, 1989; LaMotte et al, 1991). Repeated application to normal skin produces desensitization to this response and thus forms the basis of the therapeutic use of topical capsaicin in humans. Desensitization involves both physiological changes in the terminals of the sensory neuron noted above, as well as a degree of loss of sensory fiber terminals within the epidermis (Nolano et al, 1999).

Topical capsaicin preparations of 0.025 and 0.075% are available for human use, and these produce analgesia in randomized double-blind placebo-controlled studies, open label trials, and clinical reports (Watson, 1994; Rains and Bryson, 1995). Topical capsaicin produces benefit in postherpetic neuralgia (Bernstein et al, 1989; Watson et al, 1993), diabetic neuropathy (Capsaicin Study Group, 1992), postmastectomy pain syndrome (Watson and Evans, 1992; Dini et al, 1993), oral neuropathic pain, trigeminal neuralgia, and temperomandibular joint disorders (Epstein and Marcoe, 1994; Hersh et al, 1994), cluster headache (following intranasal application) (Marks et al, 1993), osteoarthritis (McCarthy and McCarthy, 1992), and dermatological and cutaneous conditions (Hautkappe et al, 1998). Whereas pain relief is widely observed in these studies, the degree of relief is usually modest, although some patients have a very good result. Topical capsaicin is generally not considered a satisfactory sole therapy for chronic pain conditions and is often considered an adjuvant to other approaches (Watson, 1994). No significant benefit was reported in chronic distal painful neuropathy (Low et al, 1995) or with human immunodeficiency virus-neuropathy (Paice et al, 2000).

The distribution and metabolism of capsaicin and/or dihydrocapsaicin has been studied in rats. Capsaicin is distributed to the brain, spinal cord, liver and blood within 20 mins. of i.v. administration. Oral doses of dihydrocapsaicin in the rat showed metabolic activity associated with its absorption into the portal vein. Capsaicin and dihydrocapsaicin are metabolized in the liver by the mixed-function oxidation system (cytochrome P-450-dependent system). It is assumed that capsaicin is excreted in urine. In rats, most of dihydrocapsaicin is known to be rapidly metabolized and excreted in the urine (Rumsfield and West, 1991).

Oral dosing of rats with capsaicin and dihydrocapsaicin results in an 85% absorption in the jejunum after 3 hours (Rumsfield and West, 1991). With respect to topical applications of capsaicin, it has been estimated that assuming 100% of a topically-applied dose is absorbed into the body, an application of 90 g capsaicin (2 tubes of cream, 0.025% capsaicin) per week would result in a daily exposure of 0.064 mg/kg capsaicin for a 50 kg person. This represents less than 10% of the dietary intake of a typical Indian or That diet (Rumsfield and West, 1991).

The most frequently encountered adverse effect with capsaicin is burning pain at the site of application, particularly in the first week of application. This can make it impossible to blind trials and can lead to dropout rates ranging from 33 to 67% (Watson et al, 1993; Paice et al, 2000). Another factor in compliance is the time delay before therapeutic effect is observed (at least a week, but sometimes several weeks). One approach toward minimizing adverse effects and accelerating the rate of analgesia has been to deliver a higher capsaicin concentration (5-10%) under regional anesthesia, and this produced sustained analgesia lasting 1 to 8 weeks in cases of complex regional pain syndrome and neuropathic pain (Robbins et al, 1998). When topical local anesthetics were applied with 1% topical capsaicin, no alteration in pain produced by the capsaicin was observed in healthy subjects (Fuchs et al, 1999) indicating that this cotreatment was not sufficient to block the pain induced by capsaicin.

Capsaicin is believed to cause depolarization of C-fiber polymodal nociceptors (Lynn 1990; Marsh 1987) and release of substance P, which is a neurotransmitter that relays pain signals to the brain. This action may actually increase pain sensation after initial use. However, repeat applications deplete the reserves of substance P at the afferent neurons leading to pain relief (Nolano 1999). Depletion of substance P does not occur immediately. Effective use of the cream (0.075% capsaicin) requires topical application 4 or 5 times daily for a period of at least 4 weeks.

A non-limiting list of capsaiciniods which may be used in the present invention include capsaicin, homocapsaicin, nordihydrocapsaicin, dihydrocapsaicin, homodihydrocapsaicin or any compounded mixture thereof.

1. Capsaicinoid Esters

In order to make the capsaicin to have less irritation to the skin and significantly less burning sensation to the stomach, the capsaicin has been esterified at the phenolic position. These esters have the general formula I:

$$R\text{—}CO\text{—}O_1CAP \qquad (I)$$

wherein CAP refers to a capsaicinoid and $O_1CAP$ refers to an oxygen present in an alcohol group of a corresponding non-esterified capsaicinoid. FIG. 3 shows examples of non-esterified and esterified capsaicinoids. Various esterified capsaicinoids are described in US 2008/0020996 and U.S. Pat. No. 4,493,848 and U.S. Pat. No. 4,564,633, which are incorporated by reference in its entirety, and may be used with the present invention. Once administered to a subject, the esterified capsaicinoid may be enzymatically converted to the corresponding capsaicinoid once administered to a subject.

In formula I, R is selected from $C_{1-22}$ alkyl, $C_{6-22}$ aryl, $C_{1-22}$ alkylene, $C_{1-22}$ alkenyl, $C_{1-22}$ alkynyl and/or $C_{1-22}$ arylene. In various embodiments, the alkyl, alkylene, alkenyl, alkynyl and/or arylene may be $C_{1-18}$, $C_{1-12}$, or $C_{1-6}$. The aryl may be $C \leq 22$, $C \leq 18$, $C \leq 12$, or $C=6$. The alkyl, aryl and/or alkylene groups may be substituted or unsubstituted, branched or straight chains. In addition, R may contain heteroatoms and may be straight chained or branched.

Examples of suitable straight-chain alkyl groups in formula I include methyl, ethyl, propyl, butyl, hexyl, heptyl, octyl, dodecyl, 1-pentadecyl, 1-heptadecyl and the like groups.

Examples of suitable branched chain alkyl groups in formula I include isopropyl, sec-butyl, t-butyl, 2-methylbutyl, 2-pentyl, 3-pentyl and the like groups. Examples of suitable cyclic alkyl groups in formula I include cyclopropyl, cyclobutyl, cyclopentyl and cyclohexyl groups.

Examples of suitable "alkenyl" groups in formula I include vinyl (ethenyl), 1-propenyl, i-butenyl, pentenyl, hexenyl, n-decenyl and c-pentenyl and the like.

The groups may be substituted, generally with 1 or 2 substituents, wherein the substituents are independently selected from halo, hydroxy, alkoxy, amino, mono- and dialkylamino, nitro, carboxyl, alkoxycarbonyl, and cyano groups.

By the expression "phenalkyl groups wherein the alkyl moiety contains 1 to 3 or more carbon atoms" is meant benzyl, phenethyl and phenylpropyl groups wherein the phenyl moiety may be substituted. When substituted, the phenyl moiety of the phenalkyl group may contain independently from 1 to 3 or more alkyl, hydroxy, alkoxy, halo, amino, mono- and dialkylamino, nitro, carboxyl, alkoxycarbonyl and cyano groups.

Examples of suitable "heteroaryl" in formula I are pyridinyl, thienyl or imidazolyl.

As noted herein, the expression "halo" is meant in the conventional sense to include F, Cl, Br, and I.

Among the compounds represented by the general Formula I, preferred compounds are such in which R is one of the following groups: methyl, ethyl, propyl, butyl, pentyl, hexyl, 1-pentadecyl, 1-heptadecyl, isobutyl, methoxyethyl, ethoxyethyl, benzyl and nicotinyl.

A non-limiting list of capsaicin which may be used in the present invention include capsaicin, homocapsaicin, nordihydrocapsaicin, dihydrocapsaicin, homodihydrocapsaicin or any compounded mixture thereof. Capsaicin palmitate is an ester of capsaicin which may be used with the present invention.

For oral administration, the preferred ester is the palmitate esters of capsaicins. These esters result in less irritation and burning sensation to the stomach, as compared to capsaicin. Without wishing to be bound by any theory, pain relief is achieved via binding to the VR1 receptors and the depletion of substance P.

2. Chemical Definitions

For the groups below, the following parenthetical subscripts further define the groups as follows: "(Cn)" defines the exact number (n) of carbon atoms in the group; "(C≤n)" defines the maximum number (n) of carbon atoms that can be in the group; (Cn-n') defines both the minimum (n) and maximum number (n') of carbon atoms in the group. For example, "alkoxy$_{(C \le 10)}$" designates those alkoxy groups having from 1 to 10 carbon atoms (e.g., 1, 2, 3, 4, 5, 6, 7, 8, 9, or 10, or any range derivable therein (e.g., 3-10 carbon atoms)). Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3-10 carbon atoms)).

The term "alkyl" when used without the "substituted" modifier refers to a non-aromatic monovalent group, having a saturated carbon atom as the point of attachment, a linear or branched, cyclo, cyclic or acyclic structure, no carbon-carbon double or triple bonds, and no atoms other than carbon and hydrogen. The groups, —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neo-pentyl), cyclobutyl, cyclopentyl, cyclohexyl, and cyclohexylmethyl are non-limiting examples of alkyl groups. The term "substituted alkyl" refers to a non-aromatic monovalent group, having a saturated carbon atom as the point of attachment, a linear or branched, cyclo, cyclic or acyclic structure, no carbon-carbon double or triple bonds, and at least one atom independently selected from the group consisting of N, O, F, Cl, Br, I, Si, P, and S. The following groups are non-limiting examples of substituted alkyl groups: —CH$_2$OH, —CH$_2$Cl, —CH$_2$Br, —CH$_2$SH, —CF$_3$, —CH$_2$CN, —CH$_2$C(O)H, —CH$_2$C(O)OH, —CH$_2$C(O)OCH$_3$, —CH$_2$C(O)NH$_2$, —CH$_2$C(O)NHCH$_3$, —CH$_2$C(O)CH$_3$, —CH$_2$OCH$_3$, —CH$_2$OCH$_2$CF$_3$, —CH$_2$OC(O)CH$_3$, —CH$_2$NH$_2$, —CH$_2$NHCH$_3$, —CH$_2$N(CH$_3$)$_2$, —CH$_2$CH$_2$Cl, —CH$_2$CH$_2$OH, —CH$_2$CF$_3$, —CH$_2$CH$_2$OC(O)CH$_3$, —CH$_2$CH$_2$NHCO$_2$C(CH$_3$)$_3$, and —CH$_2$Si(CH$_3$)$_3$.

The term "alkenyl" when used without the "substituted" modifier refers to a monovalent group, having a nonaromatic carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CH—C$_6$H$_5$. The term "substituted alkenyl" refers to a monovalent group, having a nonaromatic carbon atom as the point of attachment, at least one nonaromatic carbon-carbon double bond, no carbon-carbon triple bonds, a linear or branched, cyclo, cyclic or acyclic structure, and at least one atom independently selected from the group consisting of N, O, F, Cl, Br, I, Si, P, and S. The groups, —CH=CHF, —CH=CHCl and —CH=CHBr, are non-limiting examples of substituted alkenyl groups.

The term "alkynyl" when used without the "substituted" modifier refers to a monovalent group, having a nonaromatic carbon atom as the point of attachment, a linear or branched, cyclo, cyclic or acyclic structure, at least one carbon-carbon triple bond, and no atoms other than carbon and hydrogen. The groups, —C≡CH, —C≡CCH$_3$, —C≡CC$_6$H$_5$ and —CH$_2$C≡CCH$_3$, are non-limiting examples of alkynyl groups. The term "substituted alkynyl" refers to a monovalent group, having a nonaromatic carbon atom as the point of attachment and at least one carbon-carbon triple bond, a linear or branched, cyclo, cyclic or acyclic structure, and at least one atom independently selected from the group consisting of N, O, F, Cl, Br, I, Si, P, and S. The group, —C≡CSi(CH$_3$)$_3$, is a non-limiting example of a substituted alkynyl group.

The term "aryl" when used without the "substituted" modifier refers to a monovalent group, having a aromatic carbon atom as the point of attachment, said carbon atom forming part of a six-membered aromatic ring structure wherein the ring atoms are all carbon, and wherein the monovalent group consists of no atoms other than carbon and hydrogen. Non-limiting examples of aryl groups include phenyl (Ph), methylphenyl, (dimethyl)phenyl, —C$_6$H$_4$CH$_2$CH$_3$ (ethylphenyl), —C$_6$H$_4$CH$_2$CH$_2$CH$_3$ (propylphenyl), —C$_6$H$_4$CH(CH$_3$)$_2$, —C$_6$H$_4$CH(CH$_2$)$_2$, —C$_6$H$_3$(CH$_3$)CH$_2$CH$_3$ (methylethylphenyl), —C$_6$H$_4$CH=CH$_2$ (vinylphenyl), —C$_6$H$_4$CH=CHCH$_3$, —C$_6$H$_4$C≡CH, —C$_6$H$_4$C≡CCH$_3$, naphthyl, and the monovalent group derived from biphenyl. The term "substituted aryl" refers to a monovalent group, having a aromatic carbon atom as the point of attachment, said carbon atom forming part of a six-membered aromatic ring structure wherein the ring atoms are all carbon, and wherein the monovalent group further has at least one atom independently selected from the group consisting of N, O, F, Cl, Br, I, Si, P, and S. Non-limiting examples of substituted aryl groups include the groups: —C$_6$H$_4$F, —C$_6$H$_4$Cl, —C$_6$H$_4$Br, —C$_6$H$_4$I, —C$_6$H$_4$OH, —C$_6$H$_4$OCH$_3$, —C$_6$H$_4$OCH$_2$CH$_3$, —C$_6$H$_4$OC(O)CH$_3$, C$_6$H$_4$NH$_2$, —C$_6$H$_4$NHCH$_3$, —C$_6$H$_4$N(CH$_3$)$_2$, —C$_6$H$_4$CH$_2$OH, —C$_6$H$_4$CH$_2$OC(O)CH$_3$, —C$_6$H$_4$CH$_2$NH$_2$, —C$_6$H$_4$CF$_3$, —C$_6$H$_4$CN, —C$_6$H$_4$CHO, —C$_6$H$_4$CHO, —C$_6$H$_4$C(O)CH$_3$, —C$_6$H$_4$C(O)C$_6$H$_5$, —C$_6$H$_4$CO$_2$H, —C$_6$H$_4$CO$_2$CH$_3$, —C$_6$H$_4$CONH$_2$, —C$_6$H$_4$CONHCH$_3$, and —C$_6$H$_4$CON(CH$_3$)$_2$.

An "isomer" of a first compound is a separate compound in which each molecule contains the same constituent atoms as the first compound, but where the configuration of those atoms in three dimensions differs.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylicacids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiary-butylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties*, Selection and Use (P. H. Stahl & C. G. Wermuth eds., Verlag Helvetica Chimica Acta, 2002), which is incorporated herein by reference.

"Prodrug" means a compound that is convertible in vivo metabolically into an inhibitor according to the present invention. In addition to esterified capsaicinoids, it is envisioned that other capsaicinoid prodrugs may be used with the present invention. The prodrug itself may or may not also have activity with respect to a given target protein or therapeutic effect. For example, a compound comprising a hydroxy group may be administered as an ester that is converted by hydrolysis in vivo to the hydroxy compound. As described herein, amyris alcohol prodrugs such as esterified amyris alcohols are provided for the treatment of diseases including herpes virus infection. Suitable esters that may be converted in vivo into hydroxy compounds include acetates, citrates, lactates, phosphates, tartrates, malonates, oxalates, salicylates, propionates, succinates, fumarates, maleates, methylene-bis-b-hydroxynaphthoates, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Amyris alcohols may be esterified using any of these approaches, and it is envisioned that these esterified amyris alcohols may be used with the present invention (e.g., to treat a herpesvirus infection, etc.) Similarly, a compound comprising an amine group may be administered as an amide that is converted by hydrolysis in vivo to the amine compound.

The term "saturated" when referring to a atom means that the atom is connected to other atoms only by means of single bonds.

The terms "subject" and "patient" includes humans, primates and other mammals.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers.

"Therapeutically effective amount" means that amount which, when administered to an animal for treating a disease, is sufficient to effect such treatment for the disease.

"Treatment" or "treating" includes: (1) inhibiting a disease in an subject or patient that is experiencing or displaying the pathology or symptomatology of the disease (i.e., arresting further development of the pathology and/or symptomatology), and (2) ameliorating the disease in a subject or patient that is experiencing or displaying the pathology or symptomatology of the diseased (i.e., reversing the pathology and/or symptomatology).

3. Synthesis of a Capsaicinoid Ester

The compounds esters of capsaicin can be prepared by any method known to those of ordinary skill in the art. For example, the compounds of the present invention are esters of capsaicin which are the constituents of capsicum. Various methods have been described in the literature pertaining to the synthesis of a number of esters of carboxylic acids and phenols (March's Advanced Organic Chemistry: Reactions, Mechanisms, and Structure, 5th Edition, by Michael B. Smith and Jerry March, John Wiley and Sons, Inc, 2001).

One method that has been utilized for efficient preparation of an esterified capsaicinoid of the present invention is through dissolution of the compound in methylene dichloride. Since capsaicin USP27 conatains >95% of capsaicins, to this solution slightly in excess of 1.1 mole equivalent of anhydrous triethylamine is added with stirring at room temperature and the mixture is kept around room temperature. To this solution slightly in excess of 1 mole equivalent of an acid chloride is added with stirring while keeping the temperature around 20-25° C. and the solution was refluxed for 5-6 hours and stirred for 12-16 hours at room temperature. The organic phase was washed 3-4 times with water and then 2 times with 7% sodium carbonate solution in a separating funnel to remove any acid present in the organic solution. The organic phase was then washed 2-3 times with dilute hydrochloric acid solution in a separating funnel to remove any amine present in the organic solution. The organic phase was then washed with equal amount of water three to four times until the pH of the aqueous phase is around 6-7. The organic phase was dried with anhydrous sodium sulfate overnight and the methylene dichloride was removed in a rotary evaporator under vacuum. The resultant oily or waxy material is called the ester capsaicin as all of the phenols present in capsaicin is converted into the corresponding ester.

F. Tricyclic Anti-Depressants

In various embodiments, a tricyclic antidepressant may be included in a pharmaceutical composition of the present invention. A non-limiting list of a tricyclic anti-depressant which may be used in the present invention includes amitriptyline, butriptyline, amoxapine, clomipramine, desipramine, dothiepin, imipramine, dibenzepin, iprindole, lofepramine, nortriptyline, opipramol, protriptyline, tianeptine, milnacipran and trimipramine.

II. Chronic Pain

Pharmaceutical compositions of the present invention, e.g., the combination of an NMDA antagonist, tramadol and gabapentin, may be used to treat moderate to severe pain arising from many different etiologies, including but not limited to, cancer pain and post-surgical pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis, degenerative joint diseases such as osteoarthritis, gout and ankylosing spondylitis, bursitis, burns, migraine headache, fibromyalgia syndrome, multiple sclerosis syndrome, trigeminal neuralgia, symptoms associated with diabetic neuropathy and injuries.

Further, the combination of NMDA antagonist, anticonvulsant and/or a tricyclic anti-depressant and tramadol or its analog is useful as an alternative to conventional non-steroidal anti-inflammatory drugs or combinations of NSAIDS with other drugs particularly where such non-steroidal anti-inflammatory drugs may be contraindicated such as in patients with peptic ulcers, gastritis, regional enteritis, ulcerative colitis, diverticulitis or with a recurrent history of gastrointestinal lesions, GI bleeding, coagulation disorders including anemia such as hypoprothrombinemia, haemophilia or other bleeding problems, kidney disease and in those prior to surgery or taking anticoagulants.

The present invention may be used to treat pain resulting from a variety of disorders, diseases, or injuries. In certain embodiments, the present invention may be used to treat neuropathic pain. The present invention may be used to treat chronic pain resulting from a variety of sources, including for example: musculoskeletal disorders such as osteoarthritis/degenerative joint disease/spondylosis, rheumatoid arthritis, lyme disease, reiter syndrome, disk herniation/facet osteoarthropathy, fractures/compression fracture of lumbar vertebrae, faulty or poor posture, fibromyalgia, polymyalgia rheumatica, mechanical low back pain, chronic coccygeal pain, muscular strains and sprains, pelvic floor myalgia (levator ani spasm), piriformis syndrome, rectus tendon strain, hernias (e.g., obturator, sciatic, inguinal, femoral, spigelian, perineal, umbilical), abdominal wall myofascial pain (trigger points), chronic overuse syndromes (e.g., tendinitis, bursitis); neurological disorders such as, brachial plexus traction injury, cervical radiculopathy, thoracic outlet syndrome, spinal stenosis, arachnoiditis syndrome, metabolic deficiency myalgias, polymyositis, neoplasia of spinal cord or sacral nerve, cutaneous nerve entrapment in surgical scar, postherpetic neuralgia (shingles), neuralgia (e.g., iliohypogastric, ilioinguinal, or genitofemoral nerves), polyneuropathies, polyradiculoneuropathies, mononeuritis multiplex, chronic daily headaches, muscle tension headaches, migraine headaches, temporomandibular joint dysfunction, temporalis tendonitis, sinusitis, atypical facial pain, trigeminal neuralgia, glossopharyngeal neuralgia, nervus intermedius neuralgia, sphenopalatine neuralgia, referred dental or temporomandibular joint pain, abdominal epilepsy, abdominal migraine, urologic disorders, bladder neoplasm, chronic urinary tract infection, interstitial cystitis, radiation cystitis, recurrent cystitis, recurrent urethritis, urolithiasis, uninhibited bladder contractions (detrusor-sphincter dyssynergia), urethral diverticulum, chronic urethral syndrome, urethral carbuncle, prostatitis, urethral stricture, testicular torsion, peyronie disease; gastrointestinal disorders such as chronic visceral pain syndrome, gastroesophageal reflux, peptic ulcer disease, pancreatitis, chronic intermittent bowel obstruction, colitis, chronic constipation, diverticular disease, inflammatory bowel disease, irritable bowel syndrome; reproductive disorders (extrauterine) such as endometriosis, adhesions, adnexal cysts, chronic ectopic pregnancy, chlamydial endometritis or salpingitis, endosalpingiosis, ovarian retention syndrome (residual ovary syndrome), ovarian remnant syndrome, ovarian dystrophy or ovulatory pain, pelvic congestion syndrome, postoperative peritoneal cysts, residual accessory ovary, subacute salpingo-oophoritis, tuberculous salpingitis; reproductive disorders (uterine) such as adenomyosis, chronic endometritis, atypical dysmenorrhea or ovulatory pain, cervical stenosis, endometrial or cervical polyps, leiomyomata, symptomatic pelvic relaxation (genital prolapse), intrauterine contraceptive device; psychological disorders such as bipolar personality disorders, depression, porphyria, sleep disturbances; and other conditions such as cardiovascular disease (e.g., angina), peripheral vascular disease and chemotherapeutic, radiation, or surgical complications.

III. Dosages

Preferred embodiments of the present invention are pain relieving preparations for oral administration that provide a combination of a NMDA antagonist or a pharmaceutically acceptable salt thereof, an anticonvulsant (e.g., gabapentin or a gabapentin analog) and/or a tricyclic anti-depressant or a pharmaceutically acceptable salt thereof, and tramadol or a tramadol analog or a pharmaceutically acceptable salt thereof. Reduced dosages of the active ingredients are preferably used in the present invention, since the combination of these drugs can, in various embodiments, synergize to provide a reduction in pain, and the amounts of the drugs provided are preferably minized to reduce or eliminate any possible side effects.

For example, dosage levels of an NMDA antagonist on the order of from about 0.3 mg to about 3 mg per kilogram of body weight per day and anticonvulsant (e.g., gabapentin) and/or a tricyclic anti-depressant on the order of from about 0.05 mg to about 3 mg per kilogram of body weight can be therapeutically effective in combination with tramadol or its analog. Alternatively, about 10 mg to about 200 mg per patient per day of a NMDA antagonist and about 5 mg to about 300 mg per patient per day of anticonvulsant and/or a tricyclic anti-depressant may be administered in combination with tramadol or its analog. For example, chronic pain may be effectively treated by the administration of from about 0.3 to 3 mg of the NMDA antagonist per kilogram of body weight per day, or alternatively about 30 mg to about 300 mg per patient per day.

The amount of NMDA antagonist that may be combined with the carrier materials to produce a single dosage form having NMDA antagonist, anticonvulsant and/or a tricyclic anti-depressant and tramadol or its analog in combination will vary depending upon the patient and the particular mode of administration. For example, a formulation intended for the oral administration of humans may contain from 10 mg to 300 mg of NMDA antagonist compounded with an appropriate and convenient amount of carrier material that may vary from about 5 to about 95 percent of the total composition. Unit dosages will generally contain between from about 10 mg to about 100 mg of a NMDA antagonist.

Dextromethorphan may be included in a pharmaceutical composition (e.g., an oral formulation such as a tablet or capsule) of the present invention in an amount of from about 10 mg to about 200 mg, from about 10 mg to about 150 mg, from about 15 mg to about 100 mg, from about 25 mg to about 75 mg, from about 30 mg to about 60 mg, from about 34 mg to about 51 mg, or any range derivable therein. The composition may, e.g., be administered to a patient 1, 2, or 3 times per day.

Tramadol or its analog can be provided in a sustained release oral dosage form with as the therapeutically active analgesic in an amount from about 25 mg to about 400 mg tramadol hydrochloride. Preferably, less than 400 mg tramadol per day are used with the present invention. In certain embodiments, from about 10 mg to about 200 mg, from about 10 mg to about 100 mg, from about 15 mg to about 60 mg, from about 20 mg to about 60 mg, from about 25 mg to about 50 mg, from about 28.5 mg to about 40 mg, or any range derivable therein of tramadol or a tramadol analog may be included in a pharmaceutical composition (e.g., an oral composition such as a tablet or capsule) of the present invention. The composition may, e.g., be administered to a patient 1, 2, or 3 times per day.

Alternatively, the dosage form may contain molar equivalent amounts of other tramadol salts or of the tramadol base. The dosage form may contain a mixture of tramadol and a derivative of tramadol to provide a substantially equivalent therapeutic effect.

Preferred combinations of the invention comprise an effective amount of a NMDA antagonist selected from the group consisting of dextromethorphan, ketamine and amantidine, an effective amount tramadol or its analog selected from the group consisting of tramadol, its metabolites and analogs and an effective amount of anticonvulsant and/or a tricyclic anti-depressant.

The amount of anticonvulsant (e.g., gabapentin or pregabalin) in the composition will be an amount sufficient to further enhance analgesia or to hasten its onset. In humans, this amount will typically be from about 10 to about 3600 mg (preferably 20 to 1000 mg), an amount generally sufficient to both hasten onset and enhance analgesia. The daily dosage of anticonvulsant again will generally not exceed 3600 mg. Greater amounts can be used if tolerated by the patient; however, as shown in the below examples, lower dosages can be effective for the treatment of pain and are generally preferable in the interest of minimizing any possible side effects.

Gabapentin is preferably be included in a pharmaceutical composition of the present invention in an amount less than 3600 mg, more preferably, less than 1800 mg, and even more preferably less than 1000 mg. In various embodiments, from about 10 mg to about 200 mg, from about 15 mg to about 150 mg, from about 20 mg to about 100 mg, from about 30 mg to about 90 mg, or any range derivable therein of gabapentin may be included in a pharmaceutical composition of the present invention.

The amount of tricyclic anti-depressant in the composition will be an amount sufficient to further enhance analgesia or to hasten its onset. In humans, this amount will typically be from about 1 to about 1000 mg (preferably 5 to 300 mg), an amount generally sufficient to both hasten onset and enhance analgesia. The daily dosage of tricyclic anti-depressant again will generally not exceed 300 mg. Of course, greater amounts can be used if tolerated by the patient.

The amount of capsaicin palmitate in the composition will be an amount sufficient to further enhance analgesia or to hasten its onset. In humans, this amount will typically be from about 1 to about 100 mg (preferably 5 to 30 mg), an amount generally sufficient to both hasten onset and enhance analgesia. The daily dosage of capsaicin palmitate again will generally not exceed 100 mg. Of course, greater amounts can be used if tolerated by the patient.

In certain preferred embodiments according to the present invention, an oral dosage form is provided which includes the following tramadol or its analog/NMDA antagonist/anticonvulsant combinations: Tramadol 35 mg plus 45 mg dextromethorphan plus 90 mg gabapentin; tramadol 35 mg plus 45 mg dextromethorphan plus 180 mg gabapentin; tramadol 35 mg plus 45 mg dextromethorphan plus 45 mg gabapentin or 50 mg of tramadol plus 30 mg of dextromethorphan plus 90 mg gabapentin.

In another preferred embodiments according to the present invention, an oral dosage form is provided which includes the following tramadol or its analog/NMDA antagonist/anticonvulsant/capsaicin palmitate combinations: Tramadol 35 mg plus 45 mg dextromethorphan plus 90 mg gabapentin plus 5.4 mg of capsaicin palmitate; tramadol 35 mg plus 45 mg dextromethorphan plus 180 mg gabapentin plus 5.4 mg of capsaicin palmitate; tramadol 35 mg plus 45 mg dextromethorphan plus 45 mg gabapentin plus 10.8 mg of capsaicin palmitate; 50 mg of tramadol plus 30 mg of dextromethorphan plus 90 mg gabapentin plus 10.8 mg of capsaicin palmitate.

In certain preferred embodiments according to the present invention, an oral dosage form is provided which includes the following tramadol or its analog/NMDA antagonist/tricyclic antidepressant combinations: Tramadol 35 mg plus 45 mg dextromethorphan plus 10 mg amitriptyline or milnacipran; tramadol 35 mg plus 45 mg dextromethorphan plus 5 mg amitriptyline or milnacipran; or 50 mg of tramadol plus 30 mg of dextromethorphan plus 10 mg amitriptyline or milnacipran.

In certain preferred embodiments according to the present invention, an oral dosage form is provided which includes the following tramadol or its analog/NMDA antagonist/anticonvulsant and tricyclic antidepressant combinations: Tramadol 35 mg plus 45 mg dextromethorphan plus 90 mg gabapentin plus 10 mg amitriptyline or milnacipran; tramadol 35 mg plus 45 mg dextromethorphan plus 45 mg gabapentin plus 5 mg amitriptyline or milnacipran; tramadol 35 mg plus 45 mg dextromethorphan plus 45 mg gabapentin plus 10 mg amitriptyline or milnacipran; or 35 mg of tramadol plus 30 mg of dextromethorphan plus 90 mg gabapentin plus 10 mg amitriptyline or milnacipran.

In another preferred embodiments according to the present invention, an oral dosage form is provided which includes the following tramadol or its analog/NMDA antagonist/tricyclic antidepressant/capsaicin palmitate combinations: Tramadol 35 mg plus 45 mg dextromethorphan plus 10 mg amitriptyline or milnacipran plus 5.4 mg of capsaicin palmitate; tramadol 35 mg plus 45 mg dextromethorphan plus 10 mg amitriptyline or milnacipran plus 10.8 mg of capsaicin palmitate; tramadol 35 mg plus 30 mg dextromethorphan plus 10 mg amitriptyline or milnacipran plus 10.8 mg of capsaicin palmitate; 50 mg of tramadol plus 30 mg of dextromethorphan plus 10 mg amitriptyline or milnacipran plus 10.8 mg of capsaicin palmitate.

The dosage administered will of course vary depending upon known factors such as the pharmacodynamic characteristics of each agent of the combination and its mode and route of administration and upon the age, health and weight of the patient. The dosage will also depend upon the nature and extent of symptoms, concurrent treatment, if any, frequency of treatment and the desired result. A composition comprising any of the above identified combinations of tramadol or its analog, gabapentin or analog of gabapentin and NMDA antagonist may be administered in divided doses ranging from 2 to 6 times per day or in a sustained release form that will provide a rate of release effective to attain the desired results.

The optimal NMDA antagonist to tramadol or its analog ratios can be determined by standard assays well known in the art for determining opiate and analgesic activity. For example, the phenyl-p-benzoquinone test may be used to establish analgesic effectiveness. The phenyl-p-benzoquinone induced writhing test in mice as described in Blumberg et al, 1965, Proc. Soc. Exp. Med. 118:763-766, hereby incorporated by reference, and known modifications thereof, is a standard procedure which may be used for detecting and comparing the analgesic activity of different classes of analgesic drugs with a good correlation with human analgesic activity. Data for the mouse, as presented in an isobologram, can be translated to other species where the orally effective analgesic dose of the individual compounds are known or can be estimated.

IV. Pharmaceutical Preparations

The present invention encompasses immediate release dosage forms of an effective analgesic amount of dextromethorphan, gabapentin or an anlog of gabapentin and tramadol or its analog combination. An immediate release dosage form may be formulated as a tablet, capsule, or a multi-particulate oral preparation that may be encapsulated. Other immediate release dosage forms known in the art can be employed. In certain embodiments, the pharmaceutical preparations of the invention may be administered orally; in other embodiments, the pharmaceutical preparation may be administered parenterally, intravenously, via inhalation, etc.

Compositions of the invention present the opportunity for obtaining relief from moderate to severe pain. Due to the synergistic and/or additive effects provided by the inventive combination of tramadol or its analog, anticonvulsant and/or a tricyclic anti-depressant and NMDA antagonist, it may be possible to use reduced dosages of each of NMDA antagonist and tramadol or its analog. By using lesser amounts of other or both drugs, the side effects associated with each may be reduced in number and degree. Moreover, the inventive combination avoids side effects to which some patients are particularly sensitive.

The sustained release dosage forms of the present invention generally achieve and maintain therapeutic levels substantially without significant increases in the intensity and/or degree of concurrent side effects, such as nausea, vomiting, seizures or drowsiness, which are often associated with high blood levels of tramadol or its analogs. There is also evidence to suggest that the use of the present dosage forms leads to a reduced risk of drug addiction.

The combination of NMDA antagonist, anticonvulsant and/or a tricyclic anti-depressant and tramadol or its analog may be formulated to provide for an increased duration of analgesic action allowing once daily dosing. Similarly, the combination of NMDA antagonist, capsaicin or an ester of capsaicin, anticonvulsant and/or a tricyclic anti-depressant and tramadol or its analog may be formulated to provide for an increased duration of analgesic action allowing once daily dosing. These formulations, at comparable daily dosages of conventional immediate release drug, are associated with a lower incidence in severity of adverse drug reactions and can also be administered at a lower daily dose than conventional oral medication while maintaining pain control.

The combination of NMDA antagonist, anticonvulsant and/or a tricyclic anti-depressant and tramadol or its analog or the combination of NMDA antagonist, anticonvulsant and/or a tricyclic anti-depressant, capsaicin or an ester of capsaicin and tramadol or its analog can be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. Suitable pharmaceutically acceptable carriers include but are not limited to water, salt solutions, alcohols, gum arabic, vegetable oils, benzyl alcohols, polyethylene glycols, gelate, carbohydrates such as lactose, amylose or starch, magnesium stearate talc, silicic acid, viscous paraffin, perfume oil, fatty acid monoglycerides and diglycerides, pentaerythritol fatty acid esters, hydroxymethylcellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They can also be combined where desired with other active agents, e.g., other analgesic agents. For parenteral application, particularly suitable are oily or aqueous solutions, as well as suspensions, emulsions, or implants, including suppositories. For oral application, particularly suitable are tablets, troches, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients which are suitable for the manufacture of tablets. Such excipients include, for example an inert diluent such as lactose, granulating and disintegrating agents such as cornstarch, binding agents such as starch, and lubricating agents such as magnesium stearate. The tablets may be uncoated or they may be coated by known techniques for elegance or to delay release of the active ingredients. Formulations for oral use may also be presented as hard gelatin capsules wherein the active ingredient is mixed with an inert diluent.

Aqueous suspensions that contain the aforementioned combinations of drugs and that such a mixture has one or more excipients suitable as suspending agents, for example pharmaceutically acceptable synthetic gums such as hydroxypropylmethylcellulose or natural gums. Oily suspensions may be formulated by suspending the aforementioned combinations of drugs in a vegetable oil or mineral oil. The oily suspensions may contain a thickening agent such as bees' wax or cetyl alcohol. A syrup, elixir, or the like can be used wherein a sweetened vehicle is employed. Injectable suspensions may also be prepared, in which case appropriate liquid carriers, suspending agents and the like may be employed. It is also possible to freeze-dry the active compounds and use the obtained lyophilized compounds, for example, for the preparation of products for injection.

The method of treatment and pharmaceutical formulations of the present invention may further include one or more drugs in addition to a NMDA antagonist, an anticonvulsant and/or a tricyclic anti-depressant and tramadol or its analog, which additional drug(s) may or may not act synergistically therewith. Examples of such additional drugs include, but not limited to, vanilloid receptor antagonists, NSAIDs, including ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam or isoxicam, acetaminophen and the like.

A. Controlled Release Dosage Forms

The NMDA antagonist, anticonvulsant and/or a tricyclic anti-depressant and tramadol or its analog combination or the NMDA antagonist, anticonvulsant and/or a tricyclic anti-depressant, capsaicin or an ester of capsaicin and tramadol or its analog combination can be formulated as a controlled or sustained release oral formulation in any suitable tablet, coated tablet or multiparticulate formulation known to those skilled in the art. The sustained release dosage form may optionally include a sustained released carrier which is incorporated into a matrix along with tramadol or its analog, or which is applied as a sustained release coating. In various embodiments, the pharmaceutical composition may be comprised in liposomes.

The sustained release dosage form may include the tramadol or its analog in sustained release form and the NMDA antagonist and anticonvulsant and/or a tricyclic anti-depressant in sustained release form or in immediate release form. The NMDA antagonist and anticonvulsant and/or a tricyclic anti-depressant may be incorporated into the sustained release matrix along with tramadol or its analog, incorporated into the sustained release coating; incorporated as a separated sustained release layer or immediate release layer, or may be incorporated as a powder, granulation, etc., in a gelatin capsule with the substrates of the present invention. Alternatively, the sustained release dosage form may have the NMDA antagonist in sustained release form and the tramadol or its analog and anticonvulsant and/or a tricyclic anti-depressant in sustained release form or immediate release form.

An oral dosage form according to the invention may be provided as, for example, granules, spheroids, beads, and pellets or pills. These formulations are hereinafter collectively referred to as "multiparticulates" and/or particles. An amount of the multiparticulates that is effective to provide the desired dose of tramadol or its analog over time may be placed in a capsule or may be incorporated in any other suitable oral solid form.

In one preferred embodiment of the present invention, the sustained release dosage form comprises such particles containing or comprising the active ingredient, wherein the particles have diameter from about 0.1 mm to about 2.5 mm, preferably from about 0.5 mm to about 2 mm.

In certain embodiments, the particles comprise normal release matrixes containing the tramadol or its analog with or without the NMDA antagonist and anticonvulsant and/or a tricyclic anti-depressant. These particles are then coated with the sustained release carrier. In embodiments where the NMDA antagonist and anticonvulsant and/or a tricyclic anti-depressant are immediately released, the NMDA antagonist and anticonvulsant and/or a tricyclic anti-depressant may be included in separate normal release matrix particles, or may be co-administered in a different immediate release composition which is either enveloped within a gelatin capsule or is administered separately. In other embodiments, the particles comprise inert beads that are coated with tramadol or its analog with or without the NMDA antagonist and anticonvulsant and/or a tricyclic anti-depressant. Thereafter, a coating comprising the sustained release carrier is applied onto the beads as an overcoat.

The particles are preferably film coated with a material that permits release of the tramadol or its analog or its salt, and if desired, the NMDA antagonist and anticonvulsant and/or a tricyclic anti-depressant at a sustained rate in an aqueous medium. The film coat is chosen so as to achieve, in combination with the other stated properties, a desired in vivo release rate. The sustained release coating formulations of the present invention should be capable of producing a strong, continuous film that is smooth and elegant, capable of supporting pigments and other coating additives, non-toxic, inert, and tack free.

B. Coatings

The dosage forms of the present invention may optionally be coated with one or more materials suitable for the regulation of release or for the protection of the formulation. In one embodiment, coatings are provided to permit either pH dependent or pH independent release, e.g., when exposed to gastrointestinal fluid. A pH dependent coating serves to release the tramadol or its analog in desired areas of the gastro-intestinal (GI) tract, e.g., the stomach or small intestine, such that an absorption profile is provided which is capable of providing at least about twelve hour and preferably up to twenty four hour analgesia to a patient. When a pH independent coating is desired, the coating is designed to achieve optimal release regardless of pH changes in the environmental fluid, e.g., the GI tract. It is also possible to formulate compositions which release a portion of the dose in one desired area of the GI tract, e.g., the stomach, and release the remainder of the dose in another area of the GI tract, e.g., the small intestine.

Formulations according to the invention that utilize pH dependent coatings to obtain formulations may also impart a repeat-action or pulsatile release effect whereby unprotected drug is coated over the enteric coat and is released in the stomach, while the remainder, being protected by the enteric coating, is released further down the gastrointestinal tract. Coatings which are pH dependent may be used in accordance with the present invention include shellac, cellulose acetate phthalate (CAP), polyvinyl acetate phthalate (PVAP), hydroxypropylmethylcellulose phthalate, and methacrylic acid ester copolymers, zein, and the like.

The substrate (e.g., tablet core bead, matrix particle) containing the tramadol or its analog (with or without the NMDA antagonist and anticonvulsant and/or a tricyclic anti-depressant) is coated with a hydrophobic material selected from (i) an alkylcellulose; (ii) an acrylic polymer, or (iii) mixtures thereof. The coating may be applied in the form of an organic or aqueous solution or dispersion. The coating may be applied to obtain a weight gain from about 2 to about 25% of the substrate in order to obtain a desired sustained release profile. Such formulations are described in detail in U.S. Pat. Nos. 5,273,760 and 5,286,493, hereby incorporated by reference in their entirety.

Other examples of sustained release formulations and coatings that may be used in accordance with the present invention include U.S. Pat. Nos. 5,324,351, 5,356,467, and 5,472,712, hereby incorporated by reference in their entirety.

C. Alkylcellulose Polymers

Cellulosic materials and polymers, including alkylcelluloses, provide hydrophobic materials well suited for coating the beads according to the invention. Simply by way of example, one preferred alkylcellulosic polymer is ethylcellulose, although the artisan will appreciate that other cellulose and/or alkylcellulose polymers may be readily employed, singly or in any combination, as all or part of a hydrophobic coating according to the invention.

One commercially available aqueous dispersion of ethylcellulose is sold as Aquacoat™ (FMC Corp., Philadelphia, Pa., U.S.A.). Aquacoat™ is prepared by dissolving the ethylcellulose in a water immiscible organic solvent and then emulsifying the same in water in the presence of a surfactant and a stabilizer. After homogenization to generate submicron droplets, the organic solvent is evaporated under vacuum to form a pseudolatex. The plasticizer is not incorporated in the pseudo-latex during the manufacturing phase. Thus, prior to using the same as a coating, it is necessary to intimately mix the Aquacoat™ with a suitable plasticizer prior to use.

Another aqueous dispersion of ethylcellulose is commercially available as Surelease™ (Colorcon, Inc., West Point, Pa., U.S.A.). This product is prepared by incorporating plasticizer into the dispersion during the manufacturing process. A hot melt of a polymer containing for example a plasticizer such as dibutyl sebacate, and a stabilizer such as oleic acid is prepared as a homogeneous mixture, which is then diluted with an alkaline solution to obtain an aqueous dispersion which can be applied directly onto substrates.

D. Acrylic Polymers

The hydrophobic material comprising the controlled release coating is a pharmaceutically acceptable acrylic polymer, including but not limited to acrylic acid and methacrylic acid copolymers, methyl methacrylate copolymers, ethoxyethyl methacrylates, cyanoethyl methacrylate, poly(acrylic acid), poly(methacrylic acid), methacrylic acid alkylamide copolymer, poly(methyl methacrylate), polymethacrylate, poly(methyl methacrylate) copolymer, polyacrylamide, aminoalkyl methacrylate copolymer, poly(methacrylic acid anhydride), and glycidyl methacrylate copolymers. The acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In order to obtain a desirable dissolution profile, it may be necessary to incorporate two or more ammonio methacrylate copolymers having differing physical properties, such as different molar ratios of the quaternary ammonium groups to the neutral methacrylic esters.

Certain methacrylic acid ester type polymers are useful for preparing pH dependent coatings that may be used in accordance with the present invention. For example, there are a family of copolymers synthesized from diethylaminoethyl methacrylate and other neutral methacrylic esters, also known as methacrylic acid copolymer or polymeric methacrylates, commercially available as Eudragit™ from Rohm Tech, Inc. There are several different types of Eudragit™. For example Eudragit™ E is an example of a methacrylic acid copolymer that swells and dissolves in acidic media. Eudragit™ L is a methacrylic acid copolymer which does not swell at about pH <5.7 and is soluble at about pH >6. Eudragit™ S does not swell at about pH <6.5 and is soluble at about pH >7. Eudragit™ L and Eudragit™ S are water swellable, and the amount of water absorbed by these polymers is pH dependent. However, dosage forms coated with Eudragit™ L and S are pH independent.

The acrylic coating comprises a mixture of two acrylic resin lacquers commercially available from Rohm Pharma under the Tradenames Eudragit™ L30D and Eudragit™ S30D, respectively. Eudragit™ L30D and Eudragit™ S30D are copolymers of acrylic and methacrylic esters with a low content of quaternary ammonium groups, the molar ratio of ammonium groups to the remaining neutral methacrylic esters being 1:20 in Eudragit™ L30D and 1:40 in Eudragit™ S30D. The mean molecular weight is about 150,000. The code designations RL (high permeability) and RS (low permeability) refer to the permeability properties of these agents. Eudragit™ RL/RS mixtures are insoluble in water and in digestive fluids. However, coatings formed from the same are swellable and permeable in aqueous solutions and digestive fluids.

The Eudragit™ RL/RS dispersions of the present invention may be mixed together in any desired ratio in order to ultimately obtain a sustained release formulation having a desirable dissolution profile. Desirable sustained release formulations may be obtained, for instance, from a retardant coating derived from 100% Eudragit™ RL, 50% Eudragit™ RL and 50% Eudragit™ RS, and 10% Eudragit™ RL Eudragit™ 90% RS. Of course, one skilled in the art will recognize that other acrylic polymers may also be used, such as, for example, Eudragit™ L.

E. Plasticizers

In the present invention where the coating comprises an aqueous dispersion of a hydrophobic material, the inclusion of an effective amount of a plasticizer in the aqueous dispersion of hydrophobic material will further improve the physical properties of the sustained release coating. For example, because ethylcellulose has a relatively high glass transition temperature and does not form flexible films under normal coating conditions, it is preferable to incorporate a plasticizer into an ethylcellulose coating containing sustained release coating before using the same as a coating material. Generally, the amount of plasticizer included in a coating solution is based on the concentration of the film-former, e.g., most often from about 1 to about 50 percent by weight of the film-former. Concentration of the plasticizer, however, can only be properly determined after careful experimentation with the particular coating solution and method of application.

Examples of suitable plasticizers for ethylcellulose include water insoluble plasticizers such as dibutyl sebacate, diethyl phthalate, triethyl citrate, tributyl citrate, and triacetin, although it is possible that other water-insoluble plasticizers, such as acetylated monoglycerides, phthalate esters, castor oil, etc., may be used. Triethyl citrate is an especially preferred plasticizer for the aqueous dispersions of ethyl cellulose of the present invention.

Examples of suitable plasticizers for the acrylic polymers of the present invention include, but are not limited to citric acid esters such as triethyl citrate, tributyl citrate, dibutyl phthalate, and possibly 1,2-propylene glycol. Other plasticizers that have proved to be suitable for enhancing the elasticity of the films formed from acrylic films such as Eudragit™ RL/RS lacquer solutions include polyethylene glycols, propylene glycol, diethyl phthalate, castor oil, and triacetin. Triethyl citrate is an especially preferred plasticizer for the aqueous dispersions of ethyl cellulose of the present invention.

It has further been found that the addition of a small amount of talc reduces the tendency of the aqueous dispersion to stick during processing, and acts as a polishing agent.

F. Processes for Preparing Coated Beads

When the aqueous dispersion of hydrophobic material is used to coat inert pharmaceutical beads such as nu-pariel 18/20 beads, a plurality of the resultant stabilized solid controlled release beads may thereafter be placed in a gelatin capsule in an amount sufficient to provide an effective controlled release dose when ingested and contacted by an environmental fluid, e.g., gastric fluid or dissolution media.

The stabilized controlled release bead formulations of the present invention slowly release the therapeutically active agent, e.g., when ingested and exposed to gastric fluids, and then to intestinal fluids. The controlled release profile of the formulations of the invention can be altered, for example, by varying the amount of overcoating with the aqueous dispersion of hydrophobic material, altering the manner in which the plasticizer is added to the aqueous dispersion of hydrophobic material, by varying the amount of plasticizer relative to hydrophobic material, by the inclusion of additional ingredients or excipients, by altering the method of manufacture, etc. The payload release profile of the product may also be modified by increasing or decreasing the thickness of the retardant coating.

Spheroids or beads coated with a therapeutically active agent are prepared, e.g., by dissolving the therapeutically active agent in water and then spraying the solution onto a substrate, for example, nu pariel 18/20 beads, using a Wuster insert. Optionally, additional ingredients are also added prior to coating the beads in order to assist the binding of the tramadol or its analog to the beads, and/or to color the solution, etc. For example, a product that includes hydroxypropylmethylcellulose, etc. with or without a colorant, such as Opadry™, commercially available from Colorcon, Inc., may be added to the solution and the solution mixed for about 1 hour prior to application of the same onto the beads. The resultant coated substrate, in this example beads, may then be optionally overcoated with a barrier agent, to separate the therapeutically active agent from the hydrophobic controlled release coating. An example of a suitable barrier agent is one that comprises hydroxypropylmethylcellulose. However, any film former known in the art may be used. It is preferred that the barrier agent does not affect the dissolution rate of the final product.

The beads may then be overcoated with an aqueous dispersion of the hydrophobic material. The aqueous dispersion of hydrophobic material preferably further includes an effective amount of plasticizer, e.g. triethyl citrate. Pre-formulated aqueous dispersions of ethylcellulose, such as Aquacoat™ or Surelease™, may be used. If Surelease™ is used, it is not necessary to separately add a plasticizer. Alternatively, pre-formulated aqueous dispersions of acrylic polymers such as Eudragit™ can be used.

The coating solutions of the present invention preferably contain, in addition to the film former, plasticizer, and solvent system such as water and a colorant to provide elegance and product distinction. Color may be added to the solution of the therapeutically active agent instead, or in addition to the aqueous dispersion of hydrophobic material. For example, color be added to Aquacoat™ via the use of alcohol or propylene glycol based color dispersions, milled aluminum lakes and opacifiers such as titanium dioxide by adding color with shear to water soluble polymer solution and then using low shear to the plasticized Aquacoat™ Alternatively, any suitable method of providing color to the formulations of the present invention may be used. Suitable ingredients for providing color to the formulation when an aqueous dispersion of an acrylic polymer is used include titanium dioxide and color pigments, such as iron oxide pigments. The incorporation of pigments, may, however, increase the release retarding effect of the coating.

The plasticized aqueous dispersion of hydrophobic material may be applied onto the substrate comprising the therapeutically active agent by spraying using any suitable spray equipment known in the art. In a preferred method, a Wurster fluidized bed system is used in which an air jet, injected from underneath, fluidizes the core material and effects drying while the acrylic polymer coating is sprayed on. A sufficient amount of the aqueous dispersion of hydrophobic material to obtain a predetermined controlled release of said therapeutically active agent when said coated substrate is exposed to aqueous solutions, such as gastric fluid, is preferably applied, taking into account the physical characteristics of the therapeutically active agent, the manner of incorporation of the plasticizer, etc. After coating with the hydrophobic material, a further overcoat of a film-former, such as Opadry™, is optionally applied to the beads. This overcoat is provided, if at all, in order to substantially reduce agglomeration of the beads.

The release of the therapeutically active agent from the controlled release formulation of the present invention can be further influenced and adjusted to a desired rate by the addition of one or more release modifying agents. Controlled release may be achieved in the alternative by providing one or more passageways through the coating through which the drug or a solution of the drug can diffuse. The ratio of hydrophobic material to water soluble material is determined by, among other factors, the release rate required to produce the desired therapeutic effect and the solubility characteristics of the materials selected.

The release modifying agents which function as pore formers may be organic or inorganic, and include materials that can be dissolved, extracted or leached from the coating in the environment of use. The pore-formers may comprise one or more hydrophilic materials such as hydroxypropylmethylcellulose.

The sustained release coatings of the present invention can also include erosion promoting agents such as starches and gums.

The sustained release coatings of the present invention can also include materials useful for making microporous lamina in the environment of use, such as polycarbonates comprised of linear polyesters of carbonic acid in which carbonate groups reoccur in the polymer chain. The release modifying agent may also comprise a semi-permeable polymer.

The release modifying agent can be preferably selected from hydroxypropylmethylcellulose, lactose, metal stearates, and mixtures of any of the foregoing.

The sustained release coatings of the present invention may also include an exit means comprising at least one passageway, orifice, or the like. The passageway may be formed by such methods as those disclosed in U.S. Pat. Nos. 3,845,770, 3,916,889, 4,063,064 and 4,088,864, all of which are hereby incorporated by reference. The passageway can have any shape such as round, triangular, square, elliptical, irregular, etc.

G. Matrix Bead Formulations

The controlled release formulation is achieved via a matrix having a controlled release coating as set forth above. The present invention may also utilize a controlled release matrix that affords in vitro dissolution rates of the tramadol or its analog within the preferred ranges and that releases the tramadol or its analog in a pH dependent or pH independent manner. The materials suitable for inclusion in a controlled release matrix will depend on the method used to form the matrix.

For example, a matrix in addition to the tramadol or its analog and, optionally, a NMDA antagonist and an anticonvulsant and/or a tricyclic anti-depressant may include:

Hydrophilic and/or hydrophobic materials, such as gums, cellulose ethers, acrylic resins, protein derived materials; the list is not meant to be exclusive, and any pharmaceutically acceptable hydrophobic material or hydrophilic material which is capable of imparting controlled release of the active agent and which melts or softens to the extent necessary to be extruded may be used in accordance with the present invention.

Digestible, long chain ($C_8$ to $C_{50}$, especially $C_{12}$ to $C_{40}$), substituted or unsubstituted hydrocarbons, such as fatty acids, fatty alcohols, glyceryl esters of fatty acids, mineral and vegetable oils and waxes, and stearyl alcohol; and polyalkylene glycols.

Of these polymers, acrylic polymers, especially Eudragit™, RSPO, the cellulose ethers, especially hydroxyalkylcelluloses and carboxyalkylcelluloses, are preferred. The oral dosage form may contain between 1% and 80% by weight of at least one hydrophilic or hydrophobic material.

When the hydrophobic material is a hydrocarbon, the hydrocarbon preferably has a melting point of between 25 and 90 carbon atoms. Of the long chain hydrocarbon materials, fatty aliphatic alcohols are preferred. The oral dosage form may contain up to 60% (by weight) of at least one digestible, long chain hydrocarbon.

Preferably, the oral dosage form contains up to 60% by weight of at least one polyalkylene glycol.

The hydrophobic material is preferably selected from the group consisting of alkylcelluloses, acrylic and methacrylic acid polymers and copolymers, shellac, zein, hydrogenated castor oil, hydrogenated vegetable oil, or mixtures thereof. In certain preferred embodiments of the present invention, the hydrophobic material is a pharmaceutically acceptable acrylic polymer, including but not limited to acrylic acid and methacrylic acid copolymers, methyl methacrylate, methyl methacrylate copolymers, ethoxyethyl methacrylates, cynaoethyl methacrylate, aminoalkyl methacrylate copolymer, polyacrylic acid, polymethacrylic acid, methacrylic acid alkylamine copolymer, polymethyl methacrylate, polymethacrylic acid anhydride, polymethacrylate, polyacrylamide, poly(methacrylic acid anhydride), and glycidyl methacrylate copolymers. In other embodiments, the hydrophobic material is selected from materials such as hydroxyalkylcelluloses such as hydroxypropylmethylcellulose and mixtures of the foregoing.

Preferred hydrophobic materials are water-insoluble with more or less pronounced hydrophilic and/or hydrophobic trends. Preferably, the hydrophobic materials useful in the invention have a melting point from about 30 to about 200° C., preferably from about 45 to about 90° C. Specifically, the hydrophobic material may comprise natural or synthetic waxes, fatty alcohols such as lauryl, myristyl, stearyl, cetyl or preferably cetostearyl alcohol, fatty acids, including but not limited to fatty acid esters, fatty acid glycerides (mono-, di-, and tri-glycerides), hydrogenated fats, hydrocarbons, normal waxes, stearic aid, stearyl alcohol and hydrophobic and hydrophilic materials having hydrocarbon backbones. Suitable waxes include, for example, beeswax, glycowax, castor wax and carnauba wax. For purposes of the present invention, a wax-like substance is defined as any material that is normally solid at room temperature and has a melting point of from about 30 to about 100° C.

Suitable hydrophobic materials which may be used in accordance with the present invention include digestible, long chain ($C_8$ to $C_{50}$, especially $C_{12}$ to $C_{40}$), substituted or unsubstituted hydrocarbons, such as fatty acids, fatty alcohols, glyceryl esters of fatty acids, mineral and vegetable oils and natural and synthetic waxes. Hydrocarbons having a melting point of between 25 and 90° C. are preferred. Of the long chain hydrocarbon materials, fatty (aliphatic) alcohols are preferred in certain embodiments. The oral dosage form may contain up to 60% by weight of at least one digestible, long chain hydrocarbon.

Preferably, a combination of two or more hydrophobic materials is included in the matrix formulations. If an additional hydrophobic material is included, it is preferably selected from natural and synthetic waxes, fatty acids, fatty alcohols, and mixtures of the same. Examples include beeswax, carnauba wax, stearic acid and stearyl alcohol. This list is not meant to be exclusive.

One particular suitable matrix comprises at least one water soluble hydroxyalkyl cellulose, at least one $C_{12}$ to $C_{36}$, preferably $C_{14}$ to $C_{22}$, aliphatic alcohol and, optionally, at least one polyalkylene glycol. The at least one hydroxyalkyl cellulose is preferably a hydroxy ($C_1$ to $C_6$) alkyl cellulose, such as hydroxypropylcellulose, hydroxypropylmethylcellulose and, especially, hydroxyethylcellulose. The amount of the at least one hydroxyalkyl cellulose in the present oral dosage form will be determined, inter alia, by the precise rate of tramadol or its analog release required. The at least one aliphatic alcohol may be, for example, lauryl alcohol, myristyl alcohol or stearyl alcohol. In particularly preferred embodiments of the present oral dosage form, however, the at least one aliphatic alcohol is cetyl alcohol or cetostearyl alcohol. The amount of the at least one aliphatic alcohol in the present oral dosage form will be determined, as above, by the precise rate of tramadol or its analog release required. It will also depend on whether at least one polyalkylene glycol is present in or absent from the oral dosage form. In the absence of at least one polyalkylene glycol, the oral dosage form preferably contains between 20% and 50% by weight of the at least one aliphatic alcohol. When at least one polyalkylene glycol is present in the oral dosage form, then the combined weight of the at least one aliphatic alcohol and the at least one polyalkylene glycol preferably constitutes between 20% and 50% by weight of the total dosage.

The ratio of hydroxyalkyl cellulose or acrylic resin to the aliphatic alcohol/polyalkylene glycol determines, to a considerable extent, the release rate of the tramadol or its analog from the formulation. A ratio of the hydroxyalkyl cellulose to the aliphatic alcohol/polyalkylene glycol of between 1:2 and 1:4 is preferred, with a ratio of between 1:3 and 1:4 being particularly preferred.

The polyalkylene glycol may be, for example, polypropylene glycol or, which is preferred, polyethylene glycol. The number average molecular weight of the polyalkylene glycol is preferred between 1,000 and 15,000 especially between 1,500 and 12,000.

Another suitable controlled release matrix would comprise an alkylcellulose, especially ethyl cellulose, a $C_{12}$ to $C_{36}$ aliphatic alcohol and optionally a polyalkylene glycol.

The preferred matrix includes a pharmaceutically acceptable combination of at least two hydrophobic materials.

In addition to the above ingredients a controlled release matrix may also contain suitable quantities of other materials, for example diluents, lubricants, binders, granulating aids, colorants, flavorants and glidants that are conventionally used in the art of pharmaceutical formulation.

H. Processes for Preparing Matrix Based Beads

In order to facilitate the preparation of a solid, controlled release, oral dosage form according to this invention, any method of preparing a matrix formulation known to those skilled in the art may be used. For example incorporation in the matrix may be effected, for example, by (a) forming granules comprising at least one water soluble hydroxyalkyl cellulose and tramadol or its analog or a tramadol or its analog salt; (b) mixing the hydroxyalkyl cellulose containing granules with at least one $C_{12}$ to $C_{36}$ aliphatic alcohol; and (c) optionally, compressing and shaping the granules. Preferably, the granules are formed by wet granulating the hydroxyalkyl cellulose/tramadol or its analog with water. In a particularly preferred embodiment of this process, the amount of water added during tie wet granulation step is preferably between 1.5 and 5 times, especially between 1.75 and 3.5 times, the dry weight of the tramadol or its analog.

A spheronizing agent, together with the active ingredient can be spheronized to form spheroids. Microcrystalline cellulose is preferred. A suitable microcrystalline cellulose is, for example, the material sold as Avicel PH 101™ (FMC Corporation). In such embodiments, in addition to the active ingredient and spheronizing agent, the spheroids may also contain a binder. Suitable binders, such as low viscosity water soluble polymers, will be well known to those skilled in the pharmaceutical arts. However water soluble hydroxy lower alkyl cellulose, such as hydroxypropylcellulose are preferred. Additionally, or alternatively, the spheroids may contain a water insoluble polymer, especially an acrylic polymer, an acrylic copolymer, such as a methacrylic acid-ethyl acrylate copolymer, or ethyl cellulose. In such embodiments, the sustained release coating will generally include a hydrophobic material such as (a) a wax, either alone or in admixture with a fatty alcohol, or (b) shellac or zein.

I. Melt Extrusion Matrix

Sustained release matrices can also be prepared via melt-granulation or melt-extrusion techniques. Generally, melt-granulation techniques involve melting a normally solid hydrophobic material, such as a wax, and incorporating a powdered drug therein. To obtain a sustained release dosage form, it may be necessary to incorporate an additional hydrophobic substance, such as ethylcellulose or a water insoluble acrylic polymer, into the molten wax hydrophobic material. Examples of sustained release formulations prepared by melt granulation techniques as are found in U.S. Pat. No. 4,861,598, assigned to the Assignee of the present invention and hereby incorporated by reference in its entirety.

The additional hydrophobic material may comprise one or more water-insoluble wax like thermoplastic substances possibly mixed with one or more wax like thermoplastic substances being less hydrophobic than said one or more water insoluble wax like substances. In order to achieve constant release, the individual wax like substances in the formulation should be substantially non-degradable and insoluble in gastrointestinal fluids during the initial release phases. Useful water-insoluble wax like substances may be those with a water solubility that is lower than about 1:5,000 (w/w).

In addition to the above ingredients, a sustained release matrix may also contain suitable quantities of other materials, such as diluents, lubricants, binders, granulating aids, colorants, flavorants and glidants that are conventionally used in the pharmaceutical arts. The quantities of these additional materials will be sufficient to provide the desired effect to the desired formulation. In addition to the above ingredients, a sustained release matrix incorporating melt-extruded multiparticulates may also contain suitable quantities of other materials, such as diluents, lubricants, binders, granulating aids, colorants, flavorants and glidants that are conventional in the pharmaceutical art in amounts up to about 50% by weight of the particulate if desired.

Specific examples of pharmaceutically acceptable carriers and excipients that may be used to formulate oral dosage forms are described in the Handbook of Pharmaceutical Excipients, American Pharmaceutical Association (1986), incorporated by reference herein.

J. Melt Extrusion Multiparticulates

The preparation of a suitable melt-extruded matrix according to the present invention may, for example, include the steps of blending tramadol or its analog, together with at least one hydrophobic material and preferably the additional hydrophobic material to obtain a homogeneous mixture. The homogeneous mixture is then heated to a temperature sufficient to at least soften the mixture sufficiently to extrude the same. The resulting homogeneous mixture is then extruded to form strands. The extrudate is preferably cooled and cut into multiparticulates by any means known in the art. The strands are cooled and cut into multiparticulates. The multiparticulates are then divided into unit doses. The extrudate preferably has a diameter of from about 0.1 to about 5 mm and provides sustained release of the therapeutically active agent for a time period of from about 8 to about 24 hours.

An optional process for preparing the melt extrusions of the present invention includes directly metering into an extruder a hydrophobic material, a therapeutically active agent, and an optional binder, heating the homogenous mixture; extruding the homogenous mixture to thereby form strands; cooling the strands containing the homogeneous mixture, cutting the strands into particles having a size from about 0.1 mm to about 12 mm, and dividing said particles into unit doses. In this aspect of the invention, a relatively continuous manufacturing procedure is realized.

The diameter of the extruder aperture or exit port can also be adjusted to vary the thickness of the extruded strands. Furthermore, the exit part of the extruder need not be round; it can be oblong, rectangular, etc. The exiting strands can be reduced to particles using a hot wire cutter, guillotine, etc.

The melt extruded multiparticulate system can be, for example, in the form of granules, spheroids or pellets depending upon the extruder exit orifice. For purposes of the present invention, the terms "melt-extruded multiparticulate(s)" and "melt-extruded multiparticulate system(s)" and "melt-extruded particles" shall refer to a plurality of units, preferably within a range of similar size and/or shape and containing one or more active agents and one or more excipients, preferably including a hydrophobic material as described herein. In this regard, the melt-extruded multiparticulates will be of a range of from about 0.1 to about 12 mm in length and have a diameter of from about 0.1 to about 5 mm. In addition, it is to be understood that the melt-extruded multiparticulates can be any geometrical shape within this size range. Alternatively, the extrudate may simply be cut into desired lengths and divided into unit doses of the therapeutically active agent without the need of a spheronization step.

The oral dosage forms can be prepared to include an effective amount of melt-extruded multiparticulates within a capsule. For example, a plurality of the melt-extruded multiparticulates may be placed in a gelatin capsule in an amount sufficient to provide an effective sustained release dose when ingested and contacted by gastric fluid.

A suitable amount of the multiparticulate extrudate can be compressed into an oral tablet using conventional tableting equipment using standard techniques. Techniques and compositions for making tablets that are compressed and/or molded, capsules of hard and soft gelatin, and pills are also described in Remington's Pharmaceutical Sciences, (Arthur Osol, editor), 1553-1593 (1980), incorporated by reference herein.

The extrudate can be shaped into tablets as set forth in U.S. Pat. No. 4,957,681, (Klimesch, et al), described in additional detail above and hereby incorporated by reference.

Optionally, the sustained release melt-extruded multiparticulate systems or tablets can be coated, or the gelatin capsule can be further coated, with a sustained release coating such as the sustained release coatings described above. Such coatings preferably include a sufficient amount of hydrophobic material to obtain a weight gain level from about 2 to about 30 percent, although the overcoat may be greater depending upon the physical properties of the particular tramadol or its analog compound utilized and the desired release rate, among other things.

The melt extruded unit dosage forms of the present invention may further include combinations of melt extruded multiparticulates containing one or more of the therapeutically active agents disclosed above before being encapsulated. Furthermore, the unit dosage forms can also include an amount of an immediate release therapeutically active agent for prompt therapeutic effect. The immediate release therapeutically active agent may be incorporated as separate pellets within a gelatin capsule, or may be coated on the surface of the multiparticulates after preparation of the dosage forms such as within a controlled release coating or matrix base. The unit dosage forms of the present invention may also contain a combination of controlled release beads and matrix multiparticulates to achieve a desired effect.

The sustained release formulations of the present invention preferably slowly release the therapeutically active agent, such that when the dosage form is ingested and exposed to gastric fluids, and then to intestinal fluids a therapeutically desirable plasma level is obtained. The sustained release profile of the melt extruded formulations of the invention can be altered, for example, by varying the amount of retardant which may be a hydrophobic material, by varying the amount of plasticizer relative to hydrophobic material, by the inclusion of additional ingredients or excipients, or by altering the method of manufacture, etc.

The melt extruded material can be prepared without the inclusion of the therapeutically active agent, which is added thereafter to the extrudate. Such formulations typically will have the therapeutically active agent blended together with the extruded matrix material, and then the mixture would be tableted in order to provide a slow release formulation. Such formulations may be advantageous, for example, when the therapeutically active agent included in the formulation is sensitive to temperatures needed for softening the hydrophobic material and/or the retardant material.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Capsule Formulation Containing Gabapentin

The following ingredients in each one of the capsule formulations were weighed accurately, ground using a pestle and mortar to fine and homogeneous powders. These powders were sieved through 100 mesh and filled into hard gelatin capsules. The composition of each capsule formulation is listed below.

Capsule Formulation 1

|  | In each | In 100 |
| --- | --- | --- |
| Tramadol Hydrochloride | 39.8 mg | 3.98 g |
| Dextromethorphan Hydrochloride | 51.0 mg | 5.10 g |
| Gabapentin | 90.0 mg | 9.00 g |
| Microcrystalline Cellulose | 27.6 mg | 2.76 g |
| Sodium Lauryl Sulfate | 1.6 mg | 0.16 g |
| Total Solid | 210 mg | 21.0 g |

Capsule Formulation 2

|  | In each | In 100 |
| --- | --- | --- |
| Tramadol Hydrochloride | 39.8 mg | 3.98 g |
| Dextromethorphan Hydrochloride | 51.0 mg | 5.10 g |
| Gabapentin | 180.0 mg | 18.00 g |
| Microcrystalline Cellulose | 77.4 mg | 7.74 g |
| Sodium Lauryl Sulfate | 1.6 mg | 0.16 g |
| Total Solid | 350 mg | 35.0 g |

Capsule Formulation 3

|  | In each | In 100 |
| --- | --- | --- |
| Tramadol Hydrochloride | 35.0 mg | 3.50 g |
| Dextromethorphan Hydrochloride | 45.0 mg | 4.50 g |
| Gabapentin | 90.0 mg | 9.00 g |
| Microcrystalline Cellulose | 36.5 mg | 3.65 g |
| Sodium Lauryl Sulfate | 2.0 mg | 0.20 g |
| Talc | 1.5 mg | 0.15 g |
| Total Solid | 210 mg | 21.0 g |

Capsule Formulation 4

|  | In each | In 100 |
| --- | --- | --- |
| Tramadol Hydrochloride | 50.0 mg | 5.00 g |
| Dextromethorphan Hydrochloride | 30.0 mg | 3.00 g |
| Gabapentin | 180.0 mg | 18.00 g |
| Microcrystalline Cellulose | 86.5 mg | 8.65 g |
| Sodium Lauryl Sulfate | 2.0 mg | 0.20 g |
| Talc | 1.5 mg | 0.15 g |
| Total Solid | 350 mg | 35.0 g |

EXAMPLE 2

Capsule Formulation Containing Pregabalin

The following ingredients in each one of the capsule formulations were weighed accurately, ground using a pestle and mortar to fine and homogeneous powders. These powders were sieved through 100 mesh and filled into hard gelatin capsules. The composition of each capsule formulation is listed below.

Capsule Formulation 1

|  | In each | In 100 |
| --- | --- | --- |
| Tramadol Hydrochloride | 39.8 mg | 3.98 g |
| Dextromethorphan Hydrochloride | 51.0 mg | 5.10 g |
| Pregabalin | 15.0 mg | 1.50 g |

-continued

|  | In each | In 100 |
|---|---|---|
| Microcrystalline Cellulose | 102.6 mg | 10.26 g |
| Sodium Lauryl Sulfate | 1.6 mg | 0.16 g |
| Total Solid | 210 mg | 21.0 g |

Capsule Formulation 2

|  | In each | In 100 |
|---|---|---|
| Tramadol Hydrochloride | 39.8 mg | 3.98 g |
| Dextromethorphan Hydrochloride | 51.0 mg | 5.10 g |
| Pregabalin | 30.0 mg | 3.00 g |
| Microcrystalline Cellulose | 87.6 mg | 8.76 g |
| Sodium Lauryl Sulfate | 1.6 mg | 0.16 g |
| Total Solid | 210 mg | 21.0 g |

Capsule Formulation 3

|  | In each | In 100 |
|---|---|---|
| Tramadol Hydrochloride | 35.0 mg | 3.50 g |
| Dextromethorphan Hydrochloride | 45.0 mg | 4.50 g |
| Pregabalin | 20.0 mg | 2.00 g |
| Microcrystalline Cellulose | 106.5 mg | 10.65 g |
| Sodium Lauryl Sulfate | 2.0 mg | 0.20 g |
| Talc | 1.5 mg | 0.15 g |
| Total Solid | 210 mg | 21.0 g |

Capsule Formulation 4

|  | In each | In 100 |
|---|---|---|
| Tramadol Hydrochloride | 50.0 mg | 5.00 g |
| Dextromethorphan Hydrochloride | 30.0 mg | 3.00 g |
| Pregabalin | 40.0 mg | 4.00 g |
| Microcrystalline Cellulose | 86.5 mg | 8.65 g |
| Sodium Lauryl Sulfate | 2.0 mg | 0.20 g |
| Talc | 1.5 mg | 0.15 g |
| Total Solid | 210 mg | 21.0 g |

EXAMPLE 3

Capsule Formulation Containing Amitriptyline

The following ingredients in each one of the capsule formulations were weighed accurately, ground using a pestle and mortar to fine and homogeneous powders. These powders were sieved through 100 mesh and filled into hard gelatin capsules. The composition of each capsule formulation is listed below.

Capsule Formulation 1

|  | In each | In 100 |
|---|---|---|
| Tramadol Hydrochloride | 39.8 mg | 3.98 g |
| Dextromethorphan Hydrochloride | 51.0 mg | 5.10 g |

-continued

|  | In each | In 100 |
|---|---|---|
| Amitriptyline Hydrochloride | 11.4 mg | 11.40 g |
| Microcrystalline Cellulose | 106.2 mg | 106.2 g |
| Sodium Lauryl Sulfate | 1.6 mg | 0.16 g |
| Total Solid | 210 mg | 21.0 g |

Capsule Formulation 2

|  | In each | In 100 |
|---|---|---|
| Tramadol Hydrochloride | 39.8 mg | 3.98 g |
| Dextromethorphan Hydrochloride | 51.0 mg | 5.10 g |
| Amitriptyline Hydrochloride | 5.7 mg | 5.70 g |
| Microcrystalline Cellulose | 111.9 mg | 11.19 g |
| Sodium Lauryl Sulfate | 1.6 mg | 0.16 g |
| Total Solid | 210 mg | 21.0 g |

Capsule Formulation 3

|  | In each | In 100 |
|---|---|---|
| Tramadol Hydrochloride | 35.0 mg | 3.50 g |
| Dextromethorphan Hydrochloride | 45.0 mg | 4.50 g |
| Amitriptyline Hydrochloride | 11.4 mg | 1.14 g |
| Microcrystalline Cellulose | 115.1 mg | 11.51 g |
| Sodium Lauryl Sulfate | 2.0 mg | 0.20 g |
| Talc | 1.5 mg | 0.15 g |
| Total Solid | 210 mg | 21.0 g |

Capsule Formulation 4

|  | In each | In 100 |
|---|---|---|
| Tramadol Hydrochloride | 50.0 mg | 5.00 g |
| Dextromethorphan Hydrochloride | 30.0 mg | 3.00 g |
| Amitriptyline Hydrochloride | 11.4 mg | 1.14 g |
| Microcrystalline Cellulose | 115.1 mg | 11.51 g |
| Sodium Lauryl Sulfate | 2.0 mg | 0.20 g |
| Talc | 1.5 mg | 0.15 g |
| Total Solid | 210 mg | 21.0 g |

EXAMPLE 4

Capsule Formulation Containing Milnacipran

The following ingredients in each one of the capsule formulations were weighed accurately, ground using a pestle and mortar to fine and homogeneous powders. These powders were sieved through 100 mesh and filled into hard gelatin capsules. The composition of each capsule formulation is listed below.

Capsule Formulation 1

|  | In each | In 100 |
|---|---|---|
| Tramadol Hydrochloride | 39.8 mg | 3.98 g |
| Dextromethorphan Hydrochloride | 51.0 mg | 5.10 g |
| Milnacipran Hydrochloride | 11.4 mg | 11.40 g |

-continued

|  | In each | In 100 |
| --- | --- | --- |
| Microcrystalline Cellulose | 106.2 mg | 106.2 g |
| Sodium Lauryl Sulfate | 1.6 mg | 0.16 g |
| Total Solid | 210 mg | 21.0 g |

Capsule Formulation 2

|  | In each | In 100 |
| --- | --- | --- |
| Tramadol Hydrochloride | 39.8 mg | 3.98 g |
| Dextromethorphan Hydrochloride | 51.0 mg | 5.10 g |
| Milnacipran Hydrochloride | 5.7 mg | 5.70 g |
| Microcrystalline Cellulose | 111.9 mg | 11.19 g |
| Sodium Lauryl Sulfate | 1.6 mg | 0.16 g |
| Total Solid | 210 mg | 21.0 g |

Capsule Formulation 3

|  | In each | In 100 |
| --- | --- | --- |
| Tramadol Hydrochloride | 35.0 mg | 3.50 g |
| Dextromethorphan Hydrochloride | 45.0 mg | 4.50 g |
| Milnacipran Hydrochloride | 11.4 mg | 1.14 g |
| Microcrystalline Cellulose | 115.1 mg | 11.51 g |
| Sodium Lauryl Sulfate | 2.0 mg | 0.20 g |
| Talc | 1.5 mg | 0.15 g |
| Total Solid | 210 mg | 21.0 g |

Capsule Formulation 4

|  | In each | In 100 |
| --- | --- | --- |
| Tramadol Hydrochloride | 50.0 mg | 5.00 g |
| Dextromethorphan Hydrochloride | 30.0 mg | 3.00 g |
| Milnacipran Hydrochloride | 11.4 mg | 1.14 g |
| Microcrystalline Cellulose | 115.1 mg | 11.51 g |
| Sodium Lauryl Sulfate | 2.0 mg | 0.20 g |
| Talc | 1.5 mg | 0.15 g |
| Total Solid | 210 mg | 21.0 g |

EXAMPLE 5

Preparation of Capsaicin Palmitate (Formula I, $R=CH_3-(CH_2)_{14}$)

A mixture of 30.5 gm (~0.1M) of capsaicin USP27 (HUBEI XIANGXI CHEMICAL INDUSTRY CO., LTD, China), 16.7 ml (0.12M) of anhydrous triethylamine (Spectrum Chemicals), 220 mg of 4-(dimethylamino)pyridine and 200 ml of anhydrous dichloromethane was placed into a 1000 ml 2-neck round bottomed flask. The content was covered with aluminum foil to protect it from light exposure. The flask was fitted with a condenser fitted with a moisture trap on the top and a dropwise addition funnel. The flask was kept at room temperature and 25.4 ml (0.095M) of palmitoyl chloride was added from the funnel into the mixture slowly with stirring. After the addition, the mixture was refluxed for 3-6 hours and stirred for 10-15 hours at room temperature. The mixture was transferred into a separating funnel and washed successively with 2×500 ml of water, 2×500 ml of dilute hydrochloric acid, 2×500 ml of 10% sodium bicarbonate solution and 3×500 ml of type I water. The organic layer was separated, dried with anhydrous magnesium sulfate and the dichloromethane was removed under vacuum to produce a light yellow solid (95% of theoretical). The light yellow solid, as obtained above, was re-crystallized from ethanol. In a 2-liter flask, the solid was dissolved in 1 liter of hot ethanol and filtered through a filter paper. The filtrate was then cooled in the refrigerator to get white crystals.

EXAMPLE 6

Capsule Formulation Containing Gabapentin and Capsaicin Palmitate

The following ingredients in each one of the capsule formulations were weighed accurately, ground using a pestle and mortar to fine and homogeneous powders. These powders were sieved through 100 mesh and filled into hard gelatin capsules. The composition of each capsule formulation is listed below.

Capsule Formulation 1

|  | In each | In 100 |
| --- | --- | --- |
| Tramadol Hydrochloride | 39.8 mg | 3.98 g |
| Dextromethorphan Hydrochloride | 51.0 mg | 5.10 g |
| Gabapentin | 90.0 mg | 9.00 g |
| Capsaicin palmitate | 5.4 mg | 0.54 g |
| Microcrystalline Cellulose | 32.2 mg | 3.22 g |
| Sodium Lauryl Sulfate | 1.6 mg | 0.16 g |
| Total Solid | 220 mg | 22.0 g |

Capsule Formulation 2

|  | In each | In 100 |
| --- | --- | --- |
| Tramadol Hydrochloride | 39.8 mg | 3.98 g |
| Dextromethorphan Hydrochloride | 51.0 mg | 5.10 g |
| Gabapentin | 180.0 mg | 18.00 g |
| Capsaicin palmitate | 5.4 mg | 0.54 g |
| Microcrystalline Cellulose | 72.4 mg | 7.24 g |
| Sodium Lauryl Sulfate | 1.6 mg | 0.16 g |
| Total Solid | 350 mg | 35.0 g |

Capsule Formulation 3

|  | In each | In 100 |
| --- | --- | --- |
| Tramadol Hydrochloride | 35.0 mg | 3.50 g |
| Dextromethorphan Hydrochloride | 45.0 mg | 4.50 g |
| Gabapentin | 90.0 mg | 9.00 g |
| Capsaicin palmitate | 10.8 mg | 1.08 g |
| Microcrystalline Cellulose | 35.7 mg | 3.57 g |
| Sodium Lauryl Sulfate | 2.0 mg | 0.20 g |
| Talc | 1.5 mg | 0.15 g |
| Total Solid | 220 mg | 22.0 g |

Capsule Formulation 4

|  | In each | In 100 |
| --- | --- | --- |
| Tramadol Hydrochloride | 50.0 mg | 5.00 g |
| Dextromethorphan Hydrochloride | 30.0 mg | 3.00 g |
| Gabapentin | 180.0 mg | 18.00 g |
| Capsaicin palmitate | 5.4 mg | 0.54 g |

-continued

|  | In each | In 100 |
| --- | --- | --- |
| Microcrystalline Cellulose | 81.1 mg | 8.11 g |
| Sodium Lauryl Sulfate | 2.0 mg | 0.20 g |
| Talc | 1.5 mg | 0.15 g |
| Total Solid | 350 mg | 35.0 g |

EXAMPLE 7

Capsule Formulation Containing Gabapentin and Milnacipran

The following ingredients in each one of the capsule formulations were weighed accurately, ground using a pestle and mortar to fine and homogeneous powders. These powders were sieved through 100 mesh and filled into hard gelatin capsules. The composition of each capsule formulation is listed below.

Capsule Formulation 1

|  | In each | In 100 |
| --- | --- | --- |
| Tramadol Hydrochloride | 39.8 mg | 3.98 g |
| Dextromethorphan Hydrochloride | 51.0 mg | 5.10 g |
| Gabapentin | 45.0 mg | 9.00 g |
| Milnacipran Hydrochloride | 5.7 mg | 0.57 g |
| Microcrystalline Cellulose | 66.9 mg | 6.69 g |
| Sodium Lauryl Sulfate | 1.6 mg | 0.16 g |
| Total Solid | 210 mg | 21.0 g |

Capsule Formulation 2

|  | In each | In 100 |
| --- | --- | --- |
| Tramadol Hydrochloride | 39.8 mg | 3.98 g |
| Dextromethorphan Hydrochloride | 51.0 mg | 5.10 g |
| Gabapentin | 90.0 mg | 18.00 g |
| Milnacipran Hydrochloride | 5.7 mg | 0.57 g |
| Microcrystalline Cellulose | 31.9 mg | 3.19 g |
| Sodium Lauryl Sulfate | 1.6 mg | 0.16 g |
| Total Solid | 220 mg | 35.0 g |

Capsule Formulation 3

|  | In each | In 100 |
| --- | --- | --- |
| Tramadol Hydrochloride | 35.0 mg | 3.50 g |
| Dextromethorphan Hydrochloride | 45.0 mg | 4.50 g |
| Gabapentin | 90.0 mg | 9.00 g |
| Milnacipran Hydrochloride | 11.4 mg | 1.14 g |
| Microcrystalline Cellulose | 35.1 mg | 3.51 g |
| Sodium Lauryl Sulfate | 2.0 mg | 0.20 g |
| Talc | 1.5 mg | 0.15 g |
| Total Solid | 220 mg | 22.0 g |

Capsule Formulation 4

|  | In each | In 100 |
| --- | --- | --- |
| Tramadol Hydrochloride | 50.0 mg | 5.00 g |
| Dextromethorphan Hydrochloride | 30.0 mg | 3.00 g |
| Gabapentin | 180.0 mg | 18.00 g |

-continued

|  | In each | In 100 |
| --- | --- | --- |
| Milnacipran Hydrochloride | 5.7 mg | 0.57 g |
| Microcrystalline Cellulose | 80.8 mg | 8.08 g |
| Sodium Lauryl Sulfate | 2.0 mg | 0.20 g |
| Talc | 1.5 mg | 0.15 g |
| Total Solid | 350 mg | 35.0 g |

EXAMPLE 8

Capsule Formulation Containing Gabapentin and Amitriptyline

The following ingredients in each one of the capsule formulations were weighed accurately, ground using a pestle and mortar to fine and homogeneous powders. These powders were sieved through 100 mesh and filled into hard gelatin capsules. The composition of each capsule formulation is listed below.

Capsule Formulation 1

|  | In each | In 100 |
| --- | --- | --- |
| Tramadol Hydrochloride | 39.8 mg | 3.98 g |
| Dextromethorphan Hydrochloride | 51.0 mg | 5.10 g |
| Gabapentin | 45.0 mg | 9.00 g |
| Amitriptyline Hydrochloride | 5.7 mg | 0.57 g |
| Microcrystalline Cellulose | 66.9 mg | 6.69 g |
| Sodium Lauryl Sulfate | 1.6 mg | 0.16 g |
| Total Solid | 210 mg | 21.0 g |

Capsule Formulation 2

|  | In each | In 100 |
| --- | --- | --- |
| Tramadol Hydrochloride | 39.8 mg | 3.98 g |
| Dextromethorphan Hydrochloride | 51.0 mg | 5.10 g |
| Gabapentin | 90.0 mg | 18.00 g |
| Amitriptyline Hydrochloride | 5.7 mg | 0.57 g |
| Microcrystalline Cellulose | 31.9 mg | 3.19 g |
| Sodium Lauryl Sulfate | 1.6 mg | 0.16 g |
| Total Solid | 220 mg | 35.0 g |

Capsule Formulation 3

|  | In each | In 100 |
| --- | --- | --- |
| Tramadol Hydrochloride | 28.5 mg | 2.85 g |
| Dextromethorphan Hydrochloride | 34.0 mg | 3.40 g |
| Gabapentin | 30.0 mg | 3.00 g |
| Amitriptyline Hydrochloride | 5.7 mg | 0.57 g |
| Microcrystalline Cellulose | 118.3 mg | 11.83 g |
| Sodium Lauryl Sulfate | 2.0 mg | 0.20 g |
| Talc | 1.5 mg | 0.15 g |
| Total Solid | 220 mg | 22.0 g |

EXAMPLE 9

Capsule Formulation Containing Gabapentin, Amitriptyline and Capsaicin Palmitate The following ingredients in each one of the capsule formulations were weighed accurately, ground using a pestle and mortar to fine and homogeneous powders. These powders were sieved through 100 mesh and filled into hard gelatin capsules. The composition of each capsule formulation is listed below.

Capsule Formulation 1

|  | In each | In 100 |
| --- | --- | --- |
| Tramadol Hydrochloride | 39.8 mg | 3.98 g |
| Dextromethorphan Hydrochloride | 51.0 mg | 5.10 g |
| Gabapentin | 30.0 mg | 3.00 g |
| Amitriptyline Hydrochloride | 5.7 mg | 0.57 g |
| Capsaicin palmitate | 5.4 mg | 0.54 g |
| Microcrystalline Cellulose | 86.5 mg | 8.65 g |
| Sodium Lauryl Sulfate | 1.6 mg | 0.16 g |
| Total Solid | 220 mg | 22.0 g |

Capsule Formulation 2

|  | In each | In 100 |
| --- | --- | --- |
| Tramadol Hydrochloride | 28.5 mg | 2.85 g |
| Dextromethorphan Hydrochloride | 34.0 mg | 3.40 g |
| Gabapentin | 30.0 mg | 3.00 g |
| Amitriptyline Hydrochloride | 5.7 mg | 0.57 g |
| Capsaicin palmitate | 5.4 mg | 0.54 g |
| Microcrystalline Cellulose | 114.8 mg | 11.48 g |
| Sodium Lauryl Sulfate | 1.6 mg | 0.16 g |
| Total Solid | 350 mg | 35.0 g |

EXAMPLE 10

Efficacy of the Combination Therapy in Humans

Patient 1: Condition: Diabetic Neuropathy

A 50 year old white male was diagnosed with diabetic neuropathy and he was given capsules of formulation 1 in Example 1. He has provided the following testimony after using the capsules. "I have great pain due to diabetic neuropathy in my legs and feet. I became naturopathic after a long series of intravenous antibiotics. In an effort to ease the pain I have overdosed on aspirin, taken prescribed antidepressants, and even heavy narcotics. All these medicines would only curb the pain enabling me to get a couple hours of sleep a night. Since taking the capsules I have experienced a complete removal of the pain. It only takes 30 minutes to work and last up to 18 hours. I also have experienced complete sound and restful sleep."

Patient 2: Condition: Arthritis

A 64 year old female has joint pain and stiffness associated with osteoarthritis. She was given capsules of formulation 1 in Example 1. She wrote the following testimony after taking the capsules. "Normally morning is my worst time of the day. Having to stretch and warm up my body to get moving. This process can last for 30 minutes or more. By taking the capsule, problem solved. I sleep through the entire night and can start my mornings with ease. My quality of life, with the other pain medication, was maybe, on a scale of 1 to 10, a 3. The capsule enables me to enjoy life on a 9-10 level. Before taking capsule my morning was a chore to get moving and then spent the rest of the day trying to ease the pain of my arthritis and muscle discontent."

Patient 3: Condition: Double Nephrectomy

A white female of 44 years old had undergone double nephrectomy and has chronic back pain and stiffness. She has provided the following testimony after taking the capsules of formulation 1 in Example 1. "I am a 44 year old female with no kidneys. I have to be careful of anything I take regarding medication. Finally there is something that takes away all of the pain. I suffer from back pain and stiffness. Using the capsule for several days, I am very impressed with the level of relief it brings. I takes less than 20 minutes for it to take effect and allows me to move around like nothing is wrong. This is very exciting to know there will be something on the market that really works. I have also noticed that pain relief is the only effect of this product-no nausea or dizziness."

Patient 4: Condition: Fibromyalgia

A 44 year old Hispanic female has developed fibromyalgia syndrome and constant pain in her body due to the syndrome. She was provided the capsules of formulation 1 in Example 1. She provided the following testimony after taking the capsules. "I am a non diabetic person who suffers from Fibromyalgia. This condition came about 3 years ago. Not wanting to take heavy narcotics I settled on a prescription of Tramadol. This drug only gave me moderate relief and I am in constant pain. The area of affliction is the left torso arm and leg. The pain is so intense I am like a bent and folded statue. On scale of 1-10 in pain, I am an 11. I have thoughts of suicide often to end the pain. There is no quality of life.

After the taking the capsule, in just 11 minutes the burning pain in my arm was gone. In 5 more minutes I had full range of motion and renewed strength in my body. No other compound on the market could have helped. I know because I am retired nurse. I received 100% relief with this product and now believe I can live again. The capsule lasted 21 hours before I need to take another".

An observer of the event described as follows. "I saw something remarkable. My name is Brenda and I deal with the general public every day. A customer came in to get a soda and her name is Sylvia. I had not seen her in quite some time. She had been a regular customer since 5 years ago. The last 2 years she was in so much pain that her body was contorted and her personality diminished. Her quality of life was gone and she even spoke of suicide to end it all. I felt so sorry for her because of the wonderful person that she was. Sylvia just happened to come in this day as Joe was coming by for another reason. I introduced the two and he gave her a product. She took it at 1:05 and I kept my eye on her. At 1:16 her burning sensations were gone and her shoulders were straightened up. She put her hand on her upper right arm, looked at me with a grin and said the tingling pain is gone. She was glowing and no longer hunched over. She was sitting erect and even lifted her arms over her head which could not be done 15 minutes earlier. It was truly amazing! She was smiling like I haven't seen in a long time. She began turning her head side to side and got her personality and her life back."

Patient 5: Condition: Cancer Neuropathy

A 61 year male who has bone cancer and pain has been given the capsules of formulation 1 in Example 1. He has provided the following testimony. "I have bone cancer in my left shoulder. After all the treatments to control the spread of the disease I have been in intense pain. I could not sleep more than 2 to 3 hours and would cramp up the rest of the time. After taking the TLI-1026 I was amazed to have to be awakened after 9 hours of restful sleep. No cramps along with total relief of the pain from the neuropathy from the chemo and radiation therapies."

Patient 6: Condition: Abscessed Tooth

A 46 year old male has constant tooth ache and he was provided with the capsule of formulation 1 in Example 1. He wrote the following testimony. "I have been taking Loratab 5 for a consistent tooth ache. I have to wait for an abscess in my mouth to heal before a dentist can fix the problem. While waiting I tried a new medication called TLI-1026. In about 30 minutes I was 80% of the pain was gone. Hours later the pain was all gone. The pain was located at the bottom right hand lower jaw and was abscessed as well."

Patient 7: Condition: Acute Lumbar Pain

A 23 year old male has acute pain in the back and he was provided with the capsules of formulation 1 in Example 1. He has provided the following testimony. "I have dealt with acute pain in my lumbar region for over 2 years now as a result of an injury sustained while lifting heavy loads improperly. Initially, the pain was bearable as I told myself it would go away. After awhile though, I would find myself having to lie down 2-3 times a day to take vertical pressure off my lower back due to intense flares in the pain. After about 2 months of daily, excruciating back pain I went to see my physician because I was losing sleep. I was prescribed Soma (Carisoprodol), 350 mg, twice daily. This only seemed to mask the pain, and would make me quite drowsy during the day—which eventually led to me not finishing my prescription. I then was prescribed Vicodin (Hydrocodone), in 5 mg doses (coupled with the 500 mg of Acetaminophen), this also caused me to become quite drowsy and as with the Soma only masked the pain for a couple hours—though if I contorted my body to exacerbate the pain, it was still present. After trying one of the TLI-1026 formulation though, my pain was relieved. In less than a half hour my pain was not only unnoticeable, it couldn't be summoned by twisting my lower back. The effects were mild to none, with no drowsiness. The pain was relieved for 18 hrs and allowed me to sleep like a child—not moving for hours, and waking up completely rested with the residual effects of this formulation still helping. This formulation allows me to continue throughout my daily routine without having to worry about back pain, without having to take a pill every 3 hours and without spending hours trying to get comfortable in bed. I'm sure my liver appreciates the lack of Acetaminophen also."

Patient 8: Condition: Fibromyalgia

A 23 year old female was diagnosed with fibromyalgia due to lyme disease. She was given the capsules of formulation 1 in Example 1. She has provided the following testimony. "I was diagnosed with fibromyalgia a year ago by a rheumatologist and based on blood work done in a laboratory, fibromyalgia was due to lime disease I contacted sometime ago. I have constant neuropathic pain, headache and fatigue all the time. Being young, I like to be very active in daily activities. I took one capsule and within 50 minutes my headache and hip joint pain was almost gone. After 12 hours, I took the second capsule and I had complete relief from pain, headache and fatigue. I was amazed by the results and my doctor could not believe my improvement".

Patient 9: Condition: Cervical Spondyolosis

A female was diagnosed with cervical spondyolosis. She was given the capsules of formulation 1 in Example 1. She has provided the following testimony. "The pain medication I have been trying has been working well. It seemed to take 3-4 days to work completely. I began taking it on Aug. 25, 2007. During the 1$^{st}$ day of use I experienced a sort of light headedness—a floating feeling but it did not seem to interfere with my daily activities. I am still taking the medicine every 12 hours (approximately)—I take 1 in the morning and 1 at night. Prior to this medication, I was taking Vicoprofin for pain associated with cervical spondyolosis.— diagnosed at age 35. The Vicoprofin was not really helping with my pain anymore. Also, I get what I call "weather headaches"—I think also associated with hormonal changes. Nothing helped these headaches!! I had one of these headache when I began this medication—now no headaches! Thank you for this opportunity to be free of pain!!"

Patient 10: Condition: Fibromyalgia

A female patient diagnosed with fibromyalgia was provided with the capsules of formulation 1 in example 1. She gave the following testimony. "My name is DeAnn Thomas, age 69. I have been treated for "Fibromyalgia" for 8-10 years by Dr. Mike Tyler. For the past 4 or 5 years I have been on Norco 10/325; 6 per day. It has worked for me, but not totally, taking only the edge off of the pain.

On Jul. 30 of this year 2007, I had total knee replacement on my left knee. After leaving the hospital I was given the maximum dosage (2 every 6 hrs). My pain was so bad I cried for the next 2 weeks. I thought I would go crazy because the pain was so intense. Finally I went to my PCP. He prescribed "Duragesic patches. This greatly helped my knee's but my fibromyalgis kept getting worse. So much so that I started taking my "Norco" 2 pills three times a day.

I went back to Dr. Tyler for my pain management to discuss the experimental drug (TLI-1026) in the beginning of September. Within a few days I started the experimental drug and I have been on it since. He also has me on "Norco" 1 in the morning and 1 at night.

I feel like a new person, full of energy and virtually no pain and I am emotionally better than 1 have been in years.

I thank God everyday for this new experimental drug and thank Dr. Tyler as well".

EXAMPLE 11

Synergistic Effect of the Combination Therapy in Humans

1. Patients with Diabetic Neuropathy and Fibromyalgia

In order to assess the effectiveness of the present inventive composition, two sets of capsules were provided to patients with diabetic neuropathy and fibromyalgia. One set of capsules called TLI-1180 contained 35 mg of tramadol and 45 mg of dextromethorphan and the other set of capsules called TLI-1026 contained the composition of formulation 1 in example 1. The following testimony was provided by the physician who monitored the patients.

"I would like to briefly provide a testimonial, from a clinical perspective, regarding the distinct differentiation between TLI-1180 in comparison to TLI-1026. I have utilized these two experimental medicine compounds on individuals with known diabetes mellitus with peripheral neuropathy as well confirmed fibromyalgia utilizing the American College of Rheumatology trigger point scoring system. These patients had tried up to 1600 mg per day of gabapentin with partial and marginal relief from their pain. Here are my observations.

With regards to the two individuals with diabetes mellitus who tried TLI-1180, each experienced a substantial reduction in neuropathic symptomatology, namely a decrease but not near total resolution in the burning and tingling sensation in the lower extremities. There remained a dull aching pain with increased discomfort at the end of the day. In sharp contrast TLI-1026 completely eliminated the burning and tingling sensation to the point where the symptoms were not noticeable. Additionally, the dull aching pain was suppressed and did not increase at the end of the day.

The two individuals with confirmed fibromyalgia were also given both respective medications. Again, a very stark contrast is evident in clinical efficacy, and in this case, the side effects profile as well. TLI-1180 certainly decreased the pain and arthropathy associated with fibromyalgia, as well as increased joint range of motion with decreased stiffness. Furthermore, both individuals experienced mild gastrointestinal upset, namely nausea and one case of vomiting. With TLI-1026, again, there was near complete resolution of pain, arthropahy, and excellent increase in joint range of motion without stiffness. The resolution was markedly more significant with TLI-1026 in comparison to TLI-1180. More importantly, the side effect profile was absent of any noteworthy events for TLI-1026".

2. Patient with Diabetic Neuropathy

A 50 year old white male was diagnosed with diabetic neuropathy and he was given capsules of formulation 1 in Example 1 (TLI-1026) and capsules containing 35 mg of tramadol and 45 mg of dextromethorphan (TLI-1180). He has provided the following testimony after using the capsules. "I have great pain due to diabetic neuropathy in my legs and feet. I became neuropathic after a long series of intravenous antibiotics. In an effort to ease the pain I have overdosed on aspirin, taken prescribed antidepressants, 1600-2000 mg of Nurontin and even heavy narcotics. All these medicines would only curb the pain enabling me to get a couple hours of sleep a night.

Since taking the capsules TLI-1026, I have experienced a complete removal of the pain and there is no tingling sensation in my feet. It only takes 30 minutes to work and last up to 18 hours. I also have experienced complete sound and restful sleep. Based on the advice, I tried another capsule called TLI-1180 and this capsule was able to reduce my pain up to 70-80% and last for 5-6 hours. The tingling sensation in my feet was there and I have to take 3-4 capsules per day for good sleep".

EXAMPLE 12

The Effect of the Combination Therapy Containing Amitriptyline in Humans

1. Patient with Diabetic Neuropathy

A 50 year old white male was diagnosed with diabetic neuropathy and he was given capsules of formulation 1 in Example 3 (TLI-8611) and he gave the following testimony. "I have great pain due to diabetic neuropathy in my legs and feet. I became neuropathic after a long series of intravenous antibiotics. In an effort to ease the pain I have overdosed on aspirin, taken prescribed antidepressants, 1600-2000 mg of Nurontin and even heavy narcotics. All these medicines would only curb the pain enabling me to get a couple hours of sleep a night.

I experimented TLI-1026 which contains gabapentin and since taking the capsules TLI-8611, I have experienced a complete removal of the pain and there is no tingling sensation in my feet. It only takes 30 minutes to work and last up to 18 hours and sometimes almost 24 hours. For me, both TLI-8611 and TLI-1026 work completely and I could not tell the difference as I have complete relief from pain and can sleep well during the night".

2. Patient with Diabetic Neuropathy

Two patients diagnosed with diabetic neuropathy were given capsules of formulation 1 in Example 3 (TLI-8611). The physician who was monitoring the patients gave the following testimony. "I would like to briefly provide a confidential testimonial, from a clinical perspective, to discuss the efficacy of TLI 8611 for two patients with know diabetic peripheral polyneuropathy. Here are my observations.

With regards to the two individuals with diabetes mellitus who tried TLI 8611, each experienced a substantial reduction in neuropathic symptomatology, and near total resolution in the burning and tingling sensation in the lower extremities to the point where symptoms were not noticeable and there was no affect of the neuropathy on the individual's quality of life or activities of daily living. Essentially, even the dull aching pain that is typically present with neuropathy, was resolved with TLI 8611. Additionally, the two individuals who took TLI 8611 previously had attempted neuropathic pain reduction with Neurotin, Elavil, and finally Lyrica, all well-known as drugs used to treat neuropathic symptoms. The Neurontin and Elavil provided no substantial pain relief. Lyrica provided only minimal resolution of symptoms. Each carried its own substantial, negative side effects, particularly the Neurontin and Elavil. In sharp contrast, TLI 8611 was tolerated very well when taken with food, with minimal neurologic, gastrointestinal, or other side effects noted.

In conclusion, TLI 8611 appears to be an efficacious product which functions to alleviate and treat diabetic peripheral neuropathy in a safe, novel manner. Do not hesitate to contact me with further questions".

EXAMPLE 13

The Effect of the Combination Therapy Containing Amitriptyline and Gabapentin in Humans Patient with Diabetic Neuropathy A white male was diagnosed with diabetic neuropathy and he was given capsules of formulation 1 in Example 8 (TLI-1126) and he gave the following testomony "I use regularly TLI-1026 which contains gabapentin for my diabetic neuropathy pain. I was curious to know the effect of TLI-1126 which I was told to contain both gabapentin and amitriptyline. I took one capsule and within 1 hour I have experienced a complete removal of the pain and there is no tingling sensation in my feet. The relief was so complete and the effect was so intense, I slept almost 12 hours. For me, TLI-1126 is too much and I thought I could manage with half the dose of TLI-1126 for my pain".

EXAMPLE 14

The Effect of the Combination Therapy Containing Gabapentin and Capsaicin Palmitate in Humans The composition described in formulation 1 in example 6 was given to two patients who have been diagnosed with diabetic neuropathy pain. The patients took 2 capsules per day at 12 hours interval and both felt complete relief from pain associated with neuropathy.

EXAMPLE 15

The Effect of the Combination Therapy Containing Amitriptyline and Capsaicin Palmitate in Humans The composition described in formulation 1 in example 9 was given to two patients who have been diagnosed with diabetic neuropathy pain. The patients took 2 capsules per day at 12 hours interval and both felt complete relief from pain associated with neuropathy.

REFERENCES

The following references, to the extent that they provide exemplary procedural or other details supplementary to those set forth herein, are specifically incorporated herein by reference.

Plesan A, Hedman U, Xu X J, Wiesenfeld-Hallin Z. Comparison of ketamine and dextromethorphan in potentiating the antinociceptive effect of morphine in rats. Anesth Analg 1998; 86: 825-9.

Klepstad P, Maurset A, Moberg E R, Oye I. Evidence of a role for NMDA receptors in pain perception. Eur J Pharmacol 1990; 187: 513-8.

Eisenberg E, Pud D. Can patients with chronic neuropathic pain be cured by acute administration of the NMDA receptor antagonist amantadine? Pain 1998; 74: 337-9.

Kinnman E, Nygards E B, Hansson P. Effects of dextromethorphan in clinical doses on capsaicin-induced ongoing pain and mechanical hypersensitivity. J Pain Symptom Manage 1997; 14: 195-201.

Kawamata T, Omote K, Kawamata M, Namiki A. Premedication with oral dextromethorphan reduces postoperative pain after tonsillectomy. Anesth Analg 1998; 86: 594-7.

Woolf C J, Chong M S. Preemptive analgesia—treating postoperative pain by preventing the establishment of central sensitization. Anesth Analg 1993; 77: 362-79.

Bern J L, Peck R. Dextromethorphan. An overview of safety issues. Drug Saf 1992; 7: 190-9.

Battaglia G, Rustioni A. Coexistence of glutamate and substance P in dorsal root ganglion neurons of the rat and monkey. J Comp Neurol 1988; 277: 302-12.

Aanonsen L M, Wilcox G L. Nociceptive action of excitatory amino acids in the mouse: effects of spinally administered opiates, phencyclidine and sigma agonists. J Pharmacol Exp Ther 1987; 243: 9-19.

Davies S N, Lodge D. Evidence for involvement of Nmethyl-D-aspartate receptors in 'wind-up' of class 2 neurones in the dorsal horn of the rat. Brain Res 1987; 424: 402-6.

Dickenson A H. Spinal cord pharmacology of pain. Br J Anaesth 1995; 75: 193-200.

Felsby S, Nielsen J, Arendt-Nielsen L, Jensen T S. NMDA receptor blockade in chronic neuropathic pain: a comparison of ketamine and magnesium chloride. Pain 1995; 64: 283-91.

Dickenson A H. A cure for wind up: NMDA receptor antagonists as potential analgesics. Trends Pharmacol Sci 1990; 11: 307-9.

Dickenson A H, Sullivan A F. Differential effects of excitatory amino acid antagonists on dorsal horn nociceptive neurones in the rat. Brain Res 1990; 506: 31-9.

Ilkjaer S, Petersen K L, Brennum J, Wernberg M, Dahl J B. Effect of systemic N-methyl-D-aspartate receptor antagonist (ketamine) on primary and secondary hyperalgesia in humans. Br J Anaesth 1996; 76: 829-34.

Albers G W, Atkinson R P, Kelley R E, Rosenbaum D M. Safety, tolerability, and pharmacokinetics of the Nmethyl-D-aspartate antagonist dextrorphan in patients with acute stroke. Stroke 1995; 26: 254-8.

Muir K W, Lees K R. Clinical experience with excitatory amino acid antagonist drugs. Stroke 1995; 26: 503-13.

Roytblat L, Korotkoruchko A, Katz J, Glazer M, Greemberg L, Fisher A. Postoperative pain: the effect of low-dose ketamine in addition to general anesthesia. Anesth Analg 1993; 77: 1161-5.

Mercadante S. Ketamine in cancer pain: an update. Palliat Med 1996; 10: 225-30.

Kornhuber J, Quack G, Danysz W, et al, Therapeutic brain concentration of the NMDA receptor antagonist amantadine. Neuropharmacology 1995; 34: 713-21.

Grotta J, Clark W, Coull B, et a/Safety and tolerability of the glutamate antagonists CGS 19755 (Selfotel) in patients with acute ischemic stroke. Results of a phase IIa randomized trial. Stroke 1995; 26: 602-5.

Benson W M, Stefko P L, Randall L O. Comparative pharmacology of levorphanol, racemorphan and dextrorphan and related methyl ethers. J Pharmacol Exp Then 953; 109: 189-200.

Karlsson M O, Dahlström N A, Neil A. Characterization of high-affinity binding sites for the antitussive [3H] noscapine in guinea pig brain tissue. Eur J Pharmacol 1988; 145: 195-203.

Albers G W, Sáenz R E, Moses J A Jr, Choi D W. Safety and tolerance of oral dextromethorphan in patients at risk from brain ischemia. Stroke 1991; 22: 1075-7.

Bonuccelli U, Del Dotto P, Piccini P, Behge F, Corsini G U, Muratorio A. Dextromethorphan and parkinsonism (Letter). Lancet 1992; 340: 53.

Fisher R S, Cysyk B J, Lesser R P, et al, Dextromethorphan for treatment of complex partial seizures. Neurology 1990; 40: 547-9.

Ziemann U, Chen R, Cohen L G, Hallett M. Dextromethorphan decreases the excitability of the human motor cortex. Neurology 1998; 51: 1320-4.

Mendell L M. Physiological properties of unmyelinated fiber projection to the spinal cord. Exp Neurol 1966; 16: 316-32.

Church J, Lodge D, Berry S C. Differential effects of dextrorphan and levorphanol on the excitation of rat spinal neurons by amino acids. Eur J Pharmacol 1985; 111: 185-90.

Musacchio J M, Klein M. Dextromethorphan binding sites in the guinea pig brain. Cell Mol Neurobiol 1988; 8: 149-56.

Church J, Shacklock J A, Baimbridge K G. Dextromethorphan and phencyclidine receptor ligands: differential effects on K+ and NMDA-evoked increases in cytosolic free Ca2+ concentration. Neurosci Lett 1991; 124: 232-4.

Ferkany J W, Borosky S A, Clissold D B, Pontecorvo M J. Dextromethorphan inhibits NMDA-induced convulsions. Eur J Pharmacol 1988; 151: 151-4.

Choi D W. Dextrorphan and dextromethorphan attenuate glutamate neurotoxicity. Brain Res 1987; 403: 333-6.

Verhagen Metman L, Del Dotto P, Natté R, Van den Munchof P, Chase T N. Dextromethorphan improves levodopa-induced dyskinesias in Parkinson's disease. Neurology 1998; 51: 203-6.

Woodworth J R, Denis S R K, Moore L, Rotenberg K S. The polymorphic metabolism of dextromethorphan J Clin Pharmacol 1987; 27: 139-43.

Musacchio J M, Klein M, Canoll P D. Dextromethorphan and sigma ligands: common sites but diverse effects. Life Sci 1989; 45: 1721-32.

Kiss I E, Killian M. Does opiate premedication influence postoperative analgesia? A prospective study. Pain 1992; 48: 157-8.

Tverskoy M, Oz Y, Isakson A, Finger J, Bradley E L Jr, Kissin I. Preemptive effect of fentanyl and ketamine on postoperative pain and wound hyperalgesia. Anesth Analg 1994; 78: 205-9.

Henderson D J, Withington B S, Wilson J A, Morrison L M M. Perioperative dextromethorphan reduces postoperative pain after hysterectomy. Anesth Analg 1999; 89: 399-402.

Ilkjaer S, Dirks J, Brennum M, Wernberg M, Dahl J B. Effect of systemic N-methyl-D-aspartate receptor antagonist (dextromethorphan) on primary and secondary hyperalgesia in humans. Br J Anaesth 1997; 79: 600-5.

Price D D, Mao J, Frenk H, Mayer D J. The N-methyl-D-aspartate receptor antagonist dextromethorphan selectivity reduces temporal summation of second pain in man. Pain 1994; 59: 165-74.

Chia Y Y, Liu K, Chow L H, Lee T Y. The operative administration of intravenous dextromethorphan reduces postoperative morphine consumption. Anesth Analg 1999; 89: 748-52.

Yamamoto T, Yaksh T L. Comparison of the antinociceptive effects of pre- and posttreatment with intrathecal morphine and MK-801, a NMDA antagonist, on formalin test in rat. Anesthesiology 1992; 77: 757-63.

Dayer P, Desmeules J, Collart L. Pharmacology of tramadol Drugs 1997; 53 Suppl 2:18-24.

Raffa R B A novel approach to the pharmacology of analgesics. Am J Med 1996; 101(1A):40S-46S.

Reimann W, Hennies H H. Inhibition of spinal noradrenaline uptake in rats by the centrally acting analgesic tramadol. Biochem Pharmacol 1994; 47(12):2289-93.

Dayer P, Collart L, Desmeules J. The pharmacology of tramadol. Drugs 1994; 47 Suppl 1:3-7.

Raffa R B, Friderichs E, Reimann W, Shank R P, Codd E E, Vaught J L, Jacoby H I, Selve N. Complementary and synergistic antinociceptive interaction between the enantiomers of tramadol J Pharmacol Exp Ther 1993; 267: 331-40.

Lee C R, McTavish D, Sorkin E M. Tramadol. A preliminary review of its pharmacodynamic and pharmacokinetic properties, and therapeutic potential in acute and chronic pain states. Drugs 1993; 46(2):313-40.

Tobias J D. Seizure after overdose of tramadol. South Med J 1997; 90(8):826-7.

Weinbroum A A, Valery R, Gideon P, Ben-Abraham R. The role of dextromethorphan in pain control CAN J ANESTH 2000; 47: 585-596.

Rodd E H. Chemistry of Carbon Compounds, Elsevier Publ, New York, 1960.

Choi D W. "Dextrorphan and dextromethorphan attenuate glutamate neurotoxicity," Brain Res 1987; 402: 333-336.

Won, B Y et al, Dextrorphan and dextromethorphan, common antitussives, are antiepileptic and antagonize NMDA in brain slices, Neurosci Letters 1988; 85: 21-26.

Steinberg G K et al, Delayed treatment with dextromethorphan and dextrorphan reduces cerebral damage after transient focal ischemia, Neurosci Letters 1988; 89: 193-197.

Tortella et al, TIPS 1989; 10: 501-507.

Prince & Feeser. Neurosci Letters 1988; 85: 291-296.

Carpenter C L et al, Dextromethorphan and dextrorphan as calcium channel antagonists, Brain Research 1988; 439: 372-375.

Craviso G L and Musacchio J M. High affinity dextromethorphan binding sites in guinea pig brain, Mol Pharmacol 1983; 23: 619-640.

Feeser et al, Neurosci Letters 1988; 86: 340-345.

Ferkany et al, Eur J Pharmacol 1988; 151: 151-154.

Koyuncuoglu and Saydam. Intnl J Clin Pharmacol Ther Tox 1990; 28: 147-152.

Musacchio J M et al, High affinity dextromethorphan binding sites in the guinea pig brain, J Pharmacol Exp Ther 1988; 247: 424-431.

Vettican S J et al, Phenotypic differences in dextromethorphan metabolism, Pharmaceut Res 1989; 6: 13-19.

Ramachander G et al, Determination of dextrorphan in plasma and evaluation of bioavialability dextromethorphan hydrobromide in humans, J Pharm Sci 1977; 66: 1047-1048.

Leander. Epilepsy Res 1989; 4: 28-33.

Inaba T et al, In vitro inhibition studies of two isozymes of human liver cytochrome P-450, Drug Metabolism and Disposition 1985; 13: 443-447.

Inaba T et al, Quinidine: Potent inhibition of sparteine and debrisoquin oxidation in vivo, Br Clin Pharmacol 1986; 22: 199-200.

Koppel C et al, Urinary metabolism of dextromethorphan in man, Arzneim. Forsch./Drug Research 1987; 37: 1304-1306.

Brosen K et al, Extensive metabolizers of debrisoquin become poor metabolizers during quinidine treatment, Pharmacol Toxicol 1987; 60: 312-314.

Testa B and Jenner P. Inhibitors Of Cytochrome P-450s and Their Mechanism of Action, DRUG METABOLISM REVIEWS 1981; 12: 1-117.

Guengerich F P. Cytochrome P450: Advances and Prospects, FASEB J 1992; 6: 667-668.

Brosen K, Murray M and Reidy C F. Recent Developments In Hepatic Drug Oxidation Implications For Clinical Pharmacokinetics, CLIN PHARMACOKINET 1990; 18: 220-239.

Murray M and Reidy G F. Selectivity in the Inhibition of Mammalian Cytochrome P-450 By Chemical Agents, PHARMACOLOGICAL REVIEWS 1990; 42: 85-101.

Porter T D and Coon M J. Cytochrome P-450: Multiplicity of Isoforms, Substrates, and Catalytic and Regulatory Mechanisms, J BIOL CHEM 1991; 266: 13469-13472.

Guengerich F P. Characterization of Human Microsomal Cytochrome P-450 Enzymes, ANNU REV PHARMACOL TOXICOL 1989; 29: 241-264 (1989).

George et al, Brain Res 1988; 440:35-379.

Grond S, Thomas M, Detlev Z et al, "Analgesic efficacy and safety of tramadol enantiomers in comparison with the racemate: a randomised, double-blind study with gynaecological patients using intravenous patient-controlled analgesia" Pain 1995; 62(3):313-320.

Wiebalck A et al, "Sind Tramadol-Enantiomere für die postoperative Schmerztherapie besser geeignet als das Racemat? Eine randomisierte, Plazebo- and Morphin-kontrollierte Doppelblindstudie", Der Anaesthesist, 1998; 47: 387-394.

Lintz et al, Arzneim.-Forsch./Drug Res. 1981; 31(11): 1932-1943.

Unlugenc H, Gunduz M, Ozalevli M, Akman H. A comparative study on the analgesic effect of tramadol, tramadol plus magnesium, and tramadol plus ketamine for postoperative pain management after major abdominal surgery. Acta anaesthesiologica Scandinavica 2002; 46:1025-30.

Chen Yong, Chan Sui Y, Ho Paul C. Isobolographic analysis of the analgesic interactions between ketamine and tramadol. Journal of pharmacy and pharmacology 2002; 54:623-31.

Wood J N and Docherty R (1997). Chemical activators of sensory neurons. *Annu Rev Physiol* 59: 457-482.

Bull S A, et al., *Discontinuing or switching selective serotonin-reuptake inhibitors*, Annals of Pharmacotherapy 2002; 36(4): 578-584.

Barbui C, et al., *Selective serotonin reuptake inhibitors versus tricyclic and heterocyclic antidepressants: comparison of drug adherence.*, In: The Cochrane Library, Issue 4, 2000. Oxford: Update Software.

Skaehill P A and Welch E B, *SSRI withdrawal syndrome*, 1997 American Society of Consultant Pharmacists, Inc.

Dharmananda S, A Bag of Pearls, 2004 Institute for Traditional Medicine, Portland, Oreg.

Lieberman J A, *History of the use of antidepressants in primary care*, Primary Care Companion, Journal of Clinical Psychiatry 2003; 5 (supplement 7).

Bryans J S, Davies N, Gee N S, Dissanayake V U K, Ratcliffe G S, Horwell D C, Kneen C O, Morrell A I, Oles R J, O'Toole J C, et al. (1998) Identification of novel ligands for the gabapentin binding site on the alpha2delta subunit of a calcium channel and their evaluation as anticonvulsant agents. *J Med Chem* 41: 1838-1845.

Cao Z, Ly J, and Bonhaus D W (2001) Effects of the GABAB receptor antagonist CGP55845 on the anticonvulsant actions of phenyloin, gabapentin and S(+)isobutylgaba. *Soc Neurosci Abstr* 27: 754.1.

Chaplan S R, Bach F W, Pogrel J W, Chung J M, and Yaksh T L (1994) Quantitative assessment of tactile allodynia in the rat paw. *J Neurosci Methods* 53: 55-63.

Cheng J-K, Lai Y-J, Chen C-C, Cheng C-R, and Chiou L-C (2003) Magnesium chloride and ruthenium red attenuate the antiallodynic effect of intrathecal gabapentin in a rat model of postoperative pain. *Anesthesiology* 98: 1472-1479.

Dickenson A H and Sullivan A F (1987) Peripheral origins and central modulation of subcutaneous formalin-induced activity of rat dorsal horn neurons. *Neurosci Lett* 83: 207-211.

Dubuisson D and Dennis S G (1977) The formalin test: a quantitative study of the analgesic effects of morphine, meperidine and brain stem stimulation in rats and cats. *Pain* 4: 161-174.

Field M J, Holloman E F, McCleary S, Hughes J, and Singh L (1997a) Evaluation of gabapentin and S-(+)-3-isobutylgaba in a rat model of postoperative pain. *J Pharmacol Exp Ther* 282: 1242-1246.

Field M J, Hughes J, and Singh L (2000) Further evidence for the role of the alpha2delta subunit of voltage dependent calcium channels in models of neuropathic pain. *Br J Pharmacol* 131: 282-286.

Field M J, Oles R J, Lewis A S, McCleary S, Hughes J, and Singh L (1997b) Gabapentin (neurontin) and S-(+)-3-isobutylgaba represent a novel class of selective antihyperalgesic agents. *Br J Pharmacol* 121: 1513-1522.

Fink K, Meder W, Dooley D J, and Gothert M (2000) Inhibition of neuronal Ca2+ influx by gabapentin and subsequent reduction of neurotransmitter release from rat neocortical slices. *Br J Pharmacol* 130: 900-906.

Gee N S, Brown J P, Dissanayake V U K, Offord J, Thurlow R, and Woodruff G N (1996) The novel anticonvulsant drug, gabapentin (neurontin), binds to the alpha2delta subunit of a calcium channel. *J Biol Chem* 271: 5768-5776.

Giardina W J, Decker M W, Porsolt R D, Roux S, Collins S D, Kim D J B, and Bannon A W (1998) An evaluation of the GABA uptake blocker tiagabine in animal models of neuropathic and nociceptive pain. *Drug Dev Res* 44: 106-113.

Goldlust A, Su T, Welty D F, Taylor C P, and Oxender D L (1995) Effects of the anticonvulsant drug gabapentin on enzymes in the metabolic pathways of glutamate and GABA. *Epilepsy Res* 22: 1-11.

Gotz E, Feuerstein T J, and Meyer D K (1993) Effects of gabapentin on release of gamma-aminobutyric acid from slices of rat neostriatum. *Drug Res* 43: 636-638.

Gould H J, Gould T N, Reeb S C, and Paul D (1997) The effect of gabapentin on inflammatory pain in rats. *Analgesia* 3: 131-139.

Gu Y and Huang L Y M (2002) Gabapentin potentiates N-methyl-D-aspartate receptor mediated currents in rat GABAergic dorsal horn neurons. *Neurosci Lett* 324: 177-180.

Hargreaves K, Dubner R, Brown F, Flores C, and Joris J (1988) A new and sensitive method for measuring thermal nociception in cutaneous hyperalgesia. *Pain* 32: 77-88.

Hunter J C, Gogas K R, Hedley L R, Jacobson L O, Kassotakis L, Thompson J, and Fontana D J (1997) The effect of novel anti-epileptic drugs in rat experimental models of acute and chronic pain. *Eur J Pharmacol* 324: 153-160.

Hwang J H and Yaksh T L (1997) Effect of subarachnoid gabapentin on tactile-evoked allodynia in a surgically-induced neuropathic pain model in the rat. *Reg Anesth* 22: 249-256.

Kim S H and Chung J M (1992) An experimental model of peripheral neuropathy produced by segmental spinal nerve ligation. *Pain* 50: 355-363.

Loscher W, Honack D, and Taylor C P (1991) Gabapentin increases aminooxyacetic acid-induced GABA accumulation in several regions of rat brain. *Neurosci Lett* 128: 150-154.

Lu Y and Westlund K N (1999) Gabapentin attenuates nociceptive behaviors in an acute arthritis model in rats. *J Pharmacol Exp Ther* 290: 214-219.

Luo Z D, Calcutt N A, Higuera E S, Valder C R, Song Y H, Svensson C I, and Myers R R (2002) Injury type-specific calcium channel alpha2delta-1 subunit up-regulation in rat neuropathic pain models correlates with antiallodynic effects of gabapentin. *J Pharmacol Exp Ther* 303: 1199-1205.

Luo Z D, Chaplan S R, Higuera E S, Sorkin L S, Stauderman K A, Williams M E, and Yaksh T L (2001) Upregulation of dorsal root ganglion alpha2delta calcium channel subunit and its correlation with allodynia in spinal nerve-injured rats. *J Neurosci* 21: 1868-1875.

Malan T P, Mata H P, and Porreca F (2002) Spinal GABAA and GABAB receptor pharmacology in a rat model of neuropathic pain. *Anesthesiology* 96: 1161-1167.

Maneuf Y P and McKnight A T (2001) Block by gabapentin of the facilitation of glutamate release from rat trigeminal nucleus following activation of protein kinase C or adenylyl cyclase. *Br J Pharmacol* 134: 237-240.

Marais E, Klugbauer N, and Hofmann F (2001) Calcium channel alpha2delta subunits-structure and gabapentin binding. *Mol Pharmacol* 59: 1243-1248.

Patel S, Naeem S, Kesingland A, Froestl W, Capogna M, Urban L, and Fox A (2001) The effects of GABAB agonists and gabapentin on mechanical hyperalgesia in models of neuropathic and inflammatory pain in the rat. *Pain* 90: 217-226.

Petroff O A, Rothman D L, Behar K L, Lamoureux D, and Mattson R H (1996) The effect of gabapentin on brain gamma-aminobutyric acid in patients with epilepsy. *Ann Neurol* 39: 95-99.

Puig S and Sorkin L S (1995) Formalin-evoked activity in identified primary afferent fibers: systemic lidocaine suppresses phase-2 activity. *Pain* 64: 345-355.

Rice A S C and Maton S (2001) Gabapentin in postherpetic neuralgia: a randomised, double blind, placebo controlled study. *Pain* 94: 215-224.

Shimoyama M, Shimoyama N, and Hori Y (2000) Gabapentin affects glutamatergic excitatory neurotransmission in the rat dorsal horn. *Pain* 85: 405-414.

Sutton K G, Martin D J, Pinnock R D, Lee K, and Scott R H (2002) Gabapentin inhibits high-threshold calcium channel currents in cultured rat dorsal root ganglion neurones. *Br J Pharmacol* 135: 257-265.

Taylor C P (2004) The biology and pharmacology of calcium channel alpha2-delta proteins. *CNS Drug Rev* 10: 183-188.

Taylor C P, Gee N S, Su T Z, Kocsis J D, Welty D F, Brown J P, Dooley D J, Boden P, and Singh L (1998) A summary of mechanistic hypotheses of gabapentin pharmacology. *Epilepsy Res* 29: 233-249.

Wiesenfeld-Hallin Z, Aldskogius H, Grant G, Hao J X, Hokfelt T, and Xu X J (1997) Central inhibitory dysfunctions: mechanisms and clinical implications. *Behav Brain Sci* 20: 420-425.

Xiao W H and Bennett G J (1996) Gabapentin has an antinociceptive effect mediated via a spinal site of action in a rat model of painful peripheral neuropathy. *Analgesia* 2: 267-273.

Yaksh T L, Ozaki G, McCumber D, Rathbun M, Svensson C, Malkmus S, and Yaksh M C (2001) An automated flinch detecting system for use in the formalin nociceptive bioassay. *J Appl Physiol* 90: 2386-2402.

Urban M O, Ren K, Park K T, Campbell B, Anker N, Stearns B, Aiyar J, Belley M, Cohen C, and Bristow L (2005) Comparison of the Antinociceptive Profiles of Gabapentin and 3-Methylgabapentin in Rat Models of Acute and Persistent Pain: Implications for Mechanism of Action. *J Pharm Exp Therap* 313: 1209-1216.

Bryans, J S & Wustrow, D J. (1999) *Med Res Rev* 19, 149-177.

Field, M J, Hughes, J & Singh, L. (2000) *Br J Pharmacol* 131, 282-286.

Maneuf, Y P, Hughes, J & McKnight, A T. (2001) *Pain* 93, 191-196.

Belliotti, T R, Capiris, T, Ekhato, I V, Kinsora, J J, Field, M J, Heffner, T G, Meltzer, L T, Schwarz, J B, Taylor, C P & Thorpe, A J, et al. (2005) *J Med Chem* 48, 2294-2307.

Klugbauer, N, Marais, E & Hofmann, F. (2003) *J Bioenerg Biomembr* 35, 639-647.

Luo, Z D, Chaplan, S R, Higuera, E S, Sorkin, L S, Stauderman, K A, Williams, M E & Yaksh, T L. (2001) *J Neurosci* 21, 1868-1875.

Luo, Z D, Calcutt, N A, Higuera, E S, Valder, C R, Song, Y H, Svensson, C I & Myers, R R J. (2002) *Pharmacol Exp Ther* 303, 1199-1205.

Field M J et al. (2006) Identification of the $\alpha 2\delta$-1 subunit of voltage-dependent calcium channels as a molecular target for pain mediating the analgesic actions of pregabalin; PNAS; 103: 17537-17542

Brown J P, Dissanayake V U, Briggs A R, Milic M R and Gee N S (1998) Isolation of the [$^3$H]gabapentin-binding protein $\alpha 2\delta$ $Ca^{2+}$ channel subunit from porcine brain: development of a radioligand binding assay for $\alpha 2\delta$ subunits using [$^3$H]leucine. *Anal Biochem* 255: 236-243.

Brown J P and Gee N S (1998) Cloning and deletion mutagenesis of the $\alpha 2\delta$ calcium channel subunit from porcine cerebral cortex. *J Biol Chem* 273: 25458-25465.

Dooley D J, Donovan C M and Pugsley T A J (2000) Stimulus-dependent modulation of [$^3$H]Norepinephrine release from rat neocortical slices by gabapentin and pregabalin. *J Pharmacol Exp Ther* 295: 1086-1093.

Gong H C, Hang J, Kohler W, Li L, and Su T Z (2001) Tissue-specific expression and gabapentin-binding properties of calcium channel A2$\delta$ subunit subtypes. *J Membrane Biol* 184: 35-43.

Piechan J L, Donevan S D, Taylor C P, Dickerson M R, and Li Z (2004) Pregabalin, a novel anticonvulsant, analgesic and anxiolytic drug, exhibits class-specific $\alpha 2\delta$-1 and $\alpha 2\delta$-2 calcium channel subunit binding. *Soc Neurosci Abstr* 30: 115.11.

Alden K J and Garcia J (2001) Differential effect of gabapentin on neuronal and muscle calcium currents. *J Pharmacol Exp Ther* 297: 727-735.

Bayer K, Seifollah A, and Zeilhofer H U (2004) Gabapentin may inhibit synaptic transmission in the mouse spinal cord dorsal horn through a preferential block of P/Q-type $Ca^{2+}$ channels. *Neuropharmacology* 46: 743-749.

Belliotti T, Ekhato I V, Capiris T, Kinsora J, Vartanian M G, Field M, Meltzer L T, Heffner T, Schwarz J B, Taylor C P, et al. (2005) Structure-activity relationships of pregabalin and analogs that target the $\alpha 2\delta$ protein. *J Med Chem* 48: 2294-2307.

Bian F, Li Z, Offord J D, Davis M D, McCormick J A, Taylor C P, and Walker L C (2006) Calcium channel alpha$_2$-delta Type 1 subunit is the major binding protein for pregabalin in neocortex, hippocampus, amygdala and spinal cord: an ex vivo autoradiographic study in alpha$_2$-delta type 1 genetically modified mice. *Brain Res* 1075: 68-80.

Canti C, Davies A, and Dolphin A C (2004) Calcium channel alpha2-delta subunits: Structure, functions and target site for drugs. *Curr Neuropharmacol* 1: 209-217.

Dooley D J, Donovan C M, Meder W P, and Whetzel S Z (2002) Preferential action of gabapentin and pregabalin at P/Q-type voltage-sensitive calcium channels: inhibition of K$^+$-evoked [$^3$H]-norepinephrine release from rat neocortical slices. *Synapse* 45: 171-190.

Dooley D J, Mieske C A, and Borosky S A (2000) Inhibition of K(+)-evoked glutamate release from rat neocortical and hippocampal slices by gabapentin. *Neurosci Lett* 280: 107-110.

Fehrenbacher J C, Taylor C P, and Vasko M R (2003) Pregabalin and gabapentin reduce release of substance P and CGRP from rat spinal tissues only after inflammation or activation of protein kinase C. *Pain* 105: 133-144.

Fink K, Meder W, Dooley D J, and Gothert M (2000) Inhibition of neuronal $Ca^{2+}$ influx by gabapentin and subsequent reduction of neurotransmitter release from rat neocortical slices. *Br J Pharmacol* 130: 900-906.

Gee N S, Brown J P, Dissanayake V U, Offord J, Thurlow R, and Woodruff G N (1996) The novel anticonvulsant drug, gabapentin (Neurontin), binds to the $\alpha 2\delta$ subunit of a calcium channel. *J Biol Chem* 271: 5768-5776.

Goslin K, Asmussen H, and Banker G (1998) Rat hippocampal neurons in lowdensity culture, in *Culturing Nerve Cells* (Banker G and Goslin K eds) pp 339-370, The MIT Press, Cambridge, Mass.

Jarvis S E and Zamponi G W (2001) Interactions between presynaptic $Ca^{2+}$ channels, cytoplasmic messengers and proteins of the synaptic vesicle release complex. *Trends Pharmacol Sci* 22: 519-525.

Maneuf Y P, Hughes J, and McKnight A T (2001) Gabapentin inhibits the substance P-facilitated K$^+$-evoked release of [$^3$H]glutamate from rat caudial trigeminal nucleus slices. *Pain* 93: 191-196.

McClelland D, Evans R M, Barkworth L, Martin D J, and Scott R H (2004) A study comparing the actions of gabapentin and pregabalin on the electrophysiological properties of cultured DRG neurones from neonatal rats. *BMC Pharmacol* 4: 14-24.

Piechan J L, Donevan S D, Taylor C P, Dickerson M R, and Li Z (2004) Pregabalin, a novel anticonvulsant, analgesic and anxiolytic drug, exhibits class-specific alpha$_2$-delta-1 and alpha$_2$-delta-2 calcium channel subunit binding. *Soc Neurosci Abstr* 30: 115.11.

Shimoyama M, Shimoyama N, and Hon Y (2000) Gabapentin affects glutamatergic excitatory neurotransmission in the rat dorsal horn. *Pain* 85: 405-414.

Simkus C R and Stricker C (2002) The contribution of intracellular calcium stores to mEPSCs recorded in layer II neurones of rat barrel cortex. *J Physiol* 545: 521-535.

Suarez L M, Suarez F, Del Olmo N, Ruiz M, Gonzalez-Escalada J R, and Solis J M (2005) Presynaptic NMDA autoreceptors facilitate axon excitability: a new molecular target for the anticonvulsant gabapentin. *Eur J Neurosci* 21: 197-209.

Taylor C P (2004) Meeting report: the biology and pharmacology of calcium channel α2-δ proteins. *CNS Drug Rev* 10: 159-164.

van Hooft J A, Dougherty J J, Endeman D, Nichols R A, and Wadman W J (2002) Gabapentin inhibits presynaptic Ca$^{2+}$ influx and synaptic transmission in rat hippocampus and neocortex. *Eur J Pharmacol* 449: 221-228.

Rodd E H. Chemistry of Carbon Compounds, Elsevier Publ, New York, 1960.

Holzer P (1988). Local effector functions of capsaicin-sensitive sensory nerve endings: involvement of tachykinins, calcitonin gene-related peptide and other neuropeptides. *Neuroscience* 24: 739-768.

Holzer P (1991). Capsaicin: cellular targets, mechanisms of action, and selectivity for thin sensory neurons. *Pharmacol Rev* 43: 143-201.

Winter J, Bevan S and Campbell E A (1995). Capsaicin and pain mechanisms. *Br J Anaesth* 75: 157-168.

Caterina M J and Julius D (1999). Sense and specificity: a molecular identity for nociceptors. *Curr Opin Neurobiol* 9: 525-530.

Caterina M J and Julius D (2001). The vanilloid receptor: a molecular gateway to the pain pathway. *Annu Rev Neurosci* 24: 487-517.

Caterina M J, Schumacher M A, Tominga M, Rosen T A, Levine J D and Julius D (1997). The capsaicin receptor: a heat-activated ion channel in the pain pathway. *Nature (Lond)* 389: 816-824.

Tominaga M, Caterina M J, Malmberg A B, Rosen T A, Gilbert H, Skinner K, Raumann B E, Basbaum A I and Julius D (1998). The cloned capsaicin receptor integrates multiple pain-producing stimuli. *Neuron* 21: 531-543.

Wood J N and Docherty R (1997). Chemical activators of sensory neurons. *Annu Rev Physiol* 59: 457-482.

Kenins P (1982). Response of single nerve fibres to capsaicin applied to the skin. *Neurosci Lett* 29: 83-88.

Lynn B, Ye W and Costell B (1992). The actions of capsaicin applied topically to the skin of the rat on C-fibre afferents, antidromic vasodilation and substance P levels. *Br J Pharmacol* 107: 400-406.

Carter R B and Francis W R (1991). Capsaicin desensitization to plasma extravasation by antidromic C-fibre stimulation is not assoiciated with antinociception in the rat. *Neurosci Lett* 127: 49-52.

McMahon S B, Lewin G and Bloom S R (1991). The consequences of long-term topical capsaicin application in the rat. *Pain* 44: 301-310.

Simone D A, Baumann T K and LaMotte R H (1989). Dose-dependent pain and mechanical hyperalgesia in humans after intradermal injection of capsaicin. *Pain* 38: 99-107.

Singh S, Natarajan K, Aggarwal B B (1996). Capsaicin (8-methyl-N-vanillyl-6-nonenamide) is a potent inhibitor of nuclear transcription factor-NB activation by diverse agents. *J. Immunol.* 157:4412.

Szallasi A & Blumberg P M (1999). Vanilloid (Capsaicin) receptors and mechanisms. *Pharmacol. Rev.,* 51, 159-212.

Tanden R et al, (1992). "Topical capsaicin in painful diabetic neuropathy. Effect on sensory function." Diabetes Care. 15, 8-14.

Nolano M, Simone D A, Wendelschafer-Crabb G, Johnson T, Hazen E and Kennedy W R (1999). Topical capsaicin in humans: parallel loss of epidermal nerve fibres and pain sensation. *Pain* 81: 135-145.

Watson C P N (1994). Topical capsaicin as an adjuvant analgesic. *J Pain Symptom Manage* 9: 425-433.

Watanabe A. et al, Efficacy of capsaicin ointment (Zostrix) in the treatment of herpetic pain and post-herpetic neuralgia, Pain Clinic 15:709-713, 1994.

Bernstein J E. et al, Topical capsaicin treatment of chronic post-herpetic neuralgia, J. Am. Acad. Dermatol. 21: 265-270, 1989.

Watson C P N. et al, (1993). A randomized vehicle-controlled trial of topical capsaicin in the treatment of post-herpetic neuralgia, Clin. Ther. 15:510-526.

Rains C, Bryson H M (1995). Topical capsaicin. A review of its pharmacological properties and therapeutic potential in post-herpetic neuralgia, diabetic neuropathy and osteoarthritis. *Drugs Aging.* 7(4):317-28.

Watson C P N and Evans R J (1992). The postmastectomy pain syndrome and topical capsaicin: a randomized trial. *Pain* 51: 375-379.

Dini D, Bertelli G, Gozza A and Formo G G (1993). Treatment of the post-mastectomy pain syndrome with topical capsaicin. *Pain* 54: 223-226.

Epstein J B and Marcoe J H (1994). Topical capsaicin for treatment of oral neuropathic pain and trigeminal neuralgia. *Oral Surg Oral Med Oral Pathol* 77: 135-140.

Hersh E V, Pertes R A and Ochs H A (1994). Topical capsaicin—pharmacology and potential role in the treatment of temperomandibular pain. *J Clin Dent* 5: 54-59.

Marks D R, Rapoport A, Padla D, Weeks R, Rosum R, Sheftell F and Arrowsmith F (1993). A double-blind placebo-controlled trial of intranasal capsaicin for cluster headache. *Cephalgia* 13: 114-116.

McCarthy G M and McCarthy D J (1992). Effect of topical capsaicin in the therapy of painful osteoarthritis of the hands. *J Rheumatol* 19: 604-607.

Hautkappe M, Roisen M F, Toledano A, Roth S, Jeffries J A and Ostermeier A M (1998). Review of the effectiveness of capsaicin for painful cutaneous disorders and neural dysfunction. *Clin J Pain* 14: 97-106.

Low P A, Opfer-Gehrking T L, Dyck P J, Litchy W J and O'Brien P C (1995). Double-blind, placebo-controlled study of the application of capsaicin cream in chronic distal painful polyneuropathy. *Pain* 62: 163-168.

Paice J A, Ferrans C E, Lashley F R, Shott S, Vizgirda V and Pitrak D (2000). Topical capsaicin in the management of HIV-associated peripheral neuropathy. *J Pain Symptom Manage* 19: 45-52.

Fuchs P N, Pappagallo M and Meyer R A (1999). Topical EMLA® pre-treatment fails to decrease the pain induced by 1% topical capsaicin. *Pain* 80: 637-642.

Fuller R W (1991). Pharmacology of inhaled capsaicin in humans. Respirat. Med. 85 (Suppl. A): 31-34.

Rumsfield, J A, and West D (1991). Topical capsaicin in dermatological and peripheral pain disorders. DICP, Ann. Pharmacotherap. 25: 381-387.

Lynn B. Capsaicin: actions on nociceptive C-fibres and therapeutic potential. *Pain* 1990; 41:61-9.

Marsh S J, Stansfeld C E, Brown D A, Davey R, McCarthy D. The mechanism of action of capsaicin on sensory C-type neurons and their axons in vitro. *Neuroscience* 1987; 23: 275-89.

Nolano M, Simone D A, Wendelschafer-Crabb G, Johnson T, Hazen E, Kennedy W R. Topical capsaicin in humans: parallel loss of epidermal nerve fibers and pain sensation. *Pain* 1999; 81:135-45.

Van Rijswijk J B, Boeke E L, Keizer J M, Mulder P G, Blom H M, Fokkens W J. Intranasal capsaicin reduces nasal hyperreactivity in idiopathic rhinitis: a double-blind randomized application regimen study. *Allergy.* 2003 58(8): 754-61.

Mori A, et al, Capsaicin, a component of red peppers, inhibits the growth of androgen-independent, p-53 mutant prostate cancer cells. *Cancer Res* 2006; 66(6): 3222-29.

Keret D, Goldin E. Topical capsaicin—a novel and effective treatment for idiopathic intractable pruritus ani: a randomised, placebo controlled, crossover study. Gut. 2003; 52(9):1323-6.

Markowitz J S, Patrick K S. Venlafaxine-tramadol similarities. Medical Hypotheses 1998; 51:167-8.

Lang E, Hord A H, Denson D. Venlafaxine hydrochloride (Effexor) relieves thermal hyperalgesia in rats with an experimental mononeuropathy. Pain 1998; 68:151-5.

Schreiber S, Backer M M, Pick C G. The antinociceptive effect of venlafaxine in mice is mediated through opioid and adrenergic mechanisms. Neuroscience Letters 1999; 273: 85-8.

Galer B S. Neuropathic pain of peripheral origin: advances in pharmacologic treatment. Neurology 1995; 45(suppl 9):S17-25.

Galer B S. Painful polyneuropathy: diagnosis, patho-physiology, and management. Semin Neurol 1994; 14:237-46.

McQuay H J, Trainer M, Nye B A, Carroll D, Wiffen P J, Moore R A. A systematic review of antidepressants in neuropathic pain. Pain 1996; 68:217-27.

Sindrup S H, Jensen T S. Efficacy of pharmacological treatments of neuropathic pain: an update and effect related to mechanism of drug action. Pain 1999; 83:389-400.

Kumar D, Alvaro M S, Julka I S, et al. Diabetic peripheral neuropathy: effectiveness of electrotherapy and amitriptyline for symptomatic relief Diabetes Care 1998; 21:1322-5.

Lipman A G. Analgesic drugs for neuropathic and sympathetically maintained pain. Clin Geriatr Med 1996; 12:501-15.

Watson C P N, Vernich L, Chipman M, et al. Nortriptyline versus amitriptyline in postherpetic neuralgia. Neurology 1998; 51:1166-71.

Bowsher D. Post-herpetic neuralgia in older patients: incidence and optimal treatment. Drugs Aging 1994; 5: 411-18.

Johnson R W. Herpes zoster and postherpetic neuralgia: optimal treatment. Drugs Aging 1997; 10:80-94.

Bryson H M, Wilde M I. Amitriptyline: a review of its pharmacological properties and therapeutic use in chronic pain states. Drugs Aging 1996; 8:459-76.

Magni G. The use of antidepressants in the treatment of chronic pain: a review of the current evidence. Drugs 1991; 42:730-48.

Max M. Treatment of post-herpetic neuralgia: antidepressants. Ann Neurol 1994; 35:S50-3.

Bowsher D. Neurogenic pain syndromes and their management. Br Med Bull 1991; 47:644-66.

Gonzales G R. Central pain: diagnosis and treatment strategies. Neurology 1995; 45(suppl 9):S11-19.

Bowsher D. The management of central post-stroke pain. Postgrad Med J 1995; 71:598-604.

Leijon G, Boivie J K. Central post-stroke pain: a controlled trial of amitriptyline and carbamazepine. Pain 1989; 36:27-36.

Jacox A, Carr D B, Payne R, et al. Clinical practice guideline number 9: management of cancer pain. Rockville, Md.: U.S. Department of Health and Human Services, Agency for Health Care Policy and Research, 1994. AHCPR publication no. 94-0592.

Levy M H. Pharmacologic treatment of cancer pain. N Engl J Med 1996; 335:1124-32.

Calissi P T, Jaber L A. Peripheral diabetic neuropathy: current concepts in treatment. Ann Pharmacother 1995; 29:769-77.

Jacobson L O, Bley K, Hunter J C, et al. Anti-thermal hyperalgesic properties of antidepressants in a rat model of neuropathic pain [abstr]. In: Proceedings of the 14th annual meeting of the American Pain Society. Glenview, Ill.: APS, 1995:A105.

Bressler R, Katz M D. Drug therapy for geriatric depression. Drugs Aging 1993; 3:195-219.

Rudorfer M V, Manji H K, Potter W Z. Comparative tolerability profiles of the newer versus older antidepressants. Drug Saf 1994; 10:18-46.

Billings J A. Neuropathic pain. J Palliat Care 1994; 10:40-3.

Emanuele N V, Emanuele M A. Drugs to treat the tissue complications of diabetes: peripheral neuropathy. Compr Ther 1995; 21:579-82.

Garner E M, Kelly M W, Thompson D F. Tricyclic antidepressant withdrawal syndrome. Ann Pharmacother 1993; 27:1068-72.

Nau C, Seaver M, Wang S Y, and Wang G K. Block of human heart hH1 sodium channels by amitriptyline. *J Pharmacol Exp Ther* 292: 1015-1023, 2000.

Catterall W A (1995) Structure and function of voltage-gated ion channels. *Annu Rev Biochem* 64: 493-531.

Fozzard H A and Hanck D A (1996) Structure and function of voltage-dependent sodium channels: Comparison of brain II and cardiac isoforms. *Physiol Rev* 76: 887-926.

Ragsdale D S, McPhee J C, Scheuer T and Catterall W A (1996) Common molecular determinants of local anesthetic, antiarrhythmic, and anticonvulsant block of voltage-gated $Na^+$ channels. *Proc Natl Acad Sci USA* 93: 9270-9275.

Song J E T, Ham S S, Shin Y K, Lee C S. Amitriptyline modulation of $Na^+$ channels in rat dorsal root ganglion neurons. Eur J Pharmacol 2000; 401: 297-305.

Gold M S, Levine J D. DAMGO inhibits prostaglandin $E_2$-induced potentiation of a TTX-resistant $Na^+$ current in rat sensory neurons in vitro. Neurosci Lett 1996; 212: 83-6.

Sawynok J, Esser M J, Reid A R. Antidepressants as analgesics: an overview of central and peripheral mechanisms of action. J Psychiatry Neurosci 2001; 26: 21-8.

Gellens M E, George A L, Chen L, Chahine M, Horn R, Barchi R L and Kallen R G (1992) Primary structure and functional expression of the human cardiac tetrodotoxin-insensitive voltage-dependent sodium channel. *Proc Natl Acad Sci USA* 89: 554-558.

Baldessarini R J (1995) Drugs and the treatment of psychiatric disorders, in *The Pharmacological Basis of Therapeutics* (Hardman J G, Limbird L E, Molinoff P B, Ruddon R W and Gilman A G eds) pp 431-459, McGraw-Hill, New York.

Monks R and Merskey H (1984) Psychotropic drugs, in *Textbook of Pain* (Wall P D and Melzack R eds) pp 526-537, Churchill Livingstone, N.Y.

Bryson H M and Wilde M I (1996) Amitriptyline. A review of its pharmacological properties and therapeutic use in chronic pain states. *Drugs Aging* 8: 459-476.

Nattel S (1985) Frequency-dependent effects of amitriptyline on ventricular conduction and cardiac rhythm in dogs. *Circulation* 72: 898-906.

Nattel S, Keable H and Sasyniuk B I (1984) Experimental amitriptyline intoxication: Electrophysiologic manifestations and management. *J Cardiovasc Pharmacol* 6: 83-89.

Amsterdam J, Brunswick D and Mendels J (1980) The clinical application of tricyclic antidepressant pharmacokinetics and plasma levels. *Am J Psychiatry* 137: 653-662.

Kuo C C (1998) Imipramine inhibition of transient K$^+$ current: An external open channel blocker preventing fast inactivation. *Biophys J* 12: 2845-2857.

Pancrazio J J, Kamatchi G L, Roscoe A K and Lynch C (1998) Inhibition of neuronal Na$^+$ channels by antidepressant drugs. *J Pharmacol Exp Ther* 284: 208-214.

Hille B (1992) Mechanisms of block, in *Ionic Channels of Excitable Membranes* pp 390-422, Sinauer Associate Inc., Sunderland, Mass.

Barber M J, Starmer C F and Grant A O (1991) Blockade of cardiac sodium channels by amitriptyline and diphenylhydantoin: Evidence for two use-dependent binding sites. *Circ Res* 69: 677-696.

Moret C, Charveron M, Finberg J P, Couzinier J P, Briley M (1985). "Biochemical profile of midalcipran (F 2207), 1-phenyl-1-diethyl-aminocarbonyl-2-aminomethyl-cyclopropane (Z) hydrochloride, a potential fourth generation antidepressant drug". *Neuropharmacology* 24 (12): 1211-9.

Briley M, Prost J F, Moret C (1996). "Preclinical pharmacology of milnacipran". *International clinical psychopharmacology* 11 Suppl 4: 9-14.

Puozzo C, Panconi E, Deprez D (2002). "Pharmacology and pharmacokinetics of milnacipran". *International clinical psychopharmacology* 17 Suppl 1: S25-35.

Leinonen E, Lepola U, Koponen H, Mehtonen O P, Rimon R (1997). "Long-term efficacy and safety of milnacipran compared to clomipramine in patients with major depression". *Acta psychiatrica Scandinavica* 96 (6): 497-504.

Papakostas G I, Fava M (2007). "A meta-analysis of clinical trials comparing milnacipran, a serotonin—norepinephrine reuptake inhibitor, with a selective serotonin reuptake inhibitor for the treatment of major depressive disorder". *European neuropsychopharmacology: the journal of the European College of Neuropsychopharmacology* 17 (1): 32-6.

Kako Y, Niwa Y, Toyomaki A, et al (2007). "A case of adult attention-deficit/hyperactivity disorder alleviated by milnacipran". *Prog. Neuropsychopharmacol. Biol. Psychiatry* 31 (3): 772-5.

Briley M. et al., Int. Clin. Psychopharmac., 1996, 11:10-14.

Puech A. et al., 1997, hit. Clin. Psychopharm., 12:99-108.

Guelfi J. D., 1998, Int. Clin. Psychopharm., 13:121-128.

Tignol J. et al., 1998, Acta Psychiatrica Scandinavica, 97:157-165.

Caron J. et al., 1993, Eur. Neuropsychopharmacol., 3:493-500.

Leinonen E., 1997, Acta Psychiatr. Scand., 96:497-504.

Von Frenckell R et al., 1990, Int. Clin. Psychopharmacology., 5:49-56.

Sellinger et al., Fed. Proc., 38, 592 (1979).

Pandey et al., Fed. Proc., 38, 592 (1979).

Marchettini P, Teloni L, Formaglio F and Lacerenza M (2004): Pain in diabetic neuropathy case study: whole patient management. *European Journal of Neurology,* 11 (Suppl. 1):12-21.

Sang C N, Booher S, Gilron I, Parada S, Max M B (2002): Dextromethorphan and memantine in painful diabetic Neuropathy and postherpetic neuralgia: Efficacy and dose Response trials. *Anesthesiology,* 96: 1053-1061.

Sindrup S H, Andersen K, Madsen F, Smith T, Brosen G, Jensen T S (1999): Tramadol relieves pain and allodynia in Polyneuropathy: a randomized, double blind, controlled Trial. *Pain,* 83:85-90.

Russell I J, Kamin M, Bennett R M, Schnitzer T J, Green J A, Katz W A (2000): Efficacy of tramadol in treatment of pain in fibromyalgia. *J Clin Rheumatol,* 6:250-257.

Arnold L M, Goldenberg D L, Stanford S B, Lalonde J K, et al. (2007): Gabapentin in the treatment of fibromyalgia: A randomized, double-blind, placebo-controlled, multicenter trial. *Arthritis Rheum.,* 56(4):1336-44.

Staud R; Vierck C J; Robinson M E; Price D D (2005): Effects of the N-methyl-D-aspartate receptor antagonist dextromethorphan on temporal summation of pain are similar in fibromyalgia patients and normal control subjects. *J Pain,* 6(5):323-32.

Biasi G, Manca S, Manganelli S, Marcolongo R (1998): Tramadol in the fibromyalgia syndrome: a controlled clinical trial versus placebo. *Int J Clin Pharmacol Res,* 18(1):13-19.

Arnold L M, Goldenberg D L, Standford S H, et al (2007): Gabapentin in the treatment of fbromyalgia: a randomized double-blind, placebo-controlled, multicenter trial. *Arthr Rheum.,* 56:1336-1344.

Perrot S, Dickenson A K Bennett R M (2008): Fibromyalgia: Harmonizing Science with Clinical Practice Considerations. *Pain Practice,* 8 (3):177-189.

Clark S R, Bennett R M (2000): Supplemental dextromethorphan in the treatment of fibromyalgia. A double blind, placebo controlled study of efficacy and side effects. *Arthritis Rheum.,* 43:S333.

The invention claimed is:

1. A pharmaceutical composition comprising a synergistic combination of:
   a) 35 mg of tramadol or a pharmaceutically acceptable salt thereof;
   b) 35 mg of dextromethorphan or a pharmaceutically acceptable salt thereof; and
   c) 90 mg of gabapentin or a pharmaceutically acceptable salt thereof.

2. The pharmaceutical composition of claim 1, wherein the dextromethorphan, tramadol and/or gabapentin is in the form of a pharmaceutically acceptable salt.

3. The pharmaceutical composition of claim 1, wherein the pharmaceutical composition is an oral dosage form.

4. The pharmaceutical composition of claim 3, wherein the oral dosage form is in a form selected from the group consisting of a tablet, troche, lozenge, aqueous solution, solid or semi-solid solutions or mixture, oily suspension or solution, dispersible powder or granule, emulsion, multiparticulate formulation, syrup and elixir.

5. A method of treating diabetic neuropathy pain or fibromyalgia pain in a subject in need of such treatment comprising administering to the subject the pharmaceutical composition of claim 1 twice daily, and wherein the pharmaceutical composition is effective to treat the pain in the subject.

6. The method of claim 5, wherein the method comprises administering the agents simultaneously.

7. The method of claim 6, wherein the agents are administered in a single formulation.

8. The method of claim 5, wherein the method comprises administering the agents sequentially.

* * * * *